United States Patent [19]
Kogasaka et al.

[11] Patent Number: 5,643,293
[45] Date of Patent: Jul. 1, 1997

[54] SUTURING INSTRUMENT

[75] Inventors: Takahiro Kogasaka; Toshihiko Suzuta, both of Hachioji; Shiro Bito, Tokyo; Minoru Tsuruta, Hachioji; Naoki Uchiyama, Kokubunji; Kunihide Kaji, Koganei, all of Japan

[73] Assignee: Olympus Optical Co., Ltd., Tokyo, Japan

[21] Appl. No.: 360,397

[22] Filed: Dec. 21, 1994

[30] Foreign Application Priority Data

| Dec. 29, 1993 | [JP] | Japan | 5-355398 |
| Apr. 14, 1994 | [JP] | Japan | 6-076038 |
| Apr. 25, 1994 | [JP] | Japan | 6-086574 |
| Dec. 6, 1994 | [JP] | Japan | 6-302299 |

[51] Int. Cl.⁶ .................................................. A61B 17/00
[52] U.S. Cl. .......................... 606/148; 606/139; 112/169
[58] Field of Search ................................. 606/139, 144, 606/145, 148, 1; 112/169, 80.03

[56] References Cited

U.S. PATENT DOCUMENTS

| 4,038,988 | 8/1977 | Périssé | 606/148 |
| 4,050,465 | 9/1977 | Périssé | 606/148 |
| 5,144,961 | 9/1992 | Chen et al. | |
| 5,234,445 | 8/1993 | Walker et al. | |
| 5,282,809 | 2/1994 | Kammerer et al. | |
| 5,284,485 | 2/1994 | Kammerer et al. | |
| 5,312,423 | 5/1994 | Rosenbluth et al. | 606/148 |
| 5,318,578 | 6/1994 | Hasson | 606/139 |
| 5,423,836 | 6/1995 | Brown | 606/148 |
| 5,454,820 | 10/1995 | Kammerer et al. | 606/139 |
| 5,472,446 | 12/1995 | de la Torre | 606/139 |

Primary Examiner—Jeffrey A. Schmidt
Attorney, Agent, or Firm—Frishauf, Holtz, Goodman, Langer & Chick

[57] ABSTRACT

A medical instrument performs at least one of suture and ligation to form a suitable knot in a piece of suture within a body cavity. This medical instrument includes a suture having a first end portion, a second end portion, and at least one loop formed in advance at an intermediate portion between the first and second end portions to have a predetermined size, and a suture suitable for application to a body tissue, and a cylindrical body for holding the loop to almost maintain the size thereof. The body has a fastening portion for fastening at least one portion of the suture. The medical instrument further includes an inserting instrument which is to be inserted into the body cavity, which has a distal end portion that can be arranged in the body cavity, and an operating portion, arranged outside the body, for operating the distal end portion thereof, and on which a holding member having the suture wound thereon is mounted. The distal end portion of the inserting instrument projects beyond the loop held by the holding member, and has a gripping member capable of gripping the suture. This inserting instrument causes the first end portion of the suture gripped near an insertion port to the body cavity and in the body cavity to pass through the loop, thereby forming a knot.

14 Claims, 52 Drawing Sheets

PROXIMAL END PORTION OF INNER CYLINDER ←

DISTAL END OF INNER CYLINDER →

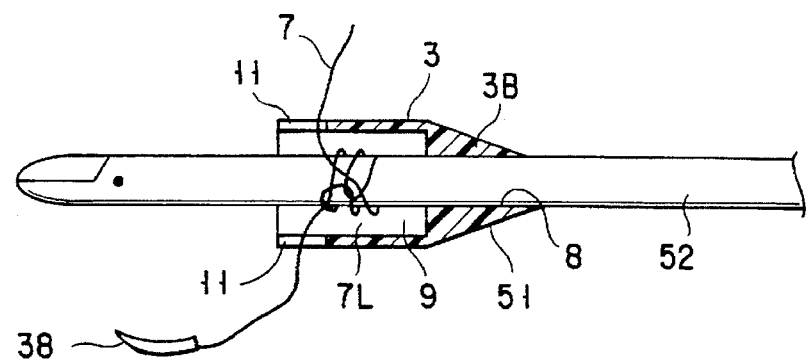
F I G. 21
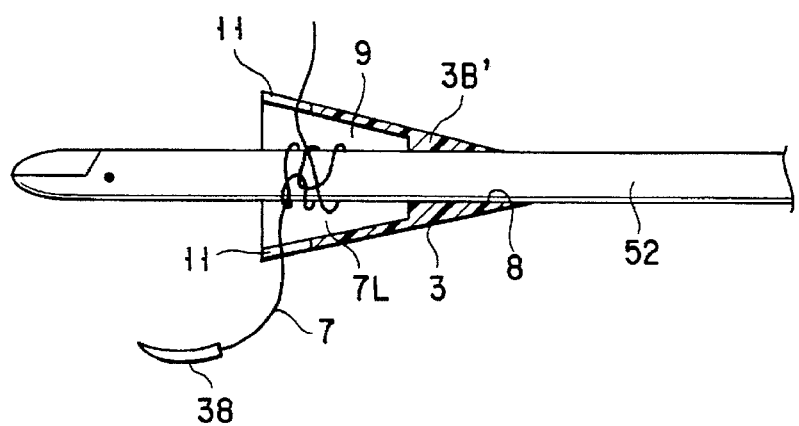
F I G. 22
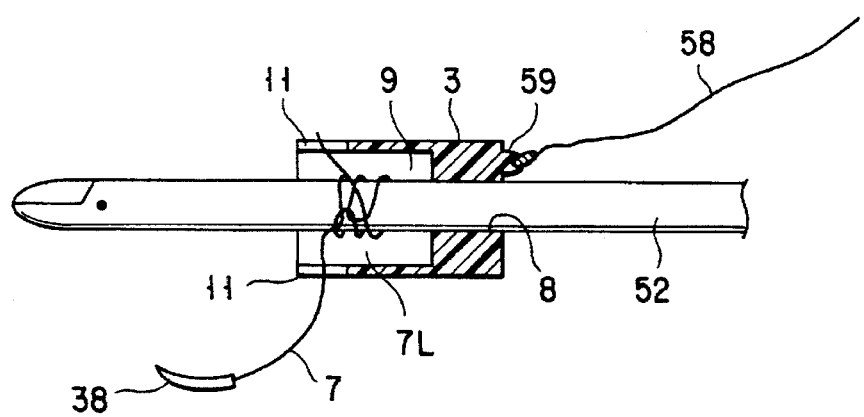
F I G. 23

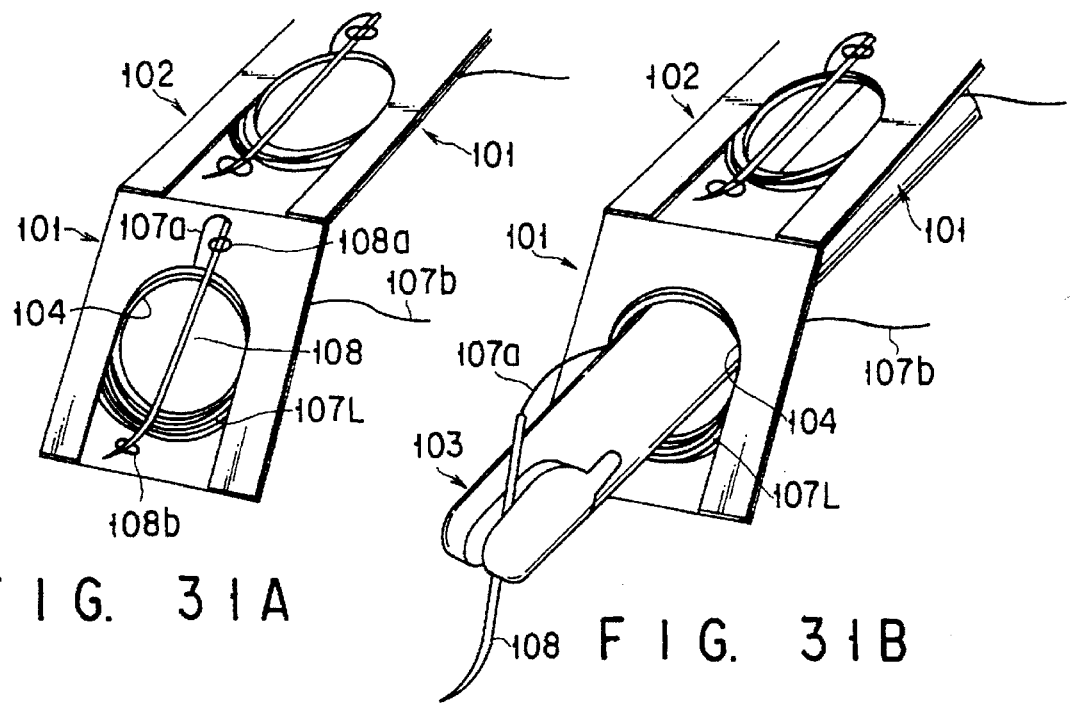
FIG. 31A
FIG. 31B
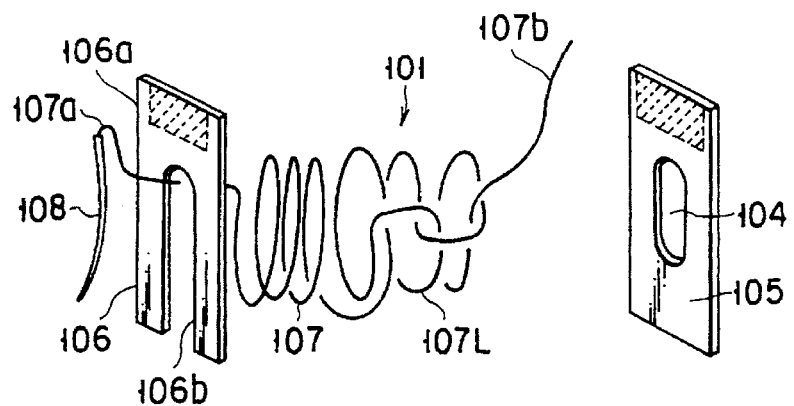
FIG. 31C
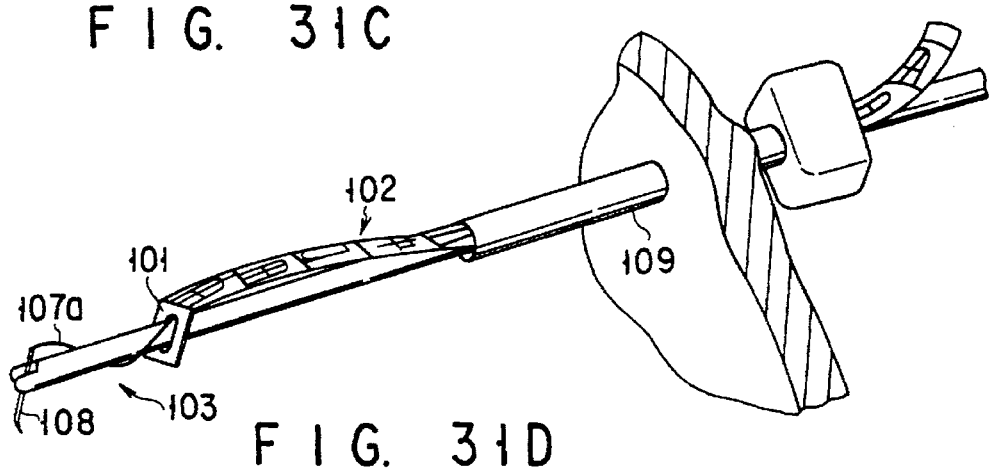
FIG. 31D

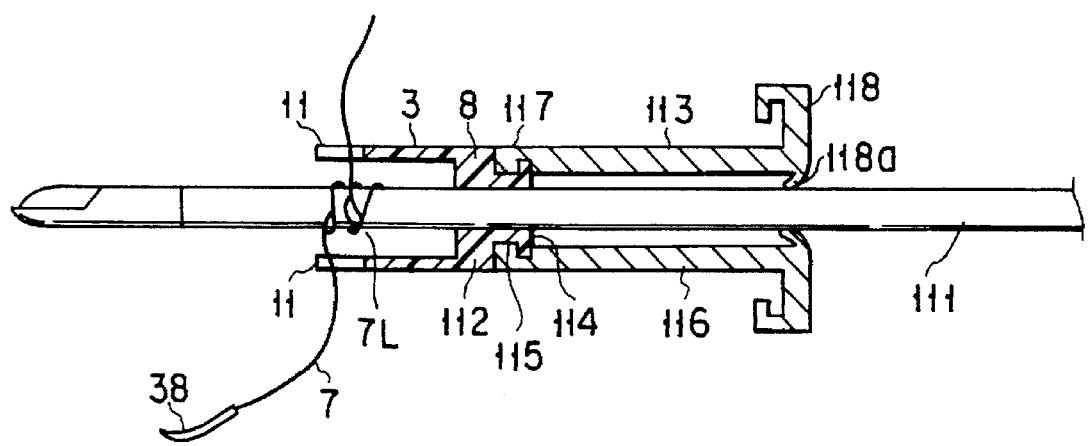
F I G. 32
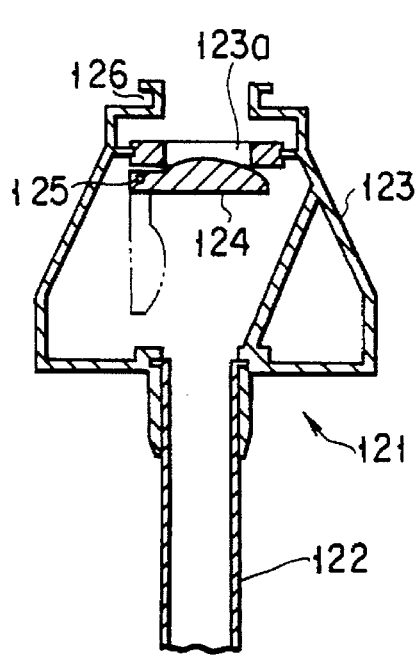
F I G. 33A
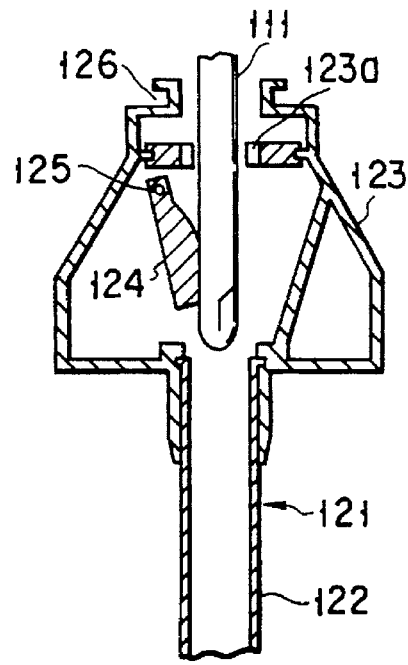
F I G. 33B

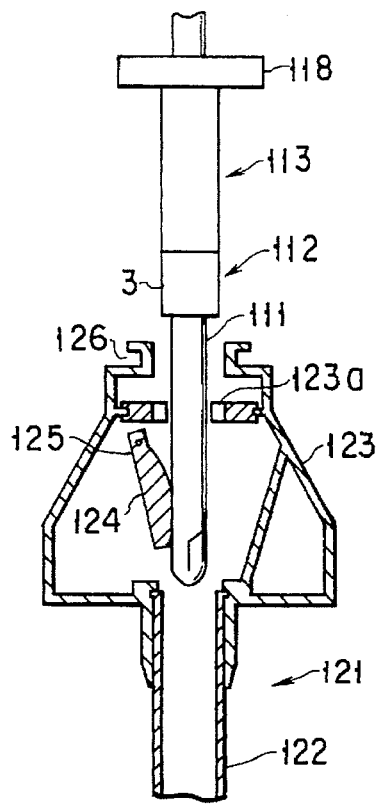
F I G. 34A
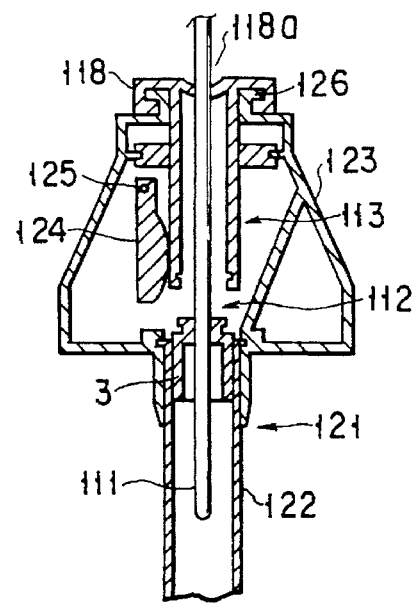
F I G. 34B
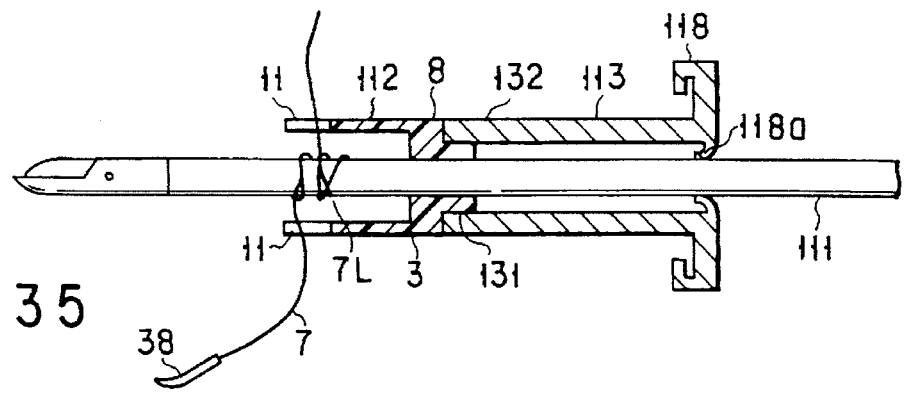
F I G. 35
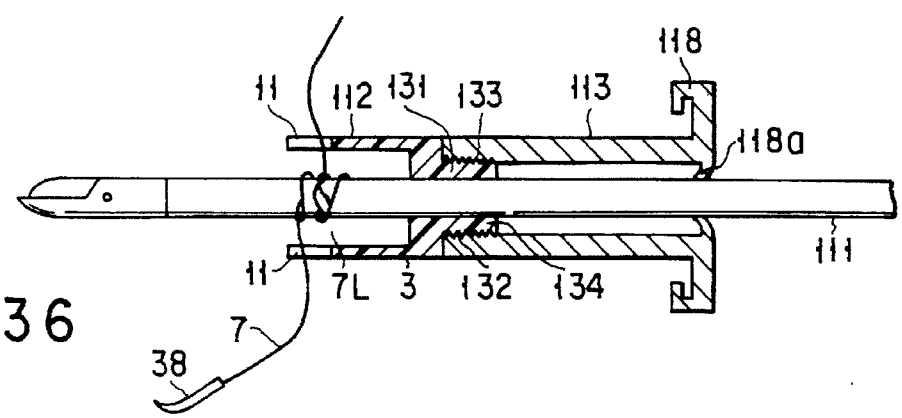
F I G. 36

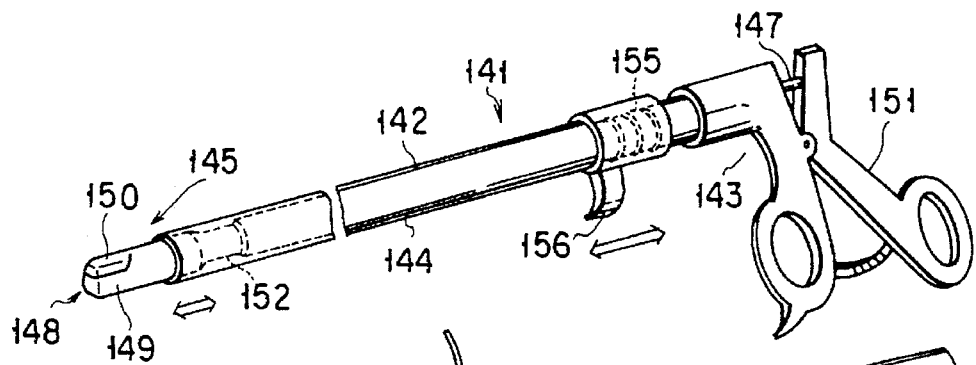
F I G. 37A
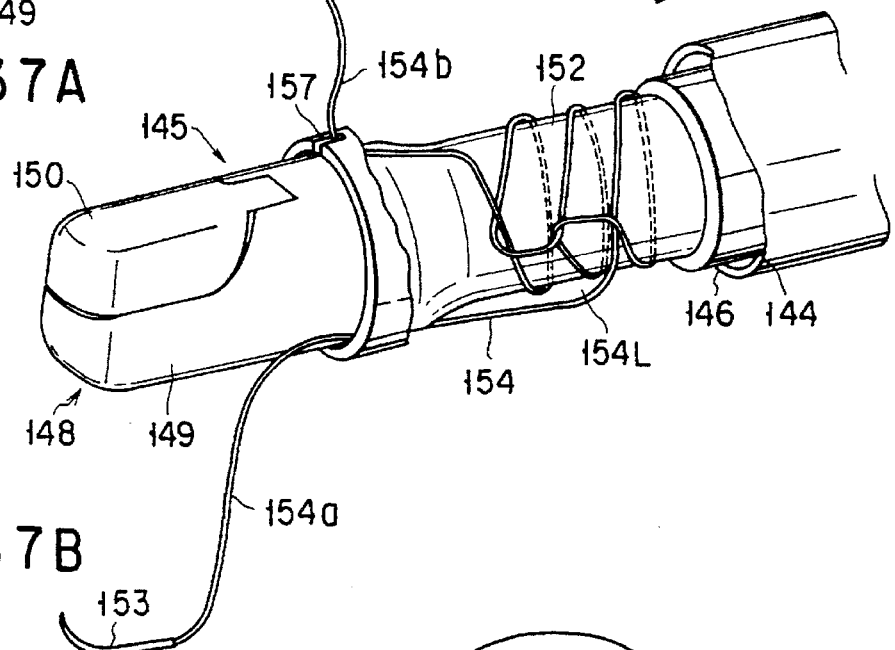
F I G. 37B
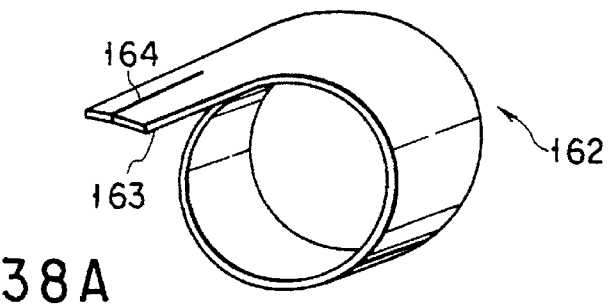
F I G. 38A
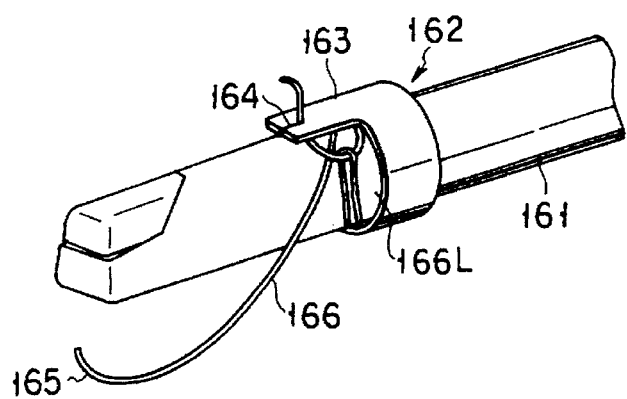
F I G. 38B

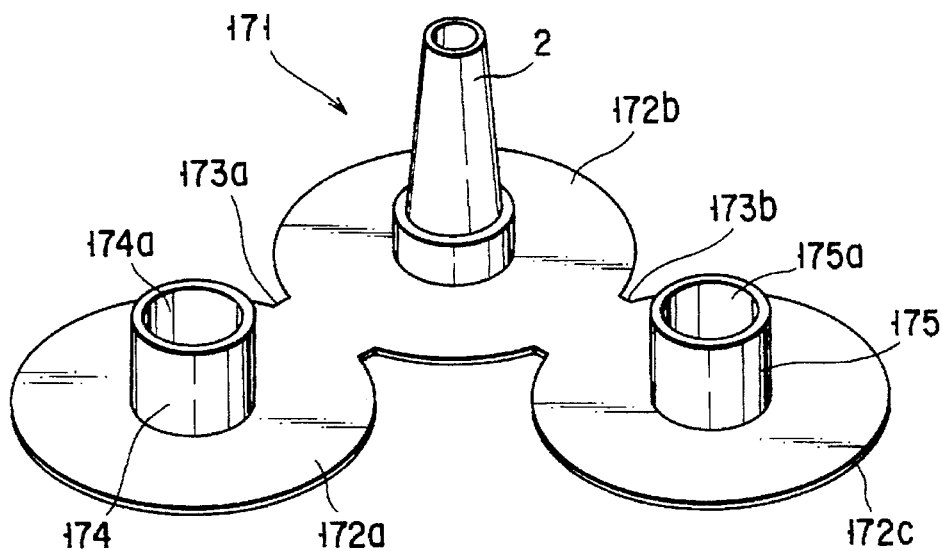
F I G. 39
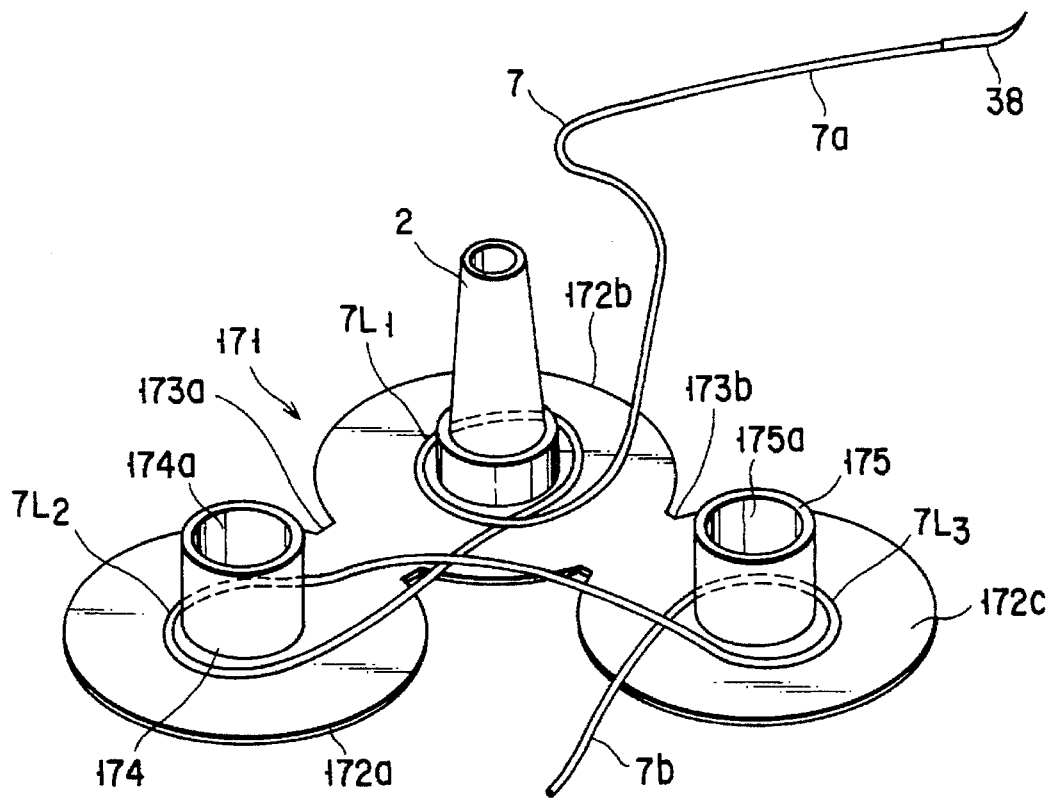
F I G. 40

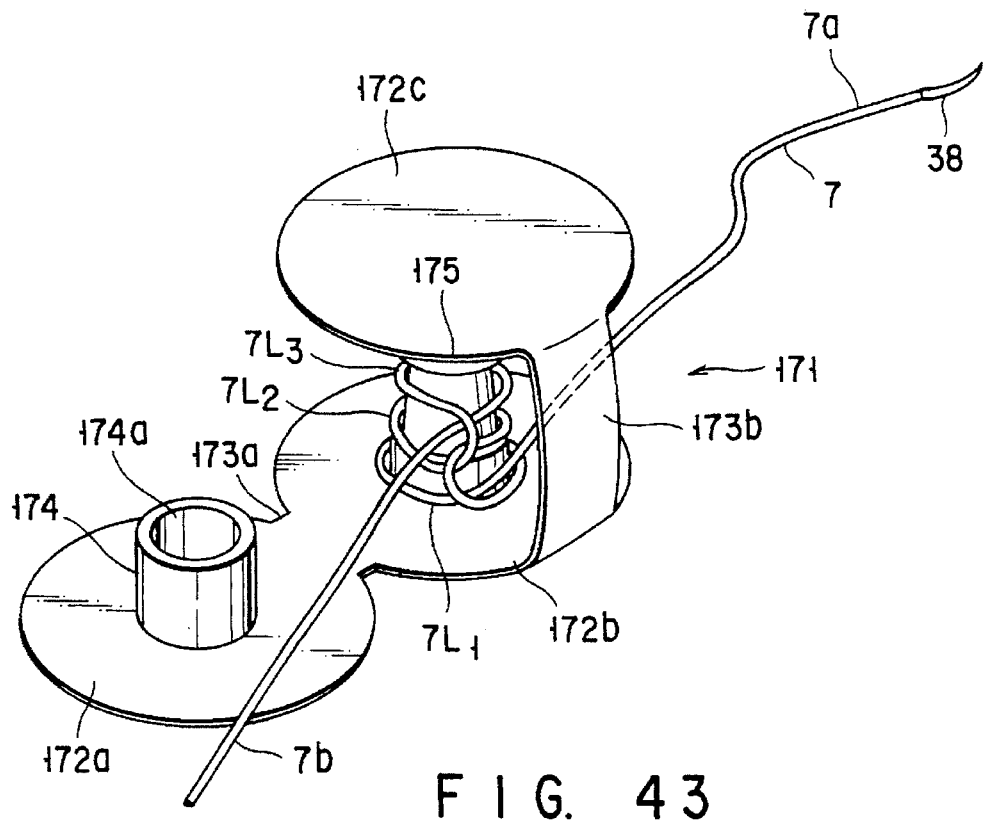
F I G. 43
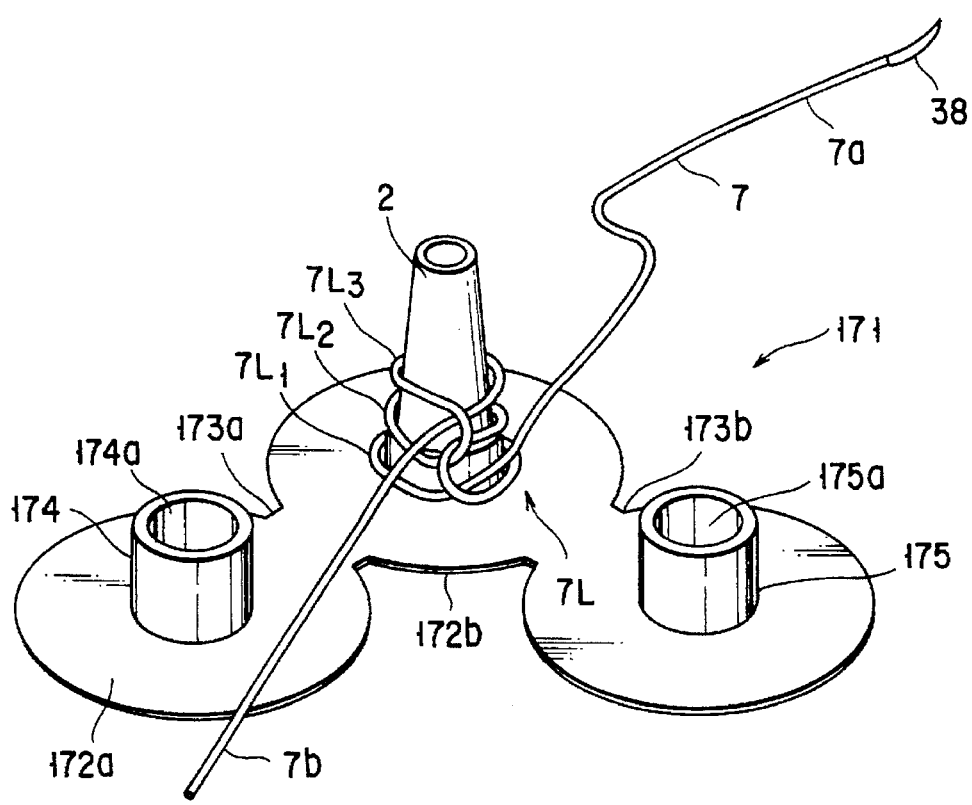
F I G. 44

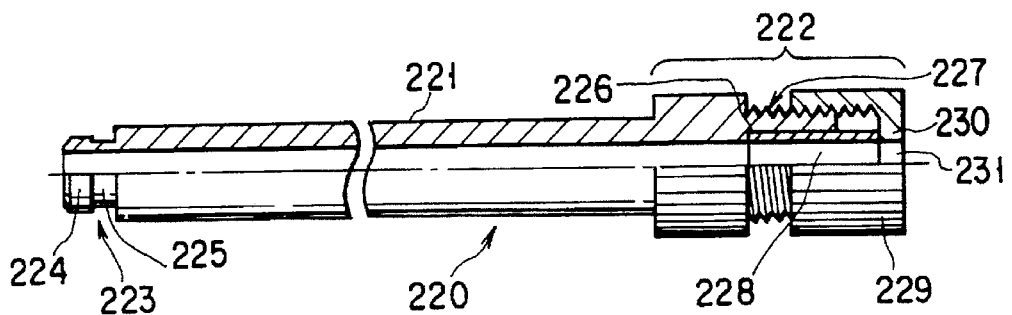
F I G. 51
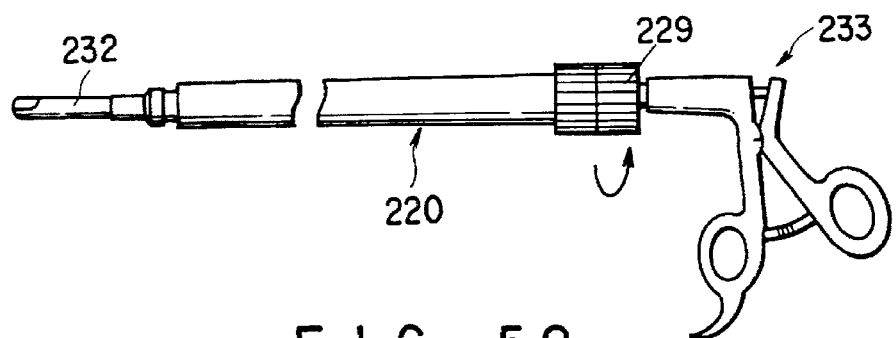
F I G. 52
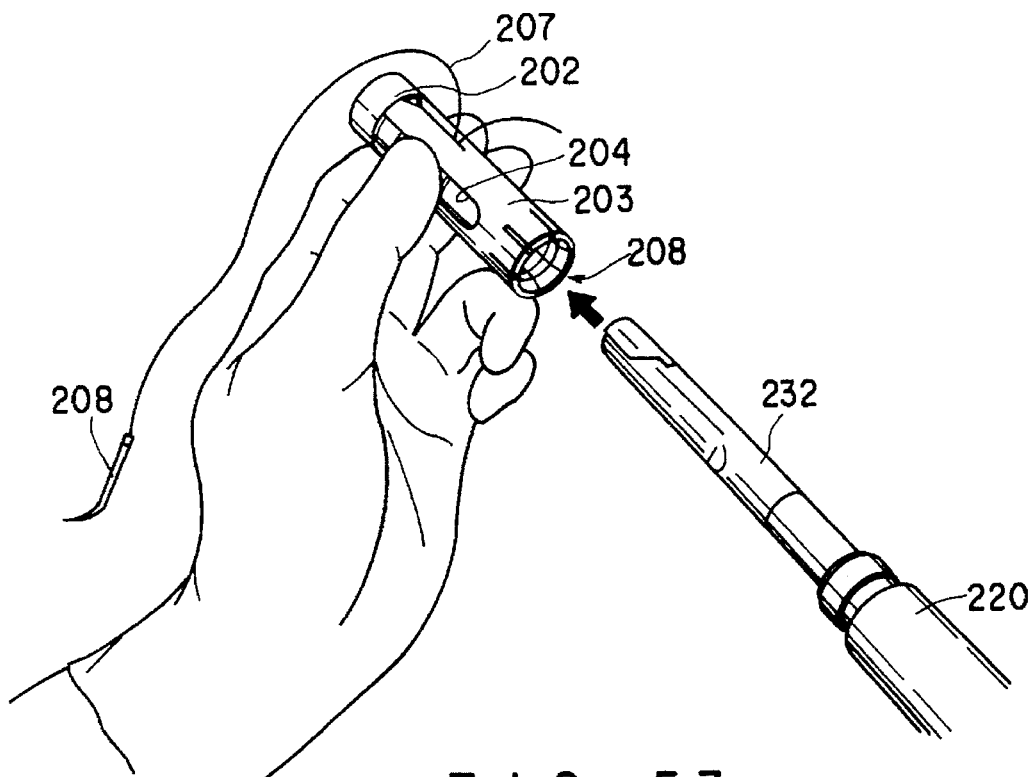
F I G. 53

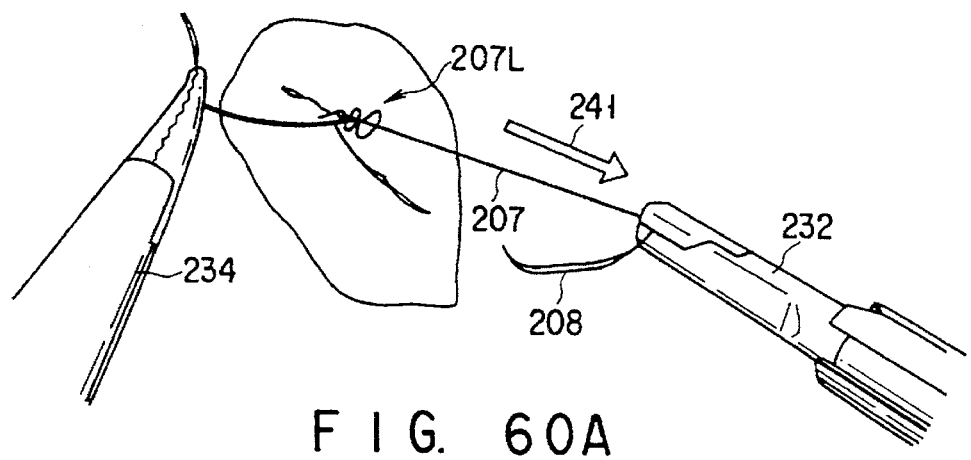
F I G. 60A
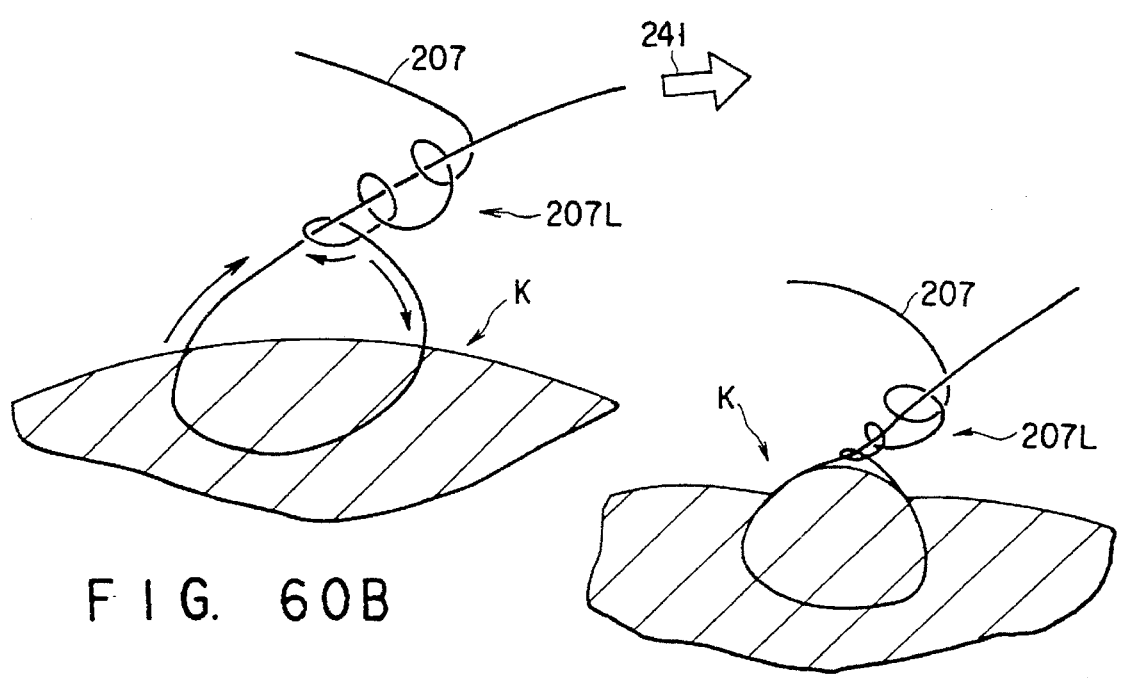
F I G. 60B
F I G. 60C
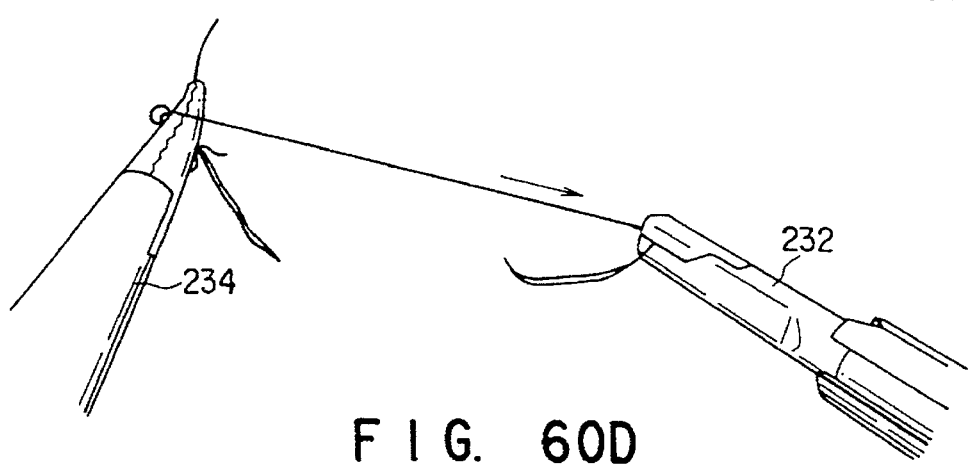
F I G. 60D

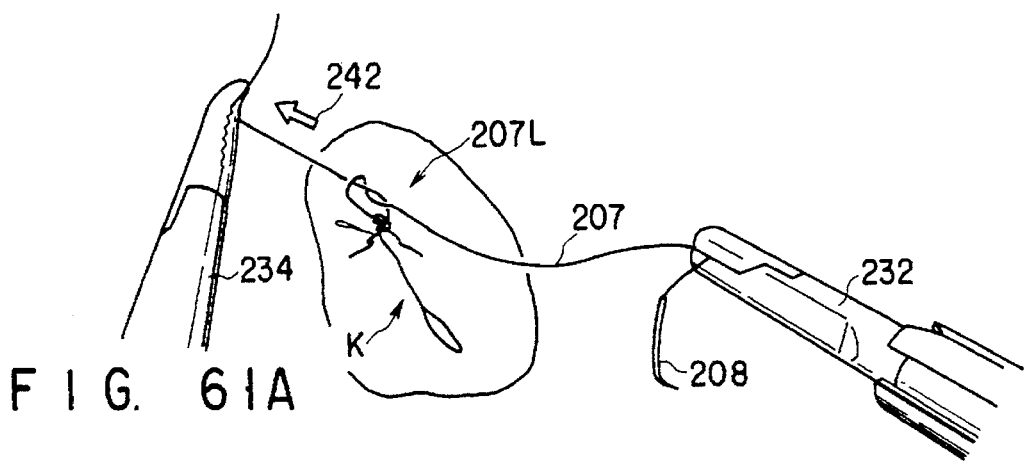
F I G. 61A
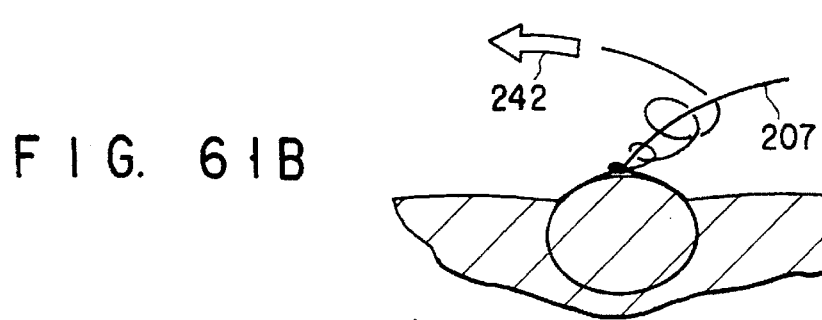
F I G. 61B
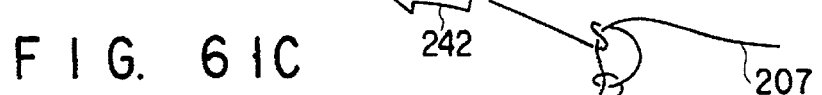
F I G. 61C
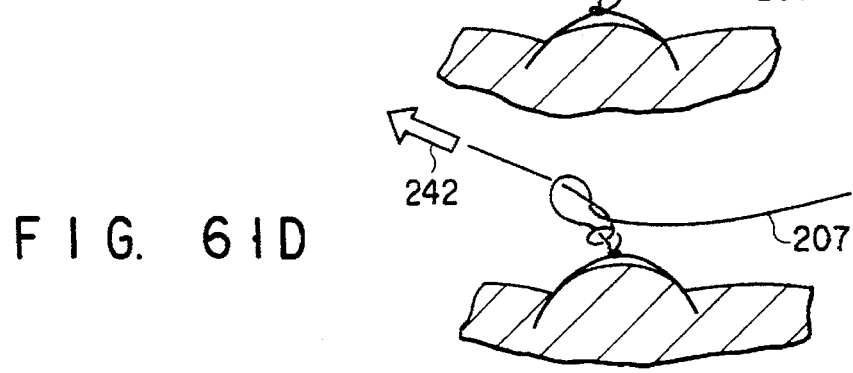
F I G. 61D
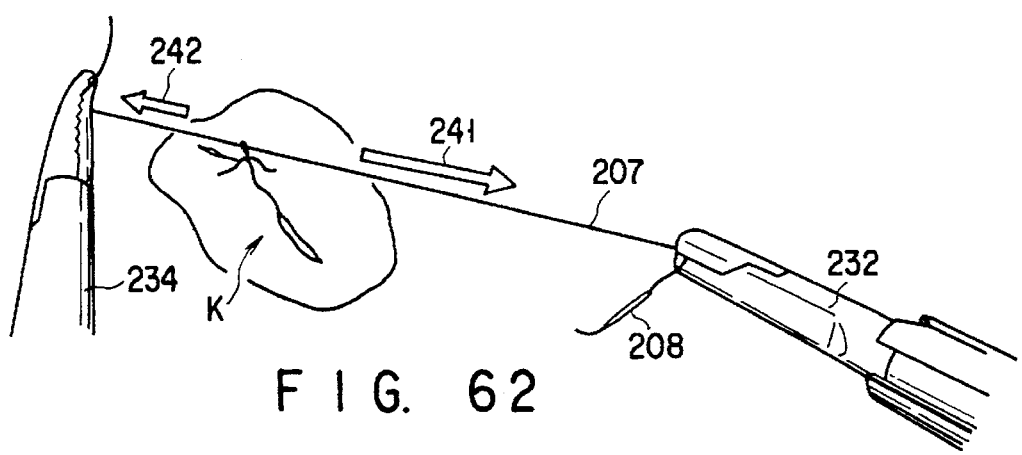
F I G. 62

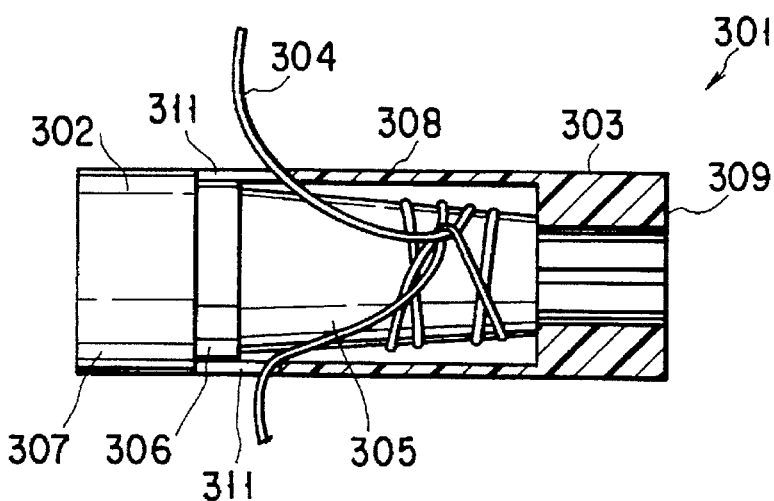
F I G. 63
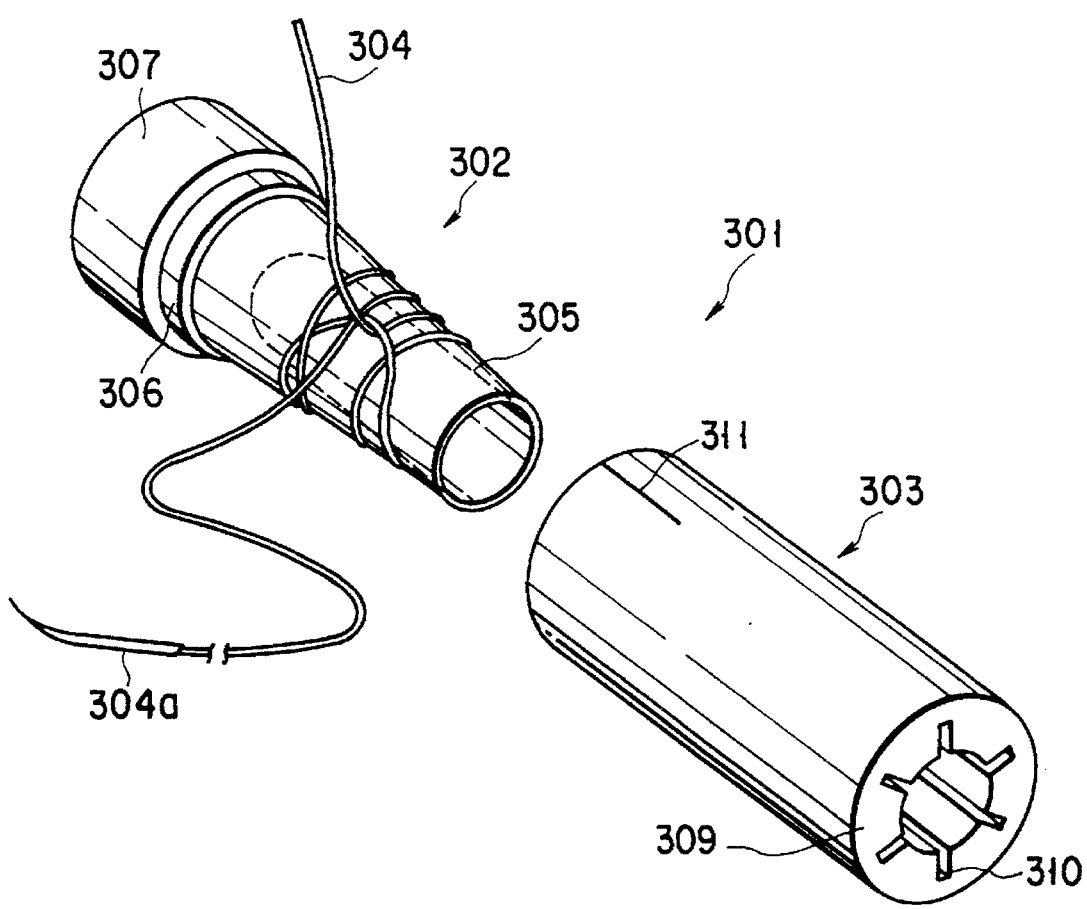
F I G. 64

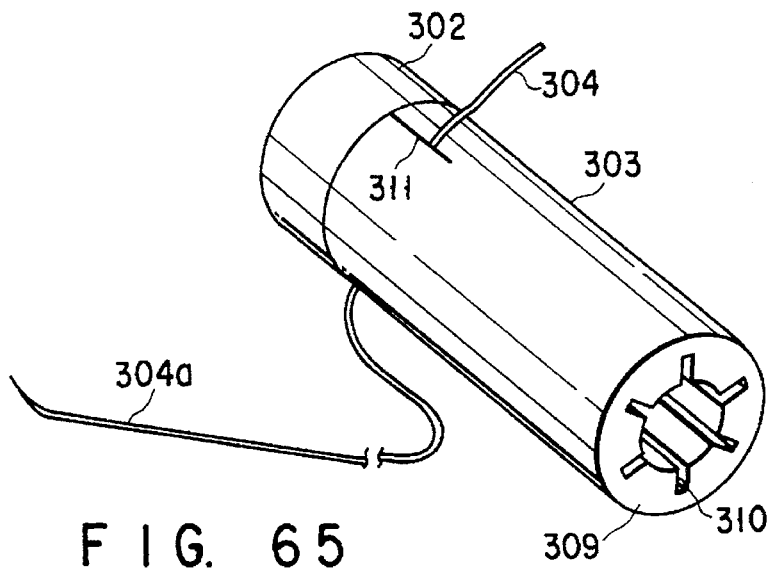
F I G. 65
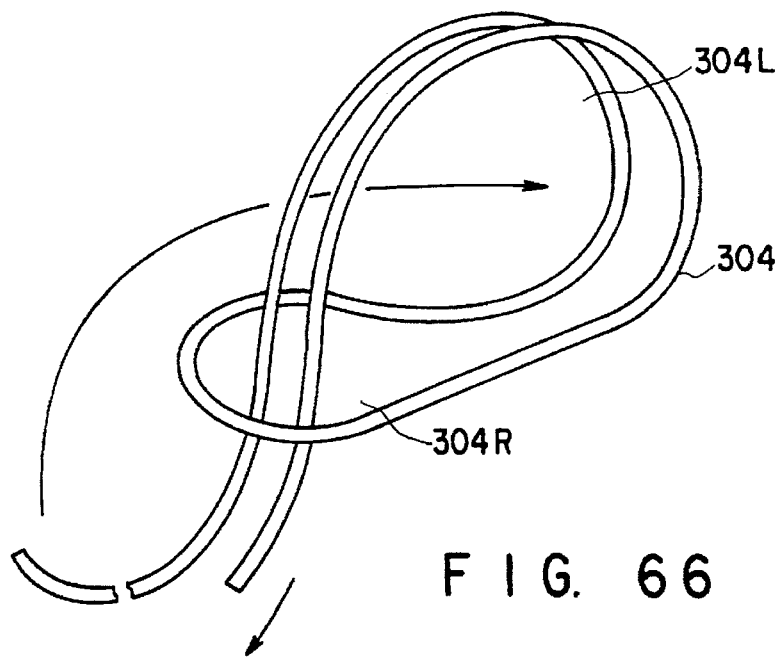
F I G. 66
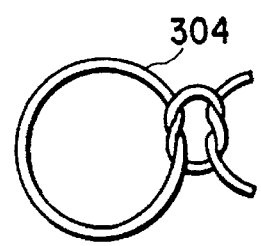
F I G. 67

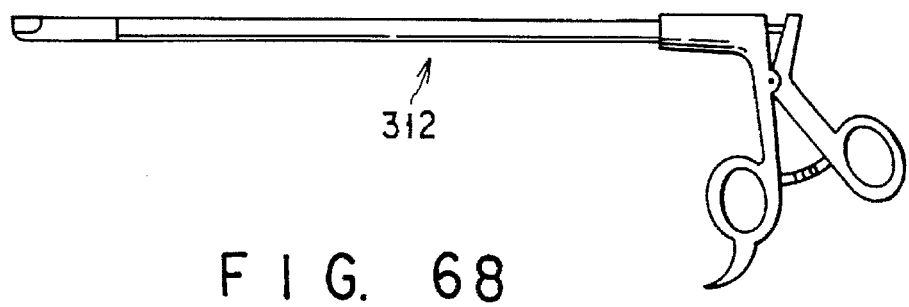
F I G. 68
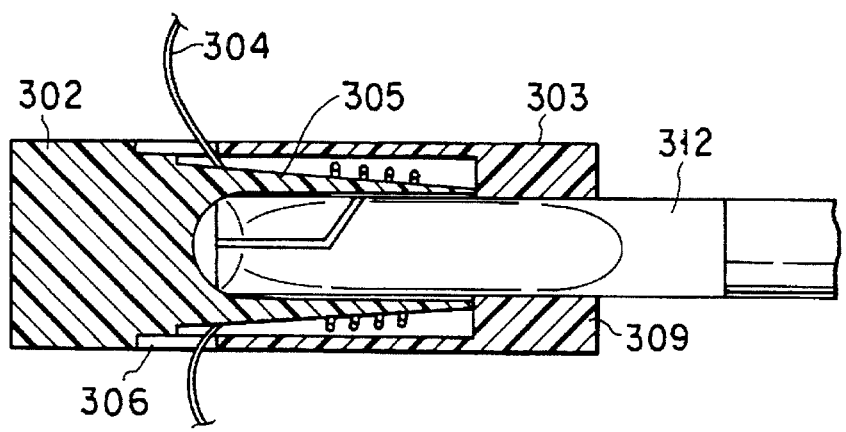
F I G. 69
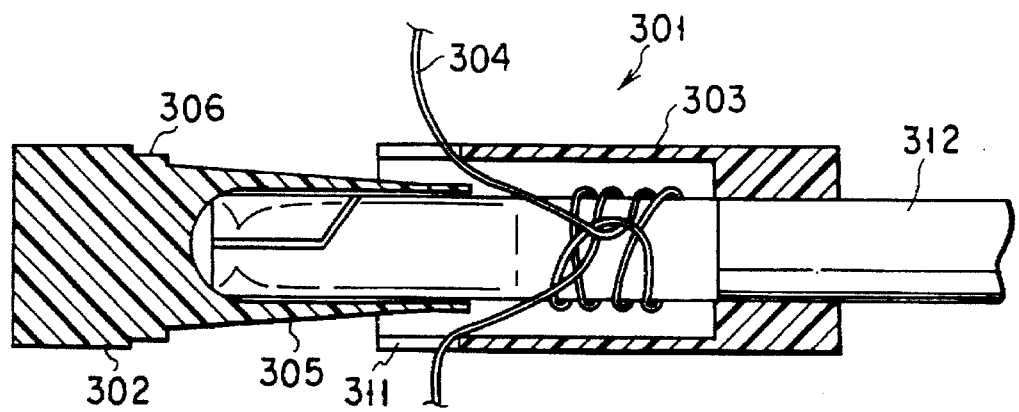
F I G. 70

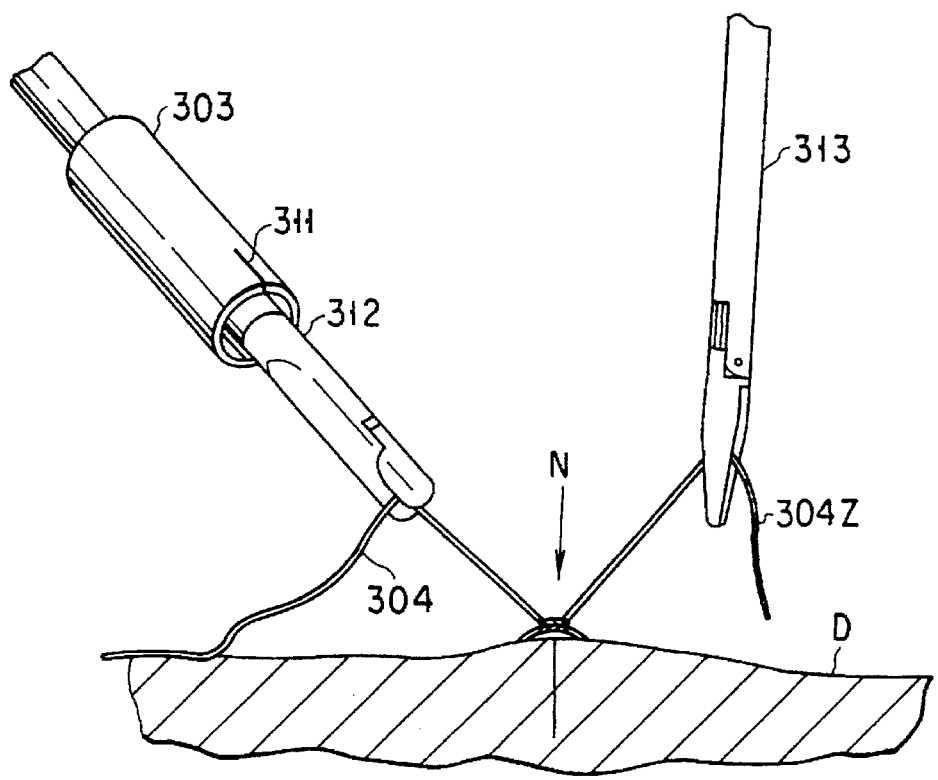
F I G. 74
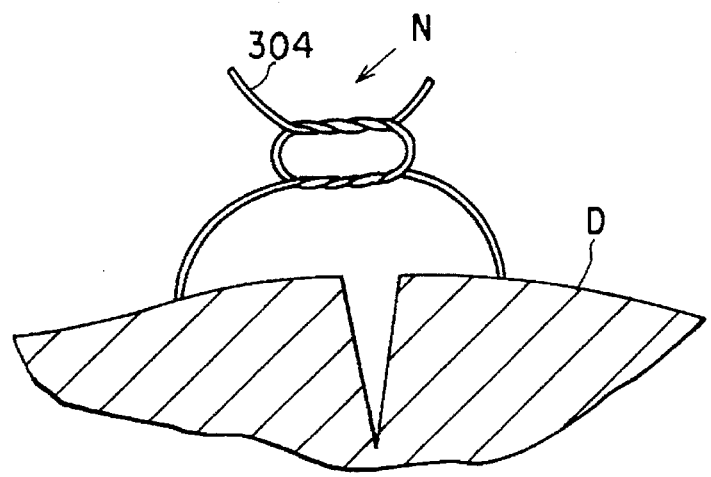
F I G. 75

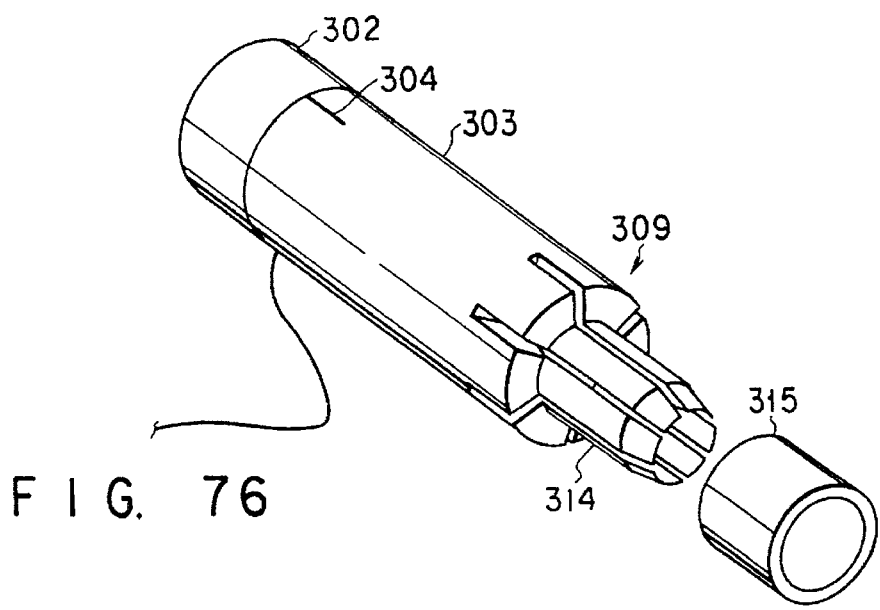
F I G. 76
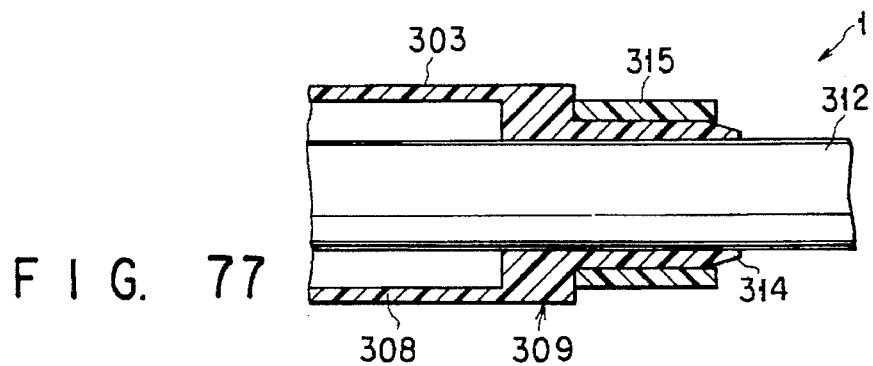
F I G. 77
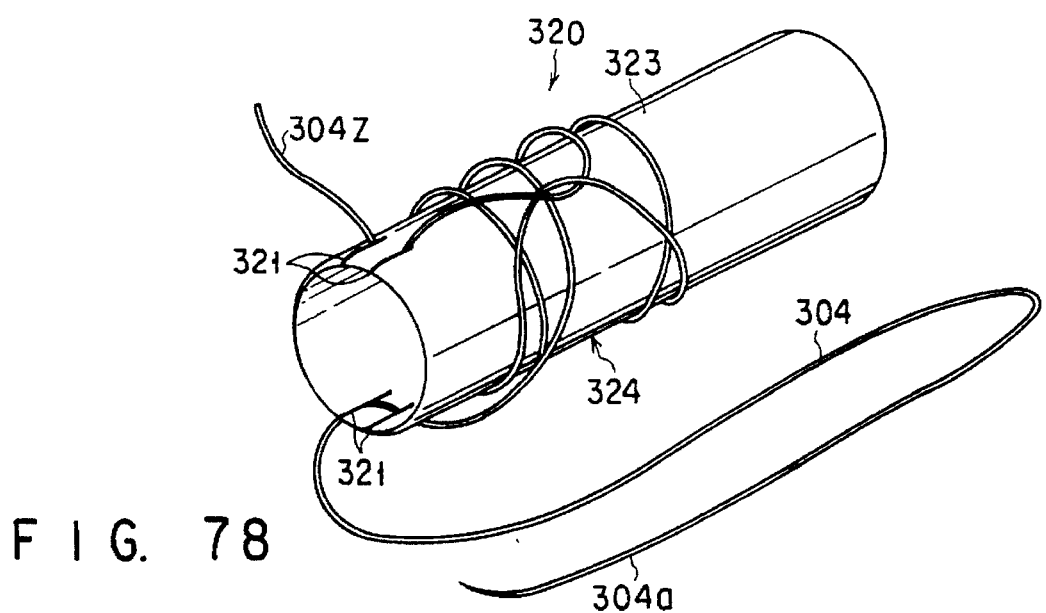
F I G. 78

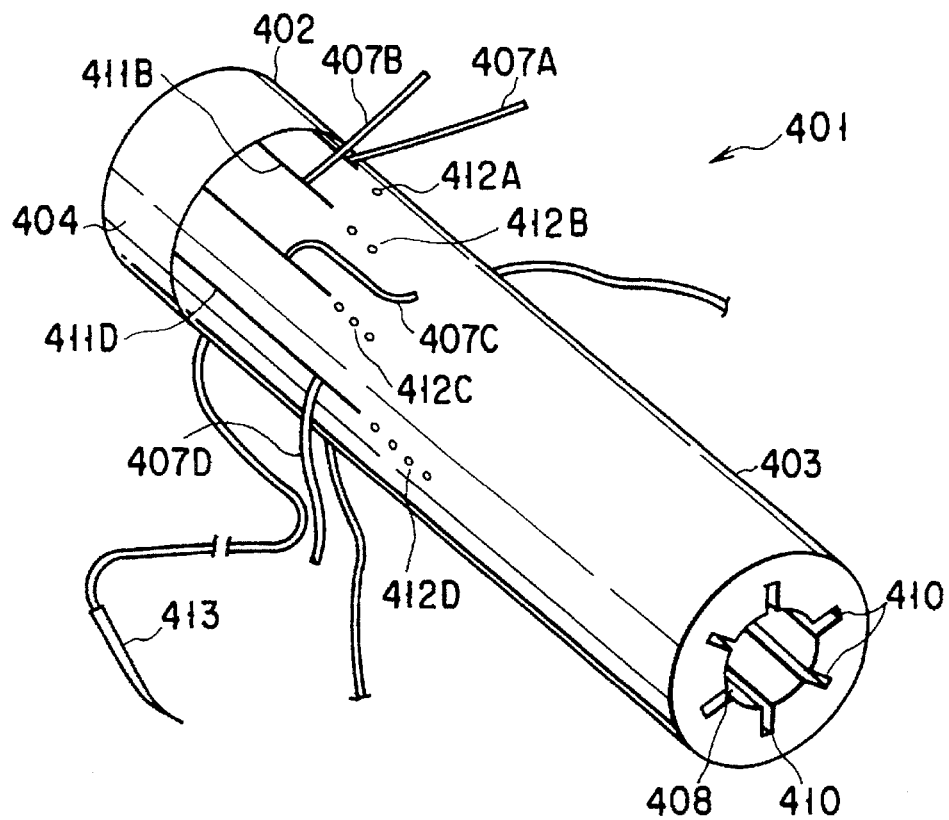
F I G. 83
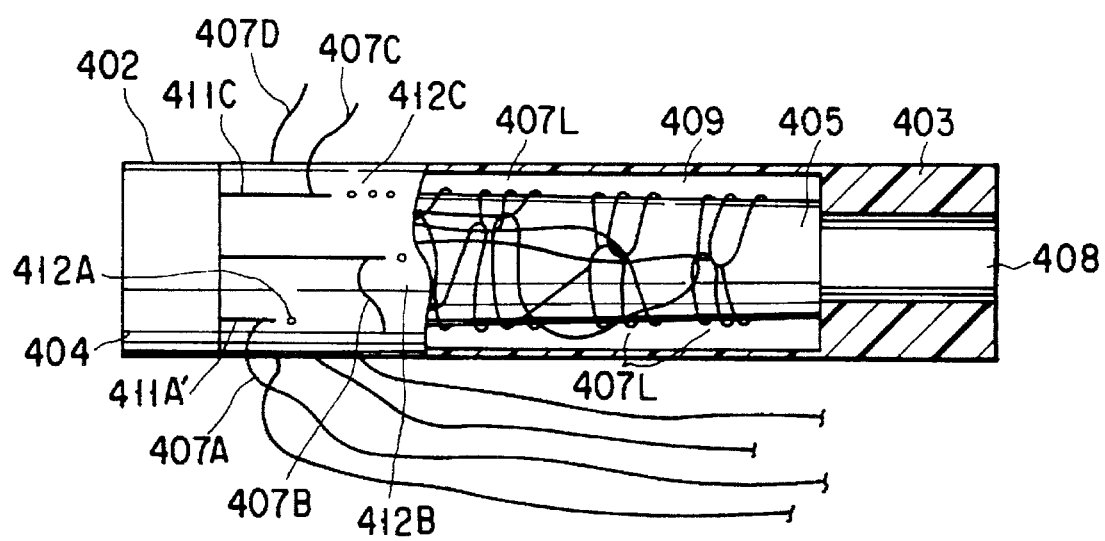
F I G. 84

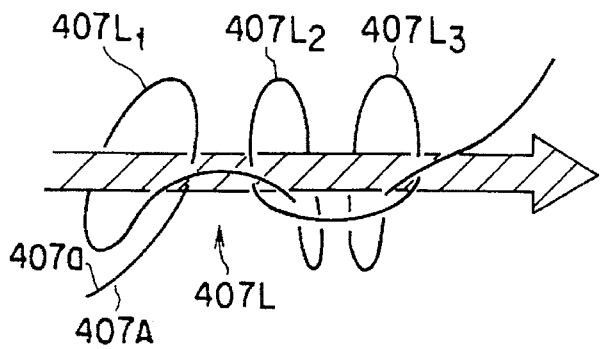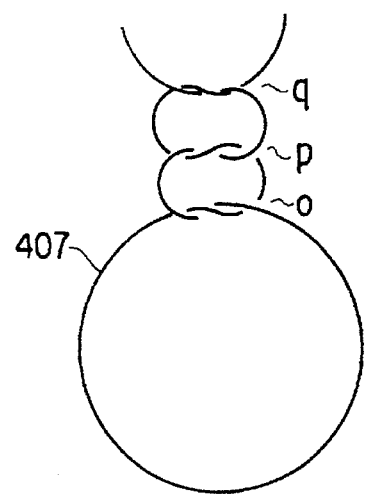
F I G. 88A  F I G. 88B
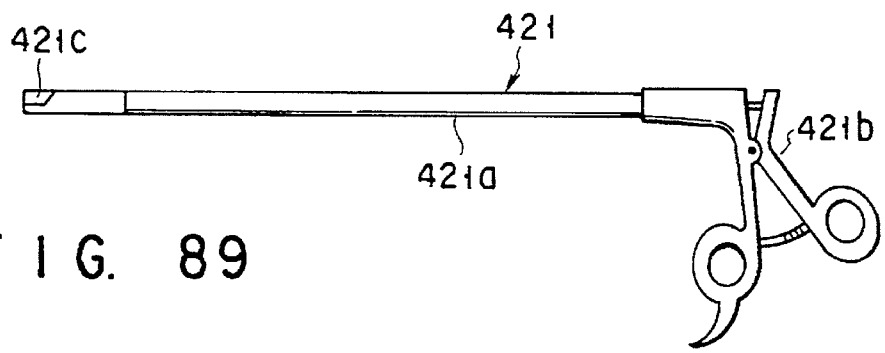
F I G. 89
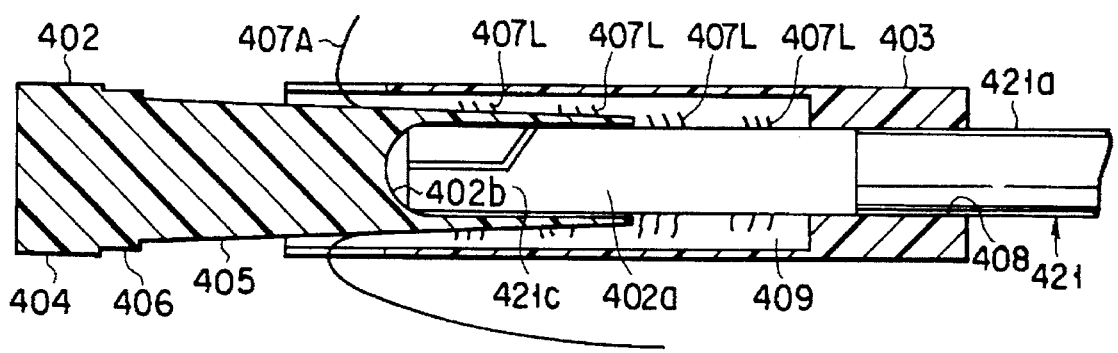
F I G. 90

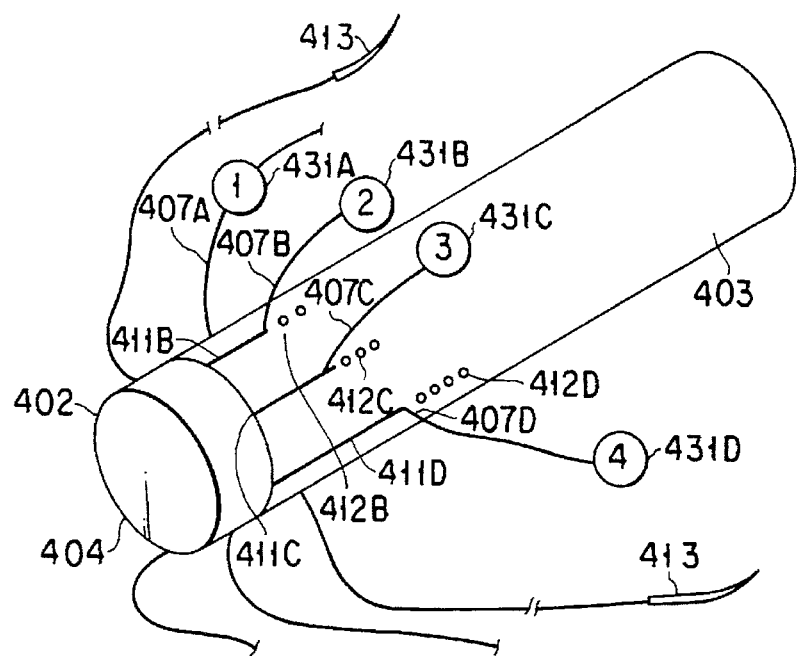
F I G. 95
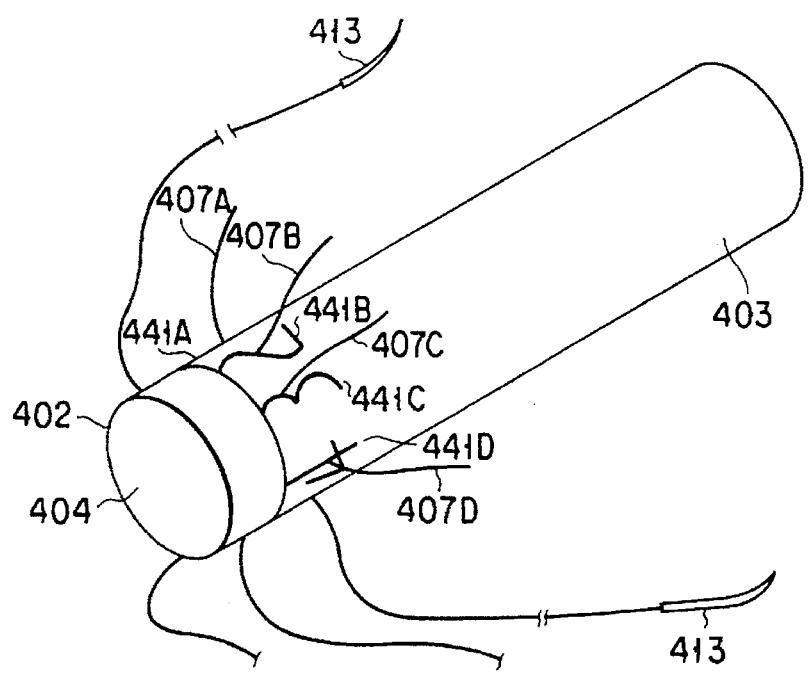
F I G. 96

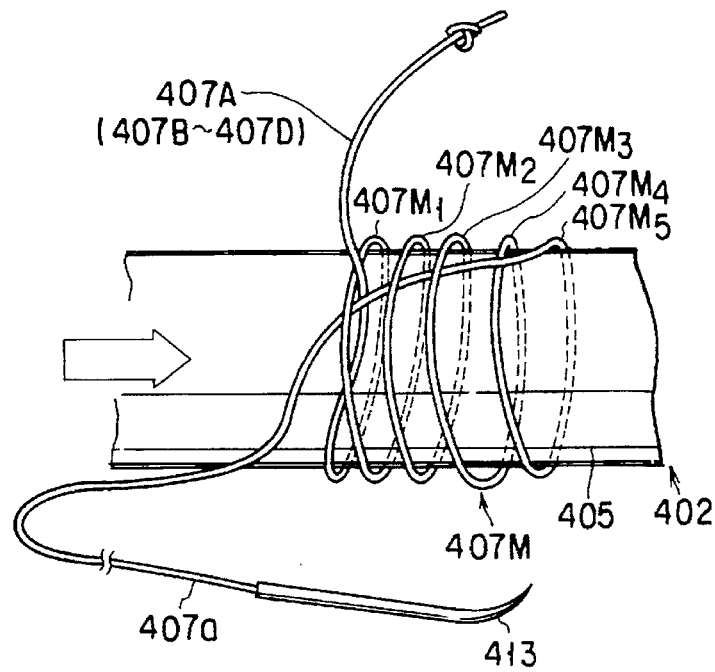
F I G. 97
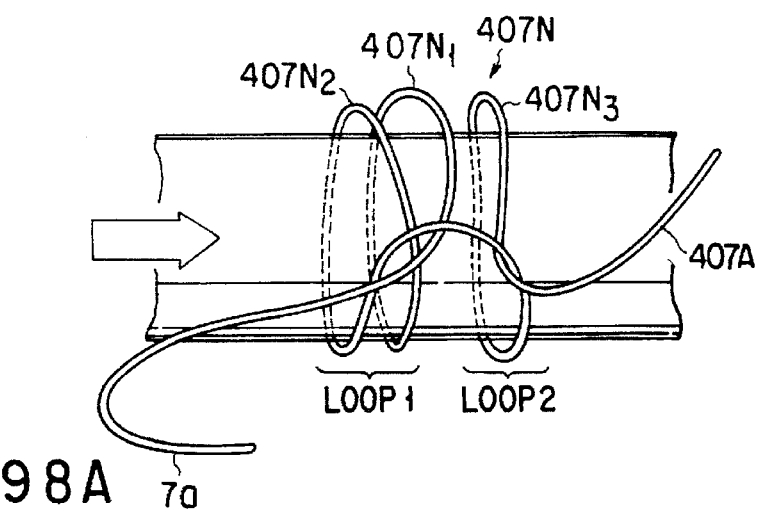
F I G. 98A
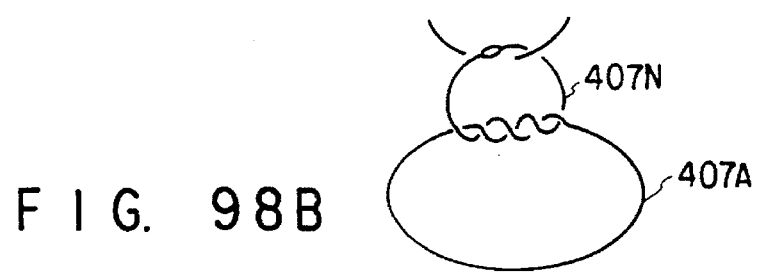
F I G. 98B

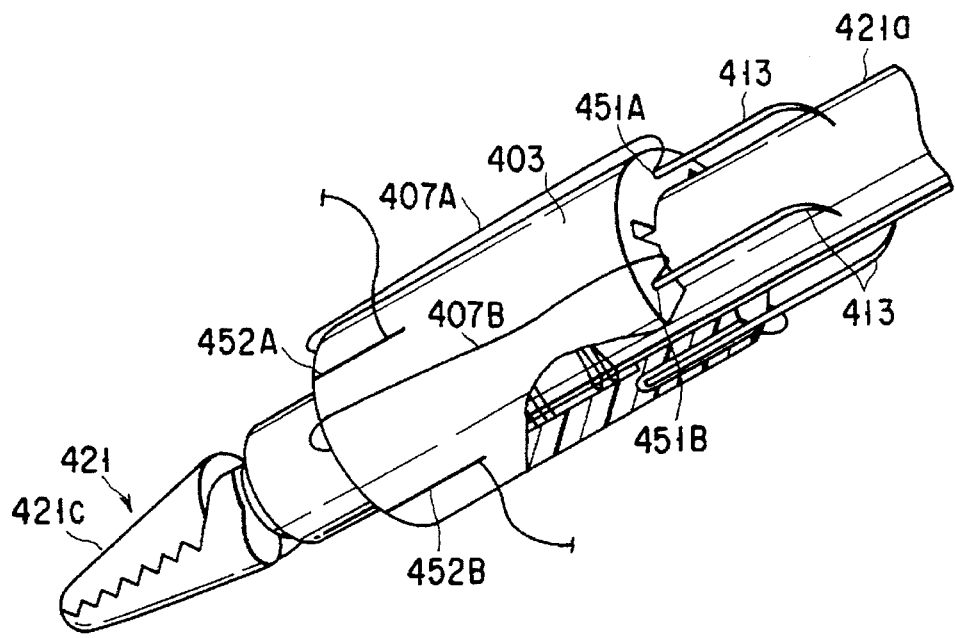
F I G. 106
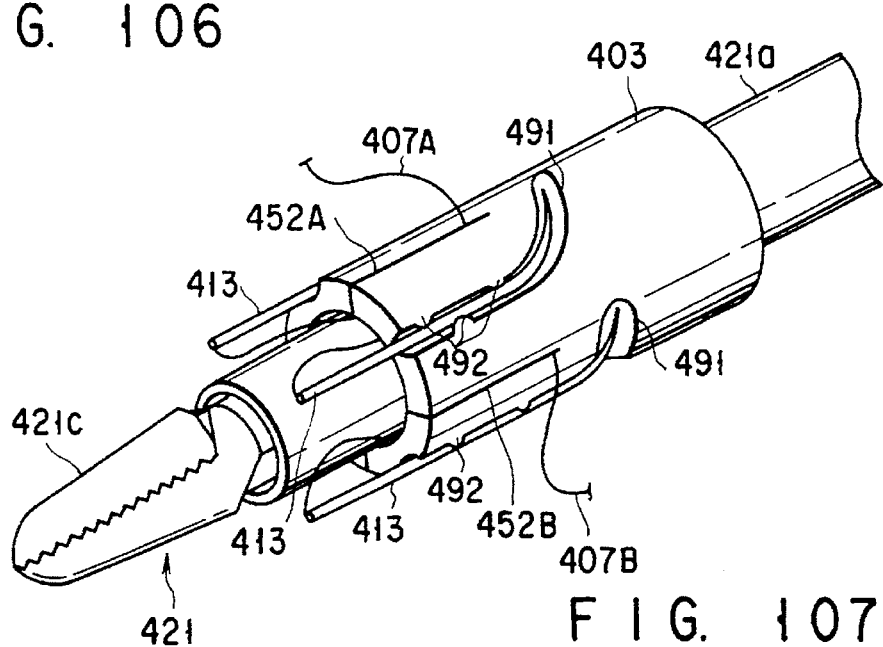
F I G. 107
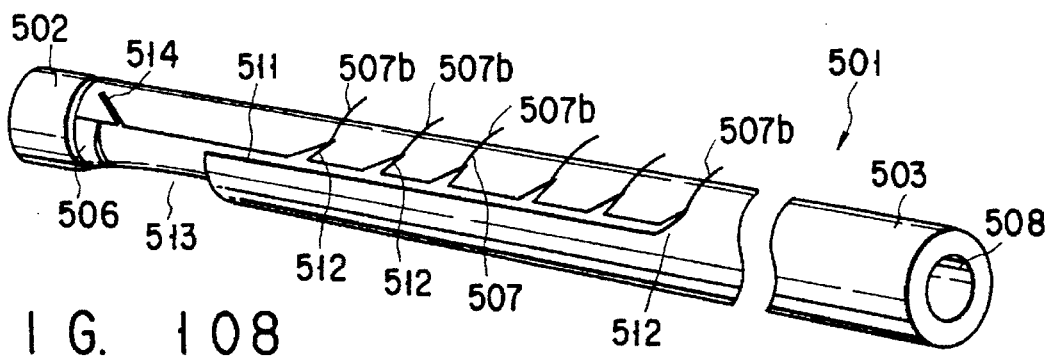
F I G. 108

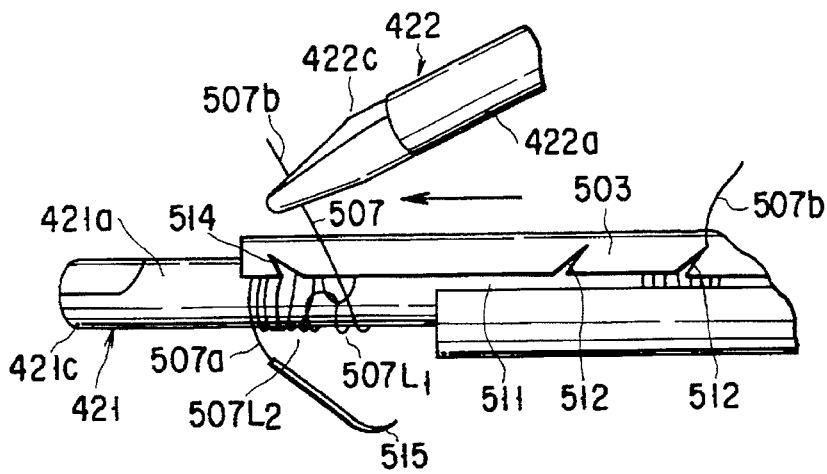
FIG. 112A
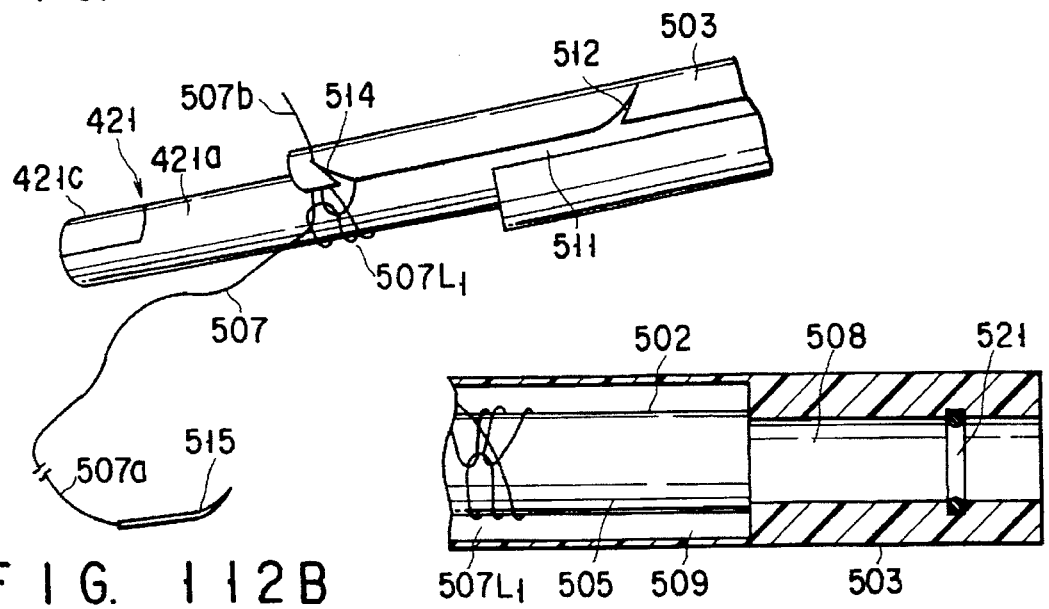
FIG. 112B
FIG. 113
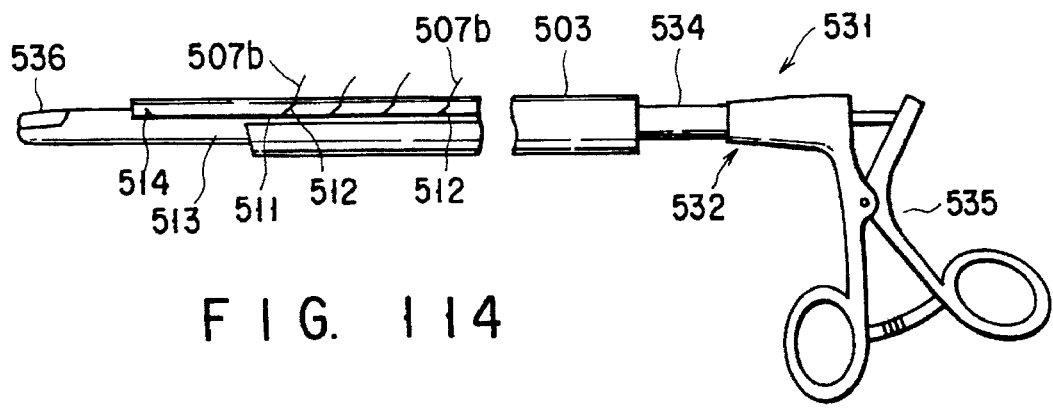
FIG. 114

SUTURING INSTRUMENT

BACKGROUND OF THE INVENTION

1. Field of the Invention

The present invention relates to a suturing instrument used for performing suture and/or ligature with a suture in a surgical operation while the interior of a body cavity is observed with an endoscope.

2. Description of the Related Art

In recent years, a surgical operation is often performed while observing the interior of the body cavity with an endoscope. When a special instrument must be operated within a body cavity, where movement of the instrument is limited, while observing a planar image sent from an endoscope with a monitor in this manner, it is very difficult to perform suture or ligature with a suture. For this reason, many instruments and methods are developed for performing ligation easily.

Transfixion suture methods that are currently generally performed are divided into an external ligation method and an internal ligation method. According to external ligation method, a suture is passed through a living body tissue in a body cavity. The two ends of the suture are extracted outside the body. A loose knot is formed on the suture outside the body. Then, this knot is fed into the body with a special instrument or the like that feeds the knot into the body.

U.S. Pat. No. 5,144,961 describes an instrument which ligates a suture in accordance with a method similar to that described above. According to this instrument, one end of a needle (end portion on a side to be remote from the needle) attached with a suture is wound on a hollow rod in advance, and a knot is formed on the hollow rod. Only a portion of the suture not wound on the rod and the needle are inserted into the body cavity. After suture, the suture is extracted outside the body. The suture is inserted through the inner hole of the hollow rod. The knot is removed from the rod, and the hollow rod is pushed in, thereby feeding the knot into the body cavity.

When the internal method is to be performed, square knot formation, or triple knot formation is performed by using two forceps for a laparoscopic operation in the same manner as in an ordinary abdominal operation. This ligation will be described later in detail.

A method of simplifying the operation of forming a knot in the body is disclosed in, e.g., U.S. Pat. No. 5,234,445. According to this method, a substantially lasso-like loop and a knot are formed midway along a suture attached with a needle, and the trailing portion of the suture following the loop and knot is passed through a hollow rod.

In this case, the knot is not located in the rod. The rod is inserted into the body cavity, the loop and the needle-attached suture attached to the distal end of the rod are inserted in the body cavity, and the target tissue is sutured while holding the needle with another forceps. Then, after the forceps is passed through the loop, the needle-side portion of the suture is held, and the needle-side portion of the suture is pulled to pass through the loop. Simultaneously, the hollow rod is pushed to feed the knot. Thus, the substantially lasso-like loop is closed, thereby forming a knot.

According to the method of performing ligation by using the two forceps in the body cavity, for example, the instruments to be used are forceps for a laparoscopic operation. Two forceps of this type are operated to perform square knot formation or triple knot formation as in an ordinary abdominal operation as described above.

According to an example of the procedure of above ligation, one end of the suture is picked up by the first forceps, and the suture is wound on the circumferential portion of the second forceps. Subsequently, the first forceps holding the one end of the suture is maintained in the suture-holding state, and the other end of the suture is gripped by the second forceps on which the suture is wound.

The first forceps is moved toward the distal end of the second forceps to bring the ring of the wound suture above the other end of the suture over the second forceps. In this state, the first and second forceps are pulled in the opposite directions to close the ring of the wound suture, thereby forming a knot.

Square knot formation or triple knot formation can be performed by repeating the above operation twice or three times while reversing the winding direction each time. When square knot formation is performed, a knot as shown in FIG. 5B can be obtained.

The knot obtained in this manner is stiff and firm. The suture can be reliably fastened by pulling the two ends of the suture with the two forceps horizontally in the opposite directions with respect to the knot as the center. The fastening degree and the like can be easily adjusted by forming a knot in this manner.

According to the conventional methods, however, when a knot is to be formed outside the body, since the two ends of the suture guided into the body must be extracted outside the body, the forceps must be inserted into and extracted from the body many times, leading to a cumbersome operation.

Since the two ends of the suture are extracted outside the body, the suture must be very long. Then, when the suture is pulled outside the body, the living body tissue through which the suture extends can be rubbed with the suture for a long period of time. Furthermore, a special instrument is required for feeding the knot into the body, leading to an increase in cost. Moreover, in the method of feeding an external knot into the body, it is sometimes difficult to firmly fasten the knot.

Since ligation performed in the body by using two forceps for a laparoscopic operation must be performed under a specific circumstance as described above, it is very difficult to operate the forceps as in an ordinary abdominal operation. In particular, it is difficult to wind the suture on the forceps, thus requiring techniques and skills.

In the method of forming a knot by fastening the other end of a suture with the substantially lasso-like loop, since the knot is comparatively loose, it may be untied. When, e.g., a substantially lasso-like loop is attached to the distal end of a rod and the rod is inserted into the body cavity, in addition to formation of two holes that must be formed in the patient's body surface to allow insertion of two forceps that perform ordinary suture, another hole must be formed in the patient's body surface to allow insertion of the rod, thereby increasing load to the patient.

SUMMARY OF THE INVENTION

The present invention has been made in view of the above situations, and has as its object to provide a suturing instrument that can reliably and firmly form a knot in the body cavity with a simple operation, thus suturing a tissue to be sufficiently cured, can decrease the number of times of inserting/extracting a treatment instrument, e.g., a forceps, into/from the body cavity during suture without increasing the number of treatment instruments, and can be used without using a special ligating instrument but together with several types of treatment instruments that are generally used.

According to an aspect of the present invention, there is provided a medical instrument for performing at least one of suture and ligation to form a suitable knot in a piece of suture within a body cavity, the suture having a first end portion, a second end portion, and at least one loop formed in advance at an intermediate portion between the first and second end portions to have a predetermined size, and suitable for application to a body tissue, comprising holding means for holding the loop to almost maintain the size thereof, fastening means, provided to the holding means, for fastening at least one portion of the suture, and an inserting instrument which is to be inserted into the body, which has a distal end portion that can be arranged in the body cavity, and an operating portion, arranged outside the body, for operating the distal end portion thereof, and on which the holding means that holds the suture is mounted, the distal end portion projecting beyond the loop held by the holding means, the distal end portion having gripping means capable of gripping the suture, wherein the inserting instrument causes the first end portion of the suture gripped near an insertion port to the body cavity and in the body cavity to pass through the loop, thereby forming a knot.

Regarding the loop of the suture for the body tissue, at least one loop is formed on part of the suture for performing, e.g., ligation, and is held by the holding means. The extending portion of the suture extending from this loop, or part of the suture is fastened by the fastening means of the holding member. The inserting instrument mounted in the holding means attached with the suture is inserted into the body cavity, and the holding member, or the loop accordingly, is arranged near a portion in the body cavity that requires suture or ligation. Thereafter, the end portion of the suture applied to the required portion is held by the gripping means of the inserting instrument, and is caused to pass through the loop. Then, the diameter of the loop is reduced, thereby forming a knot.

Therefore, according to the present invention, a knot can be reliably and firmly formed in the body cavity with a simple operation, thus suturing a tissue to be sufficiently cured. At the same time, the number of times of inserting/extracting the treatment instrument, e.g., a forceps, into/from the body cavity during suture can be decreased without increasing the number of the treatment instrument, thus decreasing load to the patient.

According to another aspect of the present invention, there is provided a transfixion suture instrument for forming a suitable knot with a piece of suture in a body cavity with a surgical instrument having a distal end portion and an operating portion, the suture having a first end portion, a second end portion, and at least one loop formed in advance at an intermediate portion between the first and second end portions to have a predetermined size, and suitable for application to a body tissue, comprising holding means for holding the loop to almost maintain a size thereof, the holding means having locking means for locking at least one portion of the suture excluding the loop, and arranging means for arranging the holding means at the distal end portion of the surgical instrument so that the surgical instrument is inserted into the body cavity together with the loop held by the holding means.

In addition to the above advantages, this instrument can be used without using a special ligation instrument but together with several types of treatment instruments that are generally used.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIGS. 14A and 14B show the third modification of the first embodiment, in which FIG. 14A is a perspective view showing a wound state of the suture, and FIG. 14B is a schematic view showing how to wind a suture to form a knot called as surgeon' knot;

FIGS. 18A and 18B show the seventh modification of the first embodiment, in which FIG. 18A is a perspective view showing the arrangement of the main part of a suture holding member, and FIG. 18B is a perspective view showing the main part of the state of use of the suture holding member;

FIG. 21 is a longitudinal sectional view showing the arrangement of the main part of the suture holding member according to the ninth modification of the first embodiment;

FIG. 22 is a longitudinal sectional view of a suture holding member according to the tenth modification of the first embodiment;

FIG. 23 is a longitudinal sectional view of a suture holding member according to the eleventh modification of the first embodiment;

FIGS. 24A and 24B show the twelfth modification of the first embodiment, in which FIG. 24A is a perspective view showing a state wherein a suture holding member is used in combination with a trocar, and FIG. 24B is a perspective view showing a state wherein a forceps used in combination with the suture holding member shown in FIG. 24A is inserted into the trocar;

FIGS. 31A to 31D show the third embodiment of the present invention, in which FIG. 31A is a perspective view showing a film unit, FIG. 31B is a perspective view showing a state wherein a forceps is pushed out from the interior of the forceps insertion port of the film unit to separate a needle, and the suture is pulled out, FIG. 31C is an exploded perspective view of the film unit, and FIG. 31D is a perspective view showing a state wherein the film unit and the forceps are inserted into the patient's body cavity through a trocar;

FIG. 32 is a longitudinal sectional view showing the first modification of the suturing instrument;

FIG. 33A is a longitudinal sectional view showing a state wherein the movable valve of a trocar is closed, and FIG. 33B is a longitudinal sectional view showing a state wherein a forceps is inserted into the trocar, thus opening the movable valve;

FIG. 34A is a longitudinal sectional view showing a state wherein a forceps is attached with a suturing instrument and is inserted into the trocar, and FIG. 34B is a longitudinal sectional view showing a state wherein the suturing instrument main body and a reducer are separated;

FIG. 35 is a longitudinal sectional view showing the first modification of the suturing instrument shown in FIG. 32;

FIG. 36 is a longitudinal sectional view showing the second modification of the suturing instrument shown in FIG. 32;

FIGS. 37A and 37B show the second modification of the suturing instrument, in which FIG. 37A is a perspective view showing the schematic arrangement of the entire suturing instrument, and FIG. 37B is a perspective view showing the arrangement of the main part of the suturing instrument;

FIGS. 38A and 38B show the third modification of the suturing instrument, in which FIG. 38A is a perspective view showing the schematic arrangement of the entire suturing instrument, and FIG. 38B is a perspective view showing the state of use of the suturing instrument;

FIG. 39 is a perspective view showing a suture winding unit of the suturing instrument;

FIG. 40 is a perspective view showing a state wherein a suture is wound on the suture winding unit;

FIG. 43 is a perspective view showing a state wherein the second cylinder is fitted on the inner cylinder to move the third loop to the inner cylinder;

FIG. 44 is a perspective view showing a state wherein the second cylinder is restored to the original position;

FIG. 51 is a partially sectional view of an adaptor for attaching the outer cylinder shown in FIG. 49 to the forceps;

FIG. 52 is a side view of a state wherein the adaptor shown in FIG. 51 is attached to the forceps;

FIG. 53 is a perspective view showing a state wherein the suture holding member shown in FIG. 49 is attached to the forceps;

FIGS. 60A to 60D are explanatory views sequentially showing states wherein the end portion of the needle on its suture side that has passed through the loop is pulled to fasten a body tissue with the suture;

FIGS. 61A to 61D are explanatory views sequentially showing states wherein the end portion of the suture on its side opposite to that shown in FIGS. 60A to 60D is pulled to reduce the loop of the suture;

FIG. 62 is an explanatory view showing a state wherein the loop of the suture is pulled from the two ends to form a knot; FIG. 63 is a side sectional view of a suturing instrument according to the fifth embodiment of the present invention;

FIG. 64 is a partially exploded view of the suturing instrument shown in FIG. 63;

FIG. 65 is a perspective view of the suturing instrument shown in FIG. 63;

FIG. 66 is an explanatory view of a loop formed on a suture used in the embodiment shown in FIG. 63;

FIG. 67 is an explanatory view of a knot formed from the loop shown in FIG. 66;

FIG. 68 is a schematic view of a forceps on which the suturing instrument shown in FIG. 63 is to be mounted;

FIG. 69 is an explanatory view of a state wherein the suturing instrument shown in FIG. 63 is mounted on the distal end portion of a forceps;

FIG. 70 is an explanatory view of a state wherein an inner cylinder is removed in the state shown in FIG. 69 and a suture is mounted on the forceps;

FIG. 74 is an explanatory view of a state wherein the suture is pulled to perform ligation;

FIG. 75 is an explanatory view of a knot that ligates body tissues;

FIG. 76 is a perspective view of a suturing instrument according to a modification of the fifth embodiment;

FIG. 77 is a schematic sectional view of the suturing instrument shown in FIG. 76;

FIG. 78 is a perspective view of a suturing instrument according to the sixth embodiment;

FIG. 83 is a perspective view showing a suture holding member according to the eighth embodiment of the present invention;

FIG. 84 is a partially cutaway side view of the suture holding member according to the EIGHT embodiment;

FIG. 88A is a schematic view showing a state wherein a one end of the suture is passed through the first to third three loops, and FIG. 88B is a schematic view showing a state wherein the suture forms a triple knot formation;

FIG. 89 is a side view schematically showing the arrangement of the forceps;

FIG. 90 is a longitudinal sectional view showing a state wherein the first forceps is inserted into the body cavity of the forceps fixing portion at the rear end of the outer cylinder to push out the inner cylinder from the outer cylinder;

FIG. 95 is a perspective view showing a suture holding member according to the first modification of the eighth embodiment;

FIG. 96 is a perspective view showing a suture holding member according to the second modification of the eighth embodiment;

FIG. 97 is a perspective view of a wound state of the suture according to the third modification of the eighth embodiment;

FIGS. 98A and 98B show the fourth modification of the eighth embodiment, in which FIG. 98A is a perspective view showing the wound state of the suture, and FIG. 98B is a schematic view showing how to wind the suture to form a surgeon' knot;

FIGS. 99A and 99B show the ninth embodiment of the present invention, in which FIG. 99A is a perspective view showing a suture holding member, and FIG. 99B is an exploded perspective view showing a state before the inner cylinder of the suture holding member is inserted into the outer cylinder;

FIGS. 104A and 104B show the second modification of the ninth embodiment, in which FIG. 104A is a partially cutaway perspective view showing the arrangement of the main part of the suture holding member, and FIG. 104B is a perspective view showing a state wherein the distal end portion of the outer cylinder is caused to project outside the sheath;

FIG. 106 is a perspective view showing a suture holding member according to the fourth modification of the ninth embodiment;

FIG. 107 is a perspective view showing a suture holding member according to the fifth modification of the ninth embodiment;

FIG. 108 is a perspective view showing a suture holding member according to the tenth embodiment of the present invention;

FIG. 112A is a side view showing a state wherein the B end portion of the first suture, when counted from the distal end of the outer cylinder, is gripped by the second forceps and is removed from the suture gripping groove, and FIG. 112B is a side view showing a state wherein the loop portion is slid toward the distal end by the second forceps and the B end portion of the suture is caught by the suture fixing groove so as to be held in it;

FIG. 113 is a perspective view showing the arrangement of the main part of the first modification of the tenth embodiment; and FIG. 114 is a perspective view showing a suturing instrument according to the eleventh embodiment of the present invention.

DETAILED DESCRIPTION OF THE PREFERRED EMBODIMENTS

Figure 1:
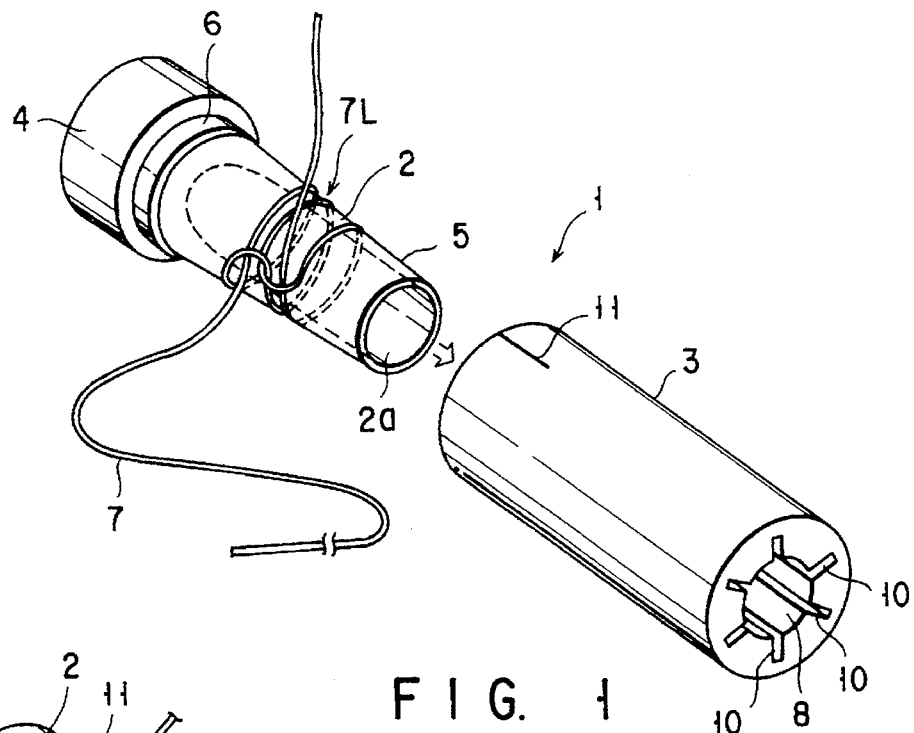
FIG. 1 is a perspective view showing a suture holding member according to the first embodiment of the present invention.

The first embodiment of the present invention will be described with reference to FIGS. 1 to 10. FIG. 1 schematically shows the arrangement of a suture holding member 1 of a suturing/ligaturing instrument used for medical operation. The suture holding member 1 is provided with an inner cylinder 2 and an outer cylinder 3 detachably connected to the inner cylinder 2.

The inner and outer cylinders 2 and 3 are made of deformable elastic members. To form the elastic members, e.g., a rubber material (silicone rubber, fluororubber, nitryl rubber, and the like), a plastic material (fluoroplastic, polyethylene, vinyl chloride, and the like), and the like are used.

Figure 3:
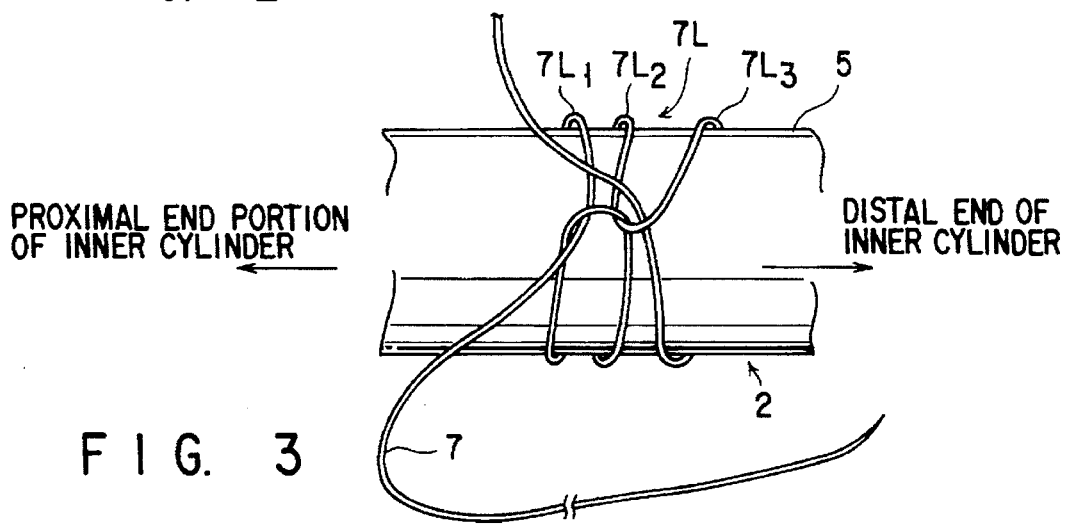
FIG. 3 is an explanatory view for explaining how to wind a suture on the inner cylinder.

An inner cylinder gripping portion 4 is provided at the distal end portion of the inner cylinder 2. The inner cylinder gripping portion 4 has a diameter substantially equal to that of the outer cylinder 3, and is thus not housed in the outer cylinder 3. A suture winding portion 5 formed with a tapered surface is provided at the rear end portion side of the inner cylinder 2. The suture winding portion 5 is inserted into the outer cylinder 3 and is housed inside a suture housing portion 9 of the outer cylinder 3 (to be described later) while maintaining the space inside the loop. A fixing portion 6 is provided between the inner cylinder gripping portion 4 and the suture winding portion 5. The fixing portion 6 is fitted in the inner wall surface of the outer cylinder 3 to fix the inner cylinder 2. A suture 7 is wound on the suture winding portion 5 of the inner cylinder 2 in a manner to be described later as shown in FIG. 3. The suture 7 forms a loop portion 7L of triple ligation for a knot. The suture 7 can be of any type as far as it is used for a surgical operation.

Figure 6A:
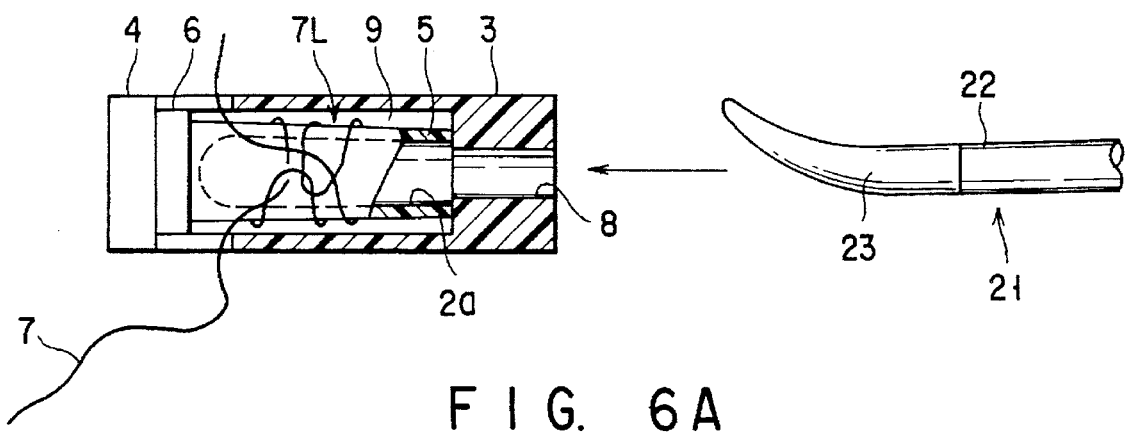
FIG. 6A is a longitudinal sectional view showing a state before the first forceps is inserted in the outer cylinder.
Figure 6B:
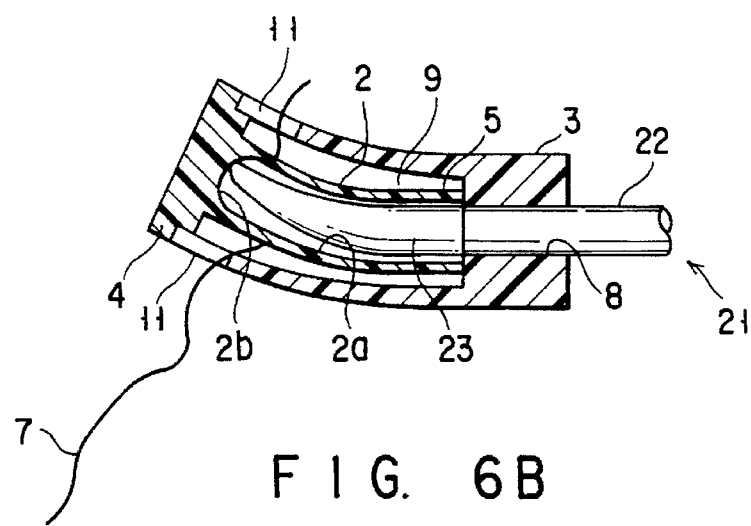
FIG. 6B is a longitudinal sectional view showing a state wherein the first forceps is inserted in the inner space of the forceps fixing portion at the rear end of the outer cylinder.

As shown in FIGS. 6A and 6B, a closed portion 2b is provided in an internal cavity 2a, on its inner cylinder gripping portion 4 side, of the inner cylinder 2. The internal cavity 2a terminates at the closed portion 2b of the inner cylinder 2 on its distal end portion side. The internal cavity 2a of the inner cylinder 2 is set such that the inner diameter of the suture winding portion 5 is larger than the diameter of a curved portion 23 formed on the distal end of an inserting portion 22 of a forceps, e.g., a Kelly clamp 21 shown in FIG. 9, which is used in combination with the suture holding member 1.

Figure 6C:
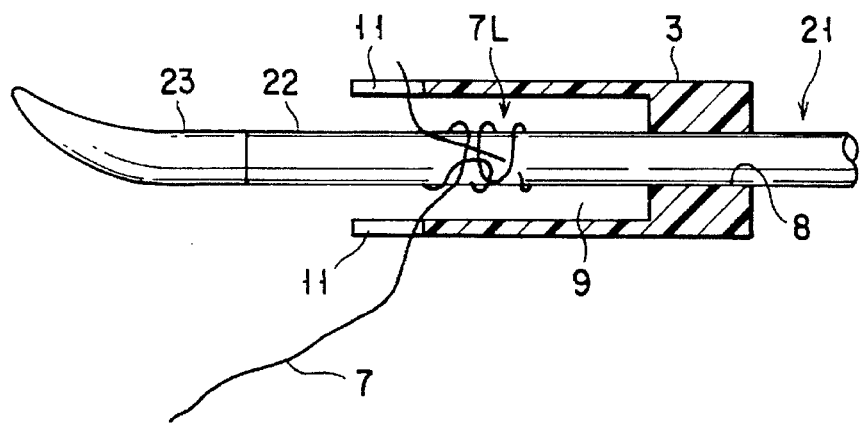
FIG. 6C is a longitudinal sectional view showing a state wherein the inner cylinder is pushed out from the outer cylinder and the suture wound on the inner cylinder is wound, as it is, on the first forceps which is inserted to replace the inner cylinder.

As shown in FIGS. 6A to 6C, a small-diameter forceps fixing portion 8 is formed in the outer cylinder 3 on its one end portion side. A suture housing portion 9 having a diameter larger than that of the forceps fixing portion 8 is formed in the outer cylinder 3 excluding the forceps fixing portion 8. The suture winding portion 5 of the inner cylinder 2, on which the loop portion 7L of the suture 7 is formed, is inserted in the suture housing portion 9. The loop portion 7L is housed between the suture winding portion 5 of the inner cylinder 2 and the suture housing portion 9 of the outer cylinder 3 while maintaining its inner space.

The length of the suture housing portion 9 is set to be almost equal to the sum of the lengths of the fixing portion 6 and the suture winding portion 5 of the inner cylinder 2. The suture housing portion 9 has an inner diameter enough to be lightly fitted in the fixing portion 6 of the inner cylinder 2.

The forceps fixing portion 8 has an inner diameter enough to be lightly close-fitted on the inserting portion 22 of, e.g., the Kelly clamp 21, which is used in combination with the suture holding member 1. Six radial incision grooves 10 are formed in the forceps fixing portion 8 to extend from its inner hole toward the outer circumference of the outer cylinder 3 at an equal angular interval in the circumferential direction of the outer cylinder 3. When a forceps is inserted, the portions among the respective incision grooves 10 are deformed comparatively easily, thereby reliably fixing the forceps.

Grooves 11 serving as suture fastening or locking means are formed by incision at two positions, opposing each other in the diametrical direction, at the distal end of the outer cylinder 3 on a side opposite to the forceps fixing portion 8. The two ends of the suture 7 wound on the suture winding portion 5 of the inner cylinder 2 are inserted in and locked by the suture locking grooves 11 of the outer cylinder 3. The outer cylinder 3 has an outer diameter enough to be inserted in an auxiliary insertion instrument, e.g., a trocar.

Figure 4A:
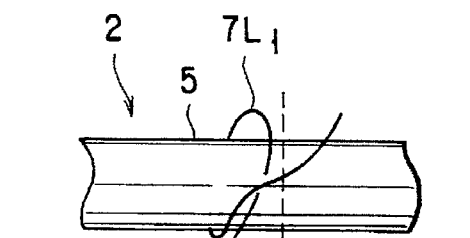
FIG. 4A is a side view showing a first loop formed by winding the suture on the inner cylinder by one turn toward the distal end of the inner cylinder.

A way of winding the suture 7 on the suture winding portion 5 of the inner cylinder 2 will be described. As shown in FIG. 4A, the suture 7 is wound on the suture winding portion 5 of the inner cylinder 2 toward its distal end by one turn to form a first loop $7L_1$ (loop 1).

Figure 4B:
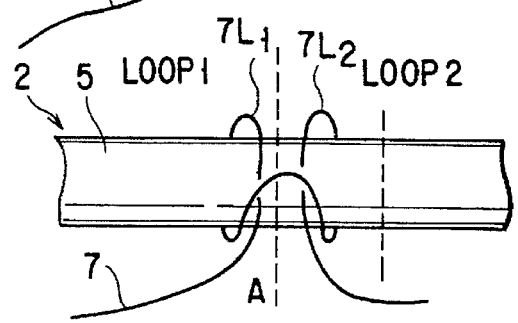
FIG. 4B is a side view showing a state wherein the suture is wound on the inner cylinder to form a second loop such that the first and second loops are symmetrical with respect to a broken line A.

Subsequently, as shown in FIG. 4B, the suture 7 is wound on the suture winding portion 5 to form a second loop $7L_2$ (loop 2) such that the loops 1 and 2 are symmetrical about a broken line A.

Figure 4C:
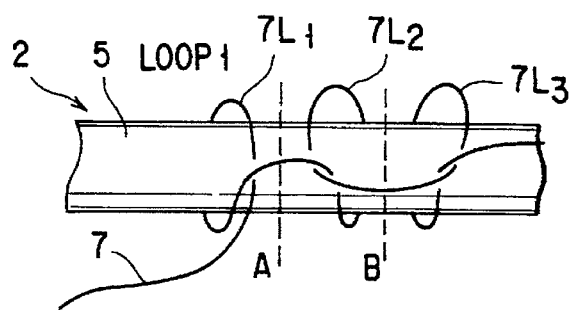
FIG. 4C is a side view showing a state wherein the suture is wound on the inner cylinder to form a third loop such that the second and third loops are symmetrical about a broken line B.

As shown in FIG. 4C, the suture 7 is wound on the suture winding portion 5 in the same manner as the loop 1 to form a third loop $7L_3$ (loop 3) such that the loops 2 and 3 are symmetrical about a broken line B.

Thus, the triple ligation loop portion 7L for the knot shown in FIG. 3 is formed. Thereafter, one end (A end) 7a of the suture 7 is passed through these three loops $7L_1$ to $7L_3$ as indicated by an arrow in FIG. 5A and fastened, so that the relationship between the suture 7 on the A end 7a side and the loops $7L_1$ to $7L_3$ of the loop portion 7L becomes identical to that of the triple ligation knot formation shown in FIG. 5B. More specifically, the loops $7L_1$, $7L_2$, and $7L_3$ correspond to a single ligation portion o, a double ligation portion p, and a triple ligation portion q, respectively, of the triple ligation formation of FIG. 5B.

Figure 2:
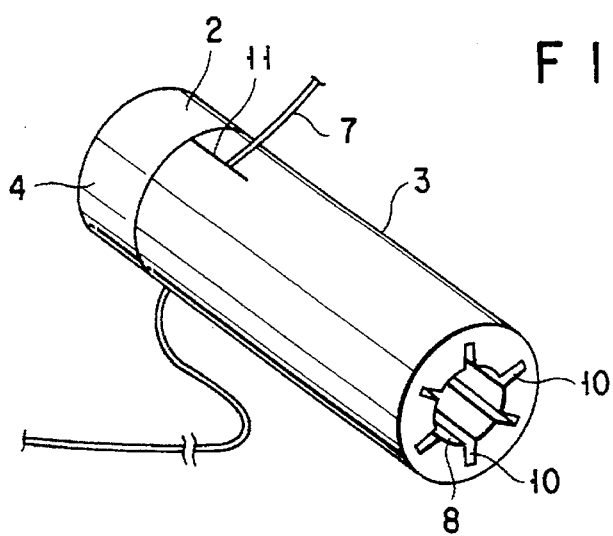
FIG. 2 is a perspective view showing a state wherein the inner cylinder of the suture holding member is fitted and fixed in the outer cylinder.

Regarding the inner cylinder 2, the outer cylinder 3, and the suture 7 of the suture holding member 1, as shown in FIG. 1, the suture 7 is wound on the suture winding portion 5 of the inner cylinder 2 to form the triple ligation loop portion 7L for the knot, and a portion of the suture winding portion 5, on which the loop portion 7L of the suture 7 is wound, is inserted in the suture housing portion 9 of the outer cylinder 3. In this state, the loop portion 7L is housed between the suture winding portion 5 of the inner cylinder 2 and the suture housing portion 9 of the outer cylinder 3 to maintain its inner space. The two ends of the suture 7 are respectively clamped and fixed by the suture locking grooves 11 of the outer cylinder 3. Finally, the fixing portion 6 of the inner cylinder 2 is fitted and fixed in the outer cylinder 3, as shown in FIG. 2.

Figure 10A:
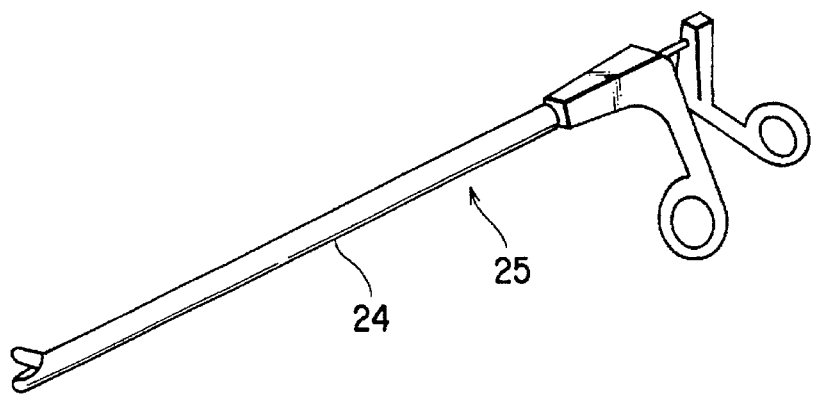
FIG. 10A is a perspective view showing a forceps having a linear inserting portion.
Figure 10B:
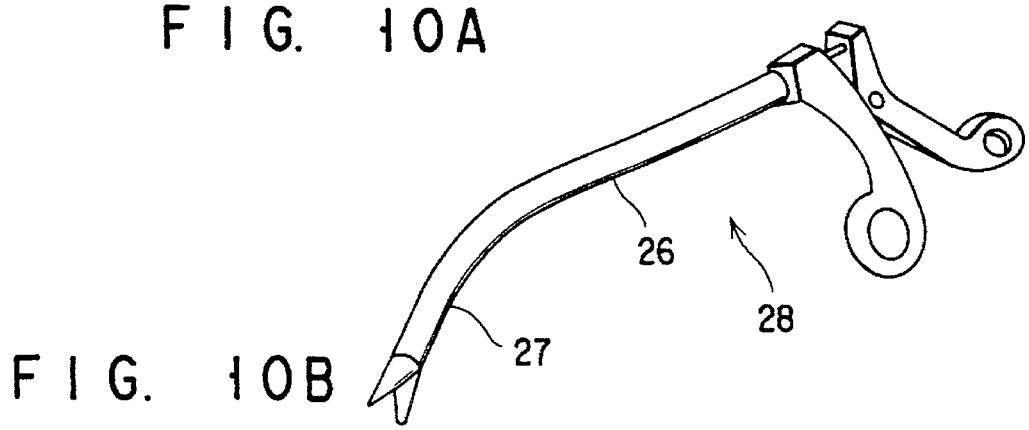
FIG. 10B is a perspective view showing a forceps having a curved portion at the distal end of its inserting portion.

The operation of the above arrangement will be described. The suture holding member 1 of this embodiment is used in combination with, e.g., the Kelly clamp 21 shown in FIG. 9, a forceps 25 having a linear inserting portion 24 as shown in FIG. 10A, or a forceps 28 having a curved portion 27 at a distal end of its inserting portion 26 as shown in FIG. 10B. A case wherein a living body tissue in the patient is to be ligated by using the Kelly clamp 21 (to be referred to as the first forceps hereinafter) shown in FIG. 9 will be described.

As shown in FIG. 6A, the inserting portion 22 of the first forceps 21 is inserted into the space in the forceps fixing portion 8 at the rear end of the outer cylinder 3 of the suture holding member 1. When the first forceps 21 is deeply inserted, the curved portion 23 at the distal end of the inserting portion 22 of the first forceps 21 is inserted into the internal cavity 2a of the suture winding portion 5 of the inner cylinder 2. A this time, since the outer and inner cylinders 3 and 2 are deformable, they are deformed in accordance with the shape of the curved portion 23 of the first forceps 21, as shown in FIG. 6B.

From this state, when the first forceps 21 is further pushed in, the distal end portion of the first forceps 21 is abutted against the closed portion 2b of the internal cavity 2a of the inner cylinder 2, and the closed portion 2b is urged by the first forceps 21 in the insertion direction of the first forceps 21, so that the inner cylinder 2 is pushed out from the outer cylinder 3. At this time, as the inner cylinder 2 is pushed out from the outer cylinder 3, the loop portion 7L of the suture 7 wound on the suture winding portion 5 of the inner cylinder 2 is disengaged with the suture winding portion 5 of the inner cylinder 2 while maintaining its original shape, and is wound on the first forceps 21 which is inserted to replace the inner cylinder 2. The inner cylinder 2 is then removed from the forceps 21.

The outer cylinder 3 is fixed on the first forceps 21 by the forceps fixing portion 8 with a light close-fit state. At this time, due to the elasticity of the material of the outer cylinder 3 and the incision grooves 10, the outer cylinder 3 can be moved on the first forceps 21 with an appropriate force in its axial direction. Thus, the outer cylinder 3 is held as it is arranged at an appropriate position on the first forceps 21, as shown in FIG. 6C.

Figure 7A:
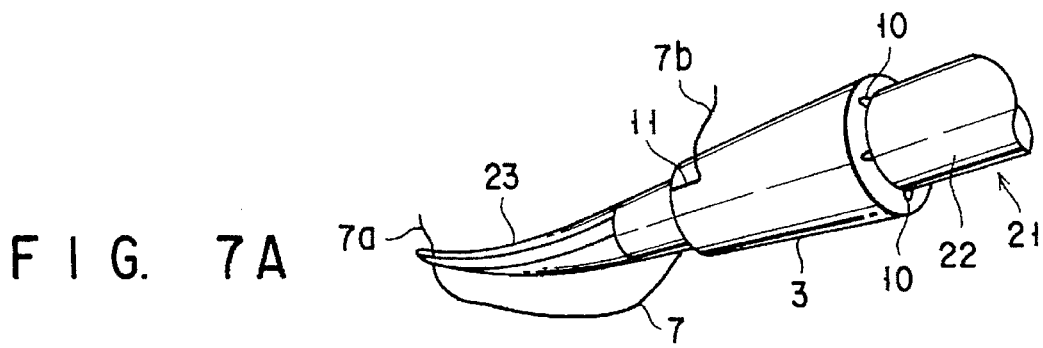
FIG. 7A is a perspective view showing a state wherein the A end of the suture is gripped by the first forceps.

When the mounting operation of the first forceps 21 and the outer cylinder 3 of the suture holding member 1 is ended in this manner, the first forceps 21, on which the outer cylinder 3 of the suture holding member 1 is mounted, is inserted into the body cavity through, e.g., a trocar, and the living body tissue is ligated. When a tubular portion, e.g., a blood vessel, is to be ligated, the A end 7a as one end of the suture 7 on its longer side is gripped with the first forceps 21, as shown in FIG. 7A.

Figure 7B:
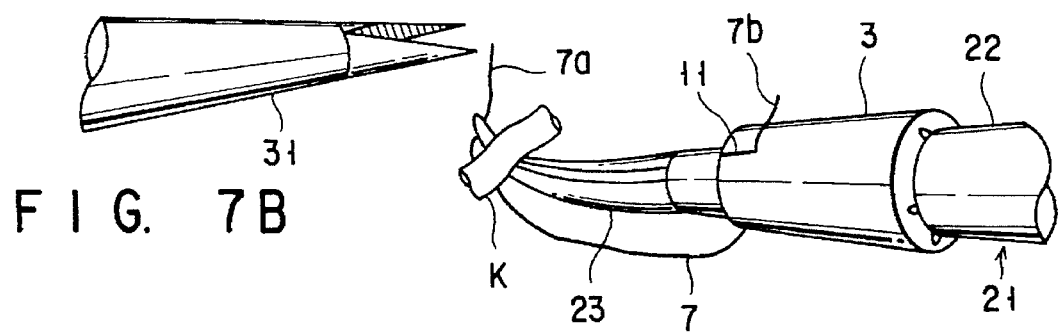
FIG. 7B is a perspective view showing a state wherein the first forceps is passed behind a ligation target tissue, e.g., a blood vessel, while holding the suture.

As shown in FIG. 7B, the distal end portion of the first forceps 21 is placed behind the portion, e.g., a blood vessel K, as the ligation target while holding the suture 7. If necessary, for example, an adhered portion behind the blood vessel K is separated with the first forceps 21 while the suture 7 is being held by the first forceps 21.

Figure 7C:
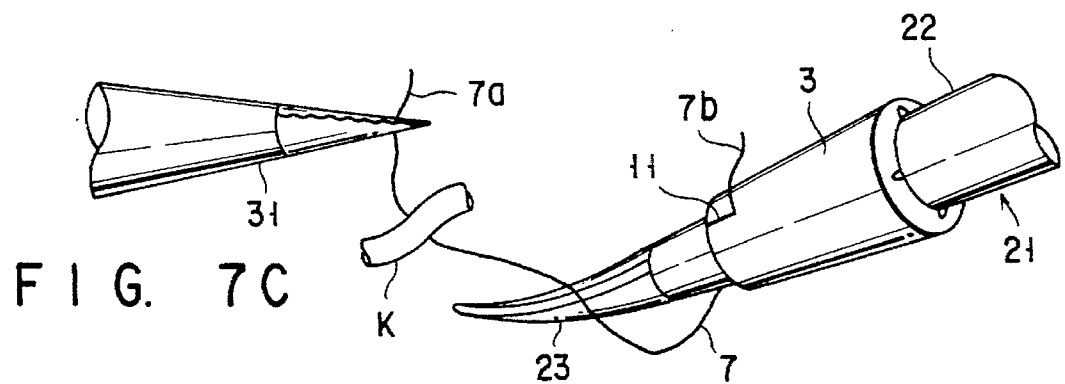
FIG. 7C is a perspective view showing a state wherein while the suture passing behind the blood vessel is held by the second forceps, the first forceps that has released the suture once is removed from the lower side of the blood vessel.
Figure 7D:
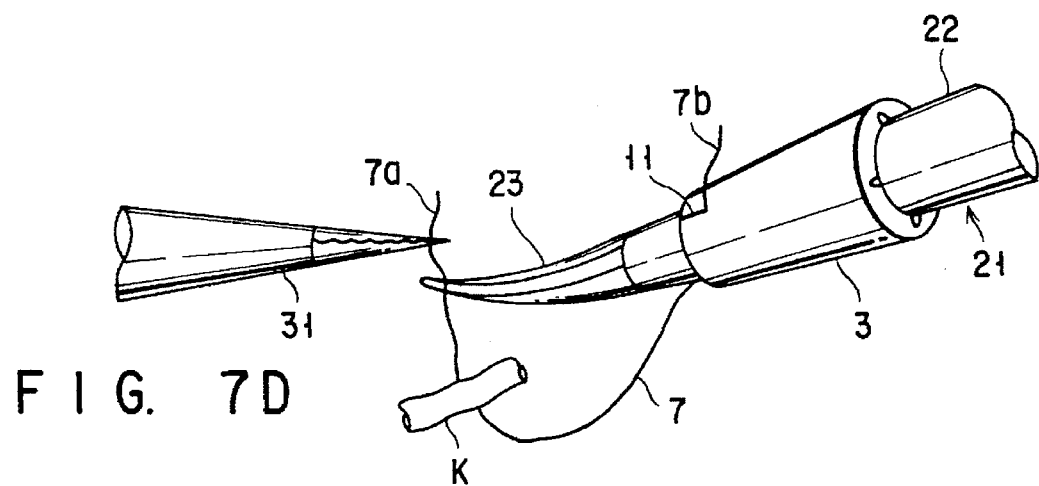
FIG. 7D is a perspective view showing a state wherein the A end of the suture held by the second forceps is seized again by the first forceps which has been removed from the lower side of the blood vessel and moved to the upper side of the blood vessel.

As shown in FIG. 7C, the A end 7a of the suture 7 which has passed behind the blood vessel K is gripped by another forceps (to be referred to as the second forceps hereinafter) 31. The first forceps 21 releases the A end 7a of the suture 7 once, is then moved from the lower side of the blood vessel K to the upper side of the blood vessel K, and seizes the A end 7a of the suture 7 held by the second forceps 31 again, as shown in FIG. 7D.

Figure 5A:
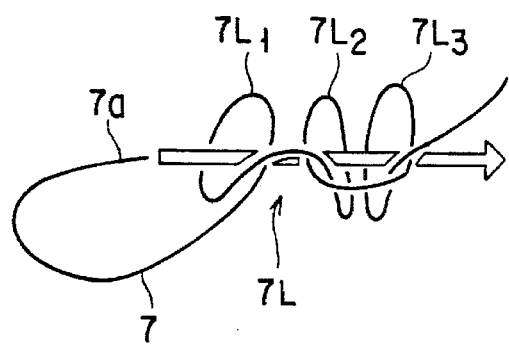
FIG. 5A is a schematic view showing a state wherein an A end of the suture is passed through the first to third loops.
Figure 5B:
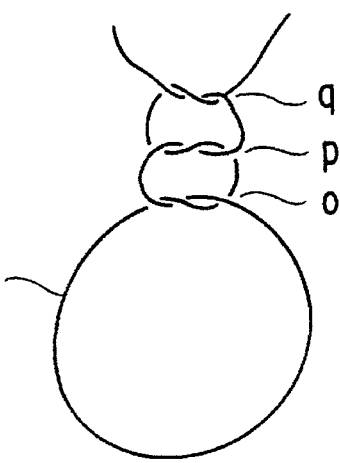
FIG. 5B is a schematic view showing a state wherein the suture forms a triple knot.
Figure 8A:
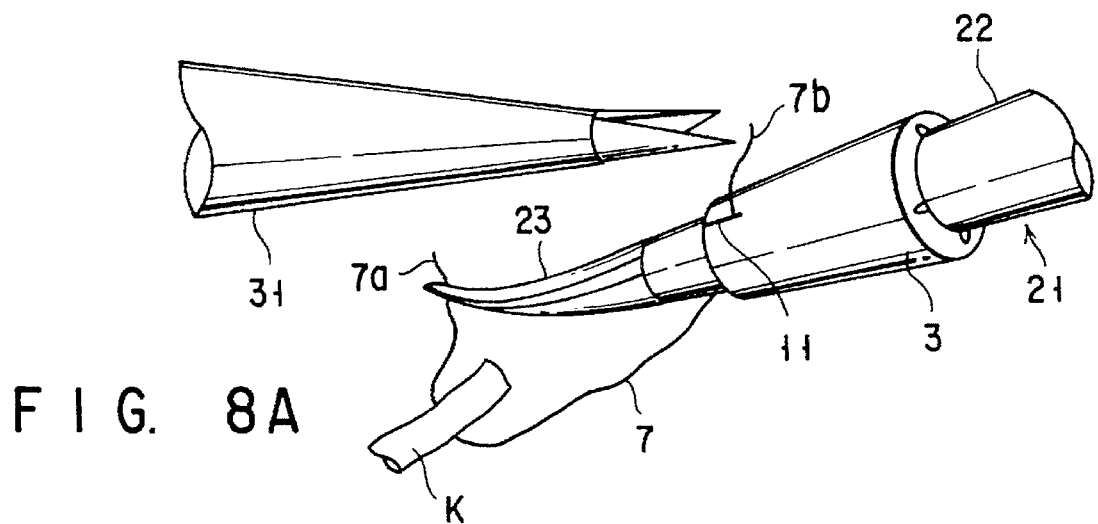
FIG. 8A is a perspective view showing a state wherein the B end of the suture fixed to the outer cylinder is seized by the second forceps that has released the A end of the suture.

As shown in FIG. 8A, the second forceps 31 releases the A end 7a of the suture 7 and seizes a B end 7b of the suture 7, on its other end side, fixed by the outer cylinder 3. In this state, the second forceps 31 is pulled toward the A end 7a of the suture 7 to pull the B end 7b, thereby extracting the B end 7b of the suture 7 from the suture locking groove 11 of the outer cylinder 3. When the second forceps 31 is further pulled, the loop portion 7L is extracted outside the outer cylinder 3. This loop portion 7L is pulled out from the distal end portion of the first forceps 21, so that the A end 7a of the suture 7 passes through the loop portion 7L, as shown in FIG. 5A.

Figure 8B:
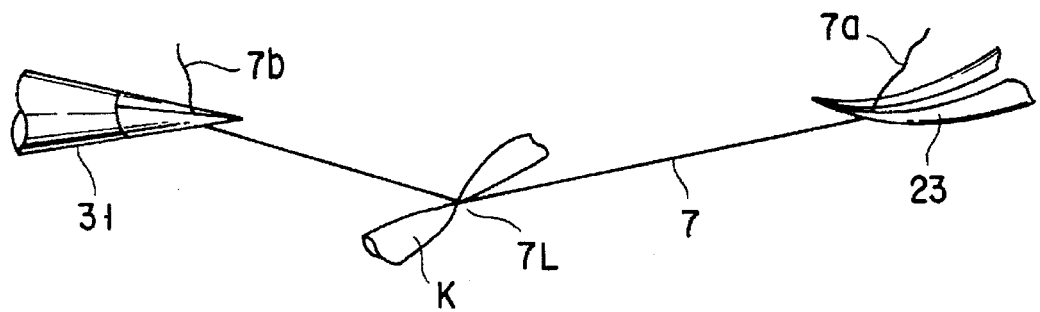
FIG. 8B is a perspective view showing a state wherein the knot of the suture is firmly fastened by the first and second forceps, thus ligating the blood vessel.
Figure 9:
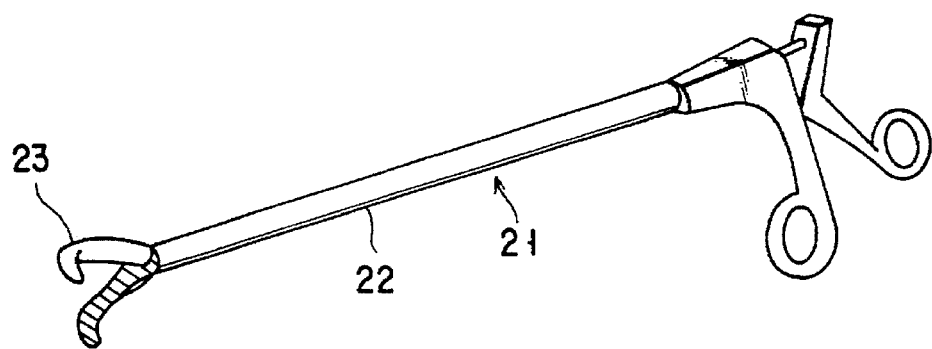
FIG. 9 is a perspective view showing a Kelly clamp.

As shown in FIG. 8B, the second forceps 31 seizing the B end 7b of the suture 7 is strongly pulled to the left in FIG. 8B, and the first forceps 21 seizing the A end 7a of the suture 7 is strongly pulled to the right in FIG. 8B, so that the knot of the loop portion 7L is strongly fastened, thereby ligating the blood vessel K.

After the blood vessel K is ligated, the extra portion of the suture 7 is cut off and recovered outside the body, thus ending the ligation operation. This applies to a case wherein the suture holding member 1 of this embodiment is used in combination with the forceps 25 and 28 shown in FIGS. 10A and 10B, and a description thereof will be omitted.

The above arrangement provides the following effect. Namely, since the inner and outer cylinders 2 and 3 of the suture holding member 1 are made of deformable elastic members, they can be used in combination with a treatment instrument having a special shape, e.g., the first forceps 21 formed with the curved portion 23 at the distal end of its inserting portion 22, the forceps 28 having the curved portion 27 at the distal end of its inserting portion 26, as shown in FIG. 10B, and the like.

After the loop portion 7L as a knot is formed in advance outside the body by the inner cylinder 2 of the suture holding member 1, the loop portion 7L can be reliably arranged in the body cavity with the first forceps 21 which is mounted in the outer cylinder 3 of the suture holding member 1 to replace the inner cylinder 2. Thus, a difficult internal ligation operation can be omitted. Therefore, the knot of the loop portion 7L is reliably and firmly fastened in the body cavity with a simple operation without particularly increasing the number of forceps required for suturing living body tissues in the body, so that tissues to be sufficiently cured can be sutured. The number of times of inserting/extracting the treatment instrument, e.g., the forceps, into/from the body cavity can also be decreased, thereby further facilitating the operation of suturing the living body tissues in the body.

When the first forceps 21 assembled with the outer cylinder 3 of the suture holding member 1 is to be inserted by, e.g., a trocar, the two ends of the suture 7 whose loop portion 7L is wound on the first forceps 21 are held as they are clamped and locked by the suture locking grooves 11 of the outer cylinder 3. Therefore, while the first forceps 21 is inserted into the trocar or the like, the suture 7 can be prevented from a shift, or the loop portion 7L can be prevented from being removed from the first forceps 21.

Since the two ends of the suture 7 are clamped and locked by the suture locking grooves 11 of the outer cylinder 3, when ligating the blood vessel K or the like, the B end 7b of the suture 7 can be easily removed by the second forceps 31 toward the distal end along the suture locking grooves 11.

Since the loop portion 7L of the suture 7 wound on the first forceps 21 is housed in the outer cylinder 3, this loop portion 7L will not move from the mounted position, be removed, or be caught by other constituent members.

Since the suture holding member 1 is provided with the inner cylinder 2 having the suture winding portion 5, when the first forceps 21 is to be mounted in the outer cylinder 3 of the suture holding member 1, the loop portion 7L can be arranged as it is on the outer surface of the first forceps 21 without changing the shape. When the suture holding member 1 of the suturing instrument is to be assembled, it suffices if the suture 7 is wound on the inner cylinder 2 and the inner cylinder 2 is inserted in the outer cylinder 3. Thus, the operation of assembling the suture holding member 1 can be facilitated.

In this embodiment, the suture holding member 1 is used in combination with a forceps, e.g., the Kelly clamp 21. However, as shown in FIG. 11, the suture holding member 1 may be used in combination with an inserting portion 33 of an endoscope (scope having a channel) 32.

Figure 11:
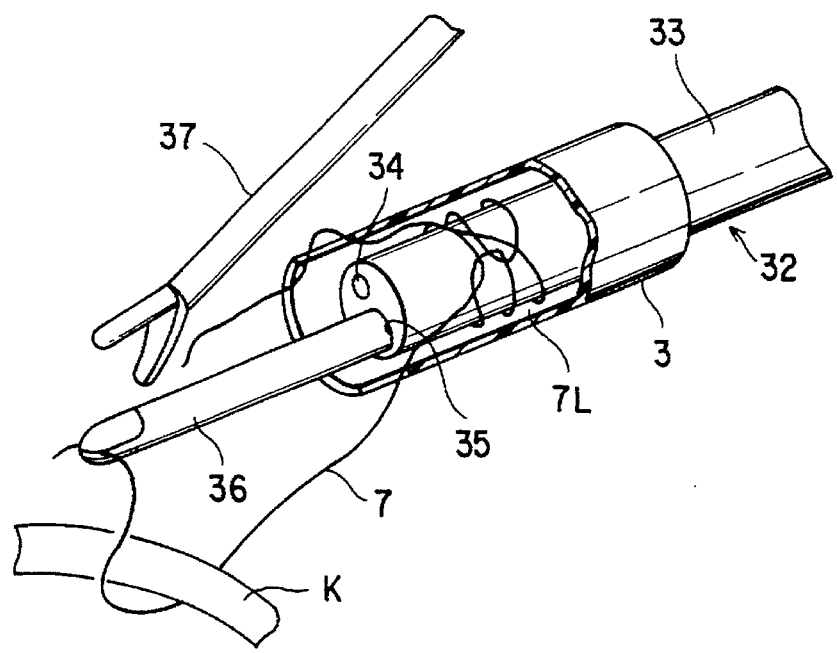
FIG. 11 is a perspective view showing a state wherein a suturing instrument is used in combination with an endoscope.

In FIG. 11, reference numeral 34 denotes an objective lens of the endoscope 32; and 35, a treatment instrument insertion channel. In this case, the inserting portion 33 of the endoscope 32 is mounted in an outer cylinder 3 of a suture holding member 1 in the same manner as the first forceps 21 of the first embodiment.

As the outer cylinder 3 of the suture holding member 1 is mounted on the inserting portion 33 of the endoscope 32, a loop portion 7L of a suture 7 wound on a suture winding portion 5 of an inner cylinder 2 is removed from the suture winding portion 5 of the inner cylinder 2 while maintaining its original shape, and is wound on the inserting portion 33 of the endoscope 32 which is inserted to replace the inner cylinder 2.

After the inserting portion 33 of the endoscope 32, on which the outer cylinder 3 of the suture holding member 1 is mounted, is inserted into the body cavity, a first forceps 36, which is inserted into the body cavity through the treatment instrument insertion channel 35 of the endoscope 32, and a second forceps 37, which is inserted into the body cavity independently of the endoscope 32, are operated to pass the suture 7 through the body tissue as the ligation target, e.g., a blood vessel K, under observation with the endoscope 32, thereby performing suture.

In this manner, when the suture holding member 1 is used in combination with the inserting portion 33 of the endoscope 32, the first forceps 36 as one forceps can be inserted into the body cavity through the treatment instrument insertion channel 35 of the endoscope 32. Therefore, the number of insertion holes for the treatment instruments to be formed in the patient's body wall can be decreased by one, thereby decreasing load to the patient.

A suture attached with a needle, obtained by coupling the needle to the distal end of a suture 7, may be used in combination with the suture holding member 1 of the first embodiment. When this suture attached with the needle is used, a needle retainer may be preferably used as a forceps to be inserted into the suture holding member 1.

After the suture holding member 1 is mounted on the needle retainer in the same manner as in the first embodiment, the suture holding member 1 is inserted into the body cavity. While the needle is supported by the needle retainer, the suture 7 is passed through the body tissues as the suturing target, and the suture 7 is ligated, thereby performing suture. When the suture attached with the needle is used in this manner, a wounded portion can be sutured together.

Figure 12:
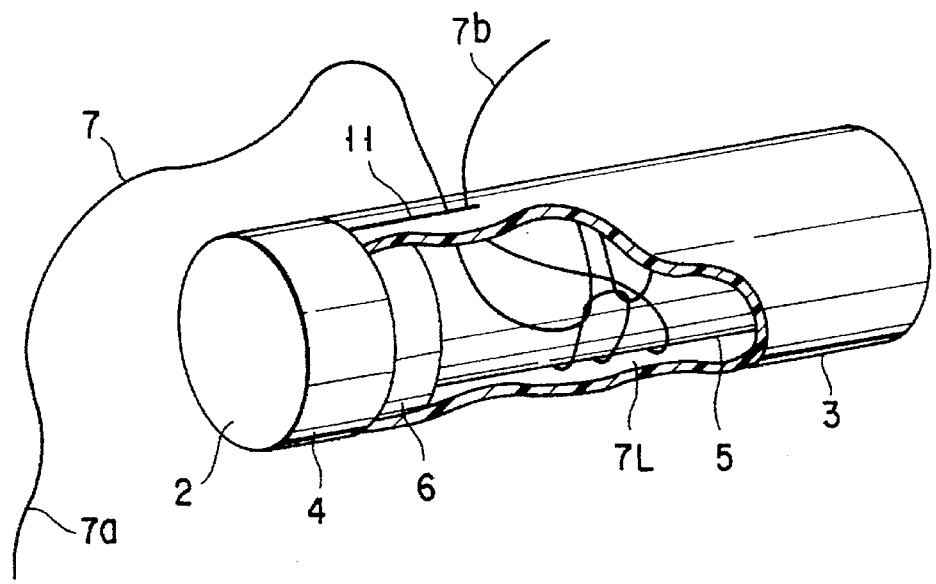
FIG. 12 is a partially cutaway perspective view showing a suture holding member according to the first modification of the first embodiment.

FIG. 12 shows the first modification of the suture holding member 1 according to the first embodiment. In this suture holding member 1, the outer cylinder 3 has one suture locking groove 11, and the two ends of the suture 7 to form the loop portion 7L are inserted in and gripped by one suture locking groove 11. In this case, one end of the suture 7, i.e., the B end 7b on its shorter in this case, is inserted in the suture locking groove 11 first, and then the other end of the suture 7, i.e., the A end 7a on its longer side is inserted in this suture locking groove 11.

The suture holding member 1 according to this modification is used in the same manner as in the first embodiment. Therefore, in this case, when the B end 7b of the suture 7 is pulled to remove the suture 7 from the suture locking groove 11, the A end 7a is also removed from the suture locking groove 11 as it is pushed by the B end 7b of the suture 7, so that the two ends of the suture 7 can be easily removed from the outer cylinder 3.

Figure 13:
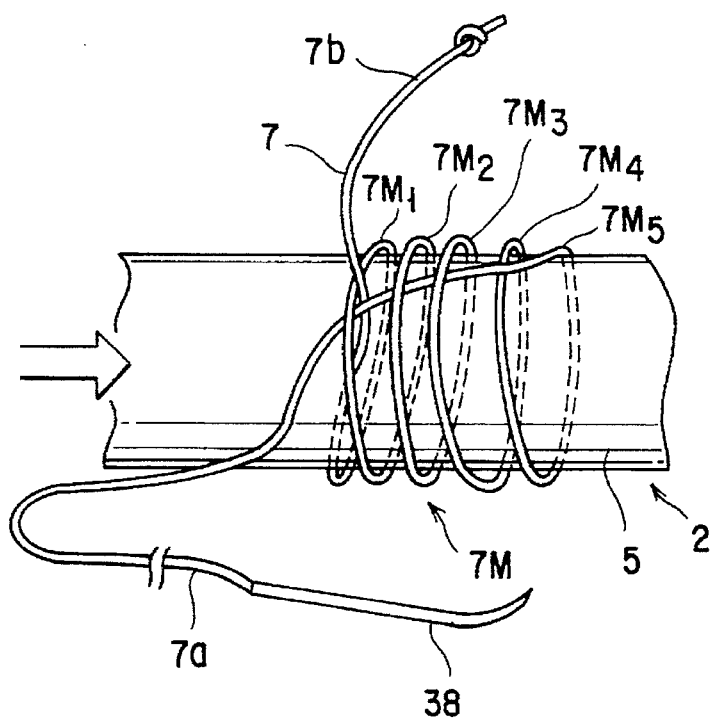
FIG. 13 is a perspective view showing a wound state of the suture according to the second modification of the first embodiment.

FIG. 13 shows the second modification of the first embodiment. In this modification, a loop portion 7M is formed by altering the manner to wind the suture 7. More specifically, the A end 7a of the suture 7 is wound on the suture winding portion 5 of an inner cylinder 2 a plurality of number of times, e.g., five times, from the left as indicated by an arrow in FIG. 13, to form five loops $7M_1$ to $7M_5$. The A end 7a is passed through the loops $7M_3$, $7M_2$, and $7M_1$ from the right in FIG. 13, and the B end 7b of the suture 7 is passed under the loop $7M_1$ and fastened, thereby forming a knot which is a so-called loader knot. A needle 38 is coupled to the A end 7a of the suture 7.

Figure 14A:
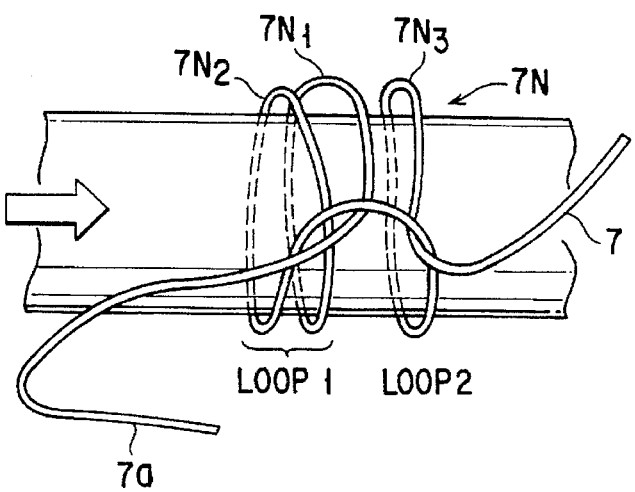

FIG. 14A shows the third modification of the first embodiment. In this modification, a loop portion 7N is formed by further altering the manner to wind the suture 7. More specifically, the suture 7 is wound on the suture winding portion 5 of the inner cylinder 2 by two turns from the right in FIG. 14A to form the loop 1 consisting of two loops $7N_1$ and $7N_2$. The terminal end portion of the left loop $7N_2$ is set to intersect the starting end portion of the right loop $7N_1$ and bent back in the opposite direction, and the suture 7 is wound on the suture winding portion 5 by one turn, thereby forming a loop $7N_3$ (loop 2).

Figure 14B:

When an A end 7a of this suture 7 is passed through the loops 1 and 2 from the left as indicated by an arrow in FIG. 14A and fastened, the suture 7 on the A end 7a side and the suture 7 on the loop portion 7N side provide a positional relationship identical to that of a so-called surgeon knot, as shown in FIG. 14B.

Figure 15:
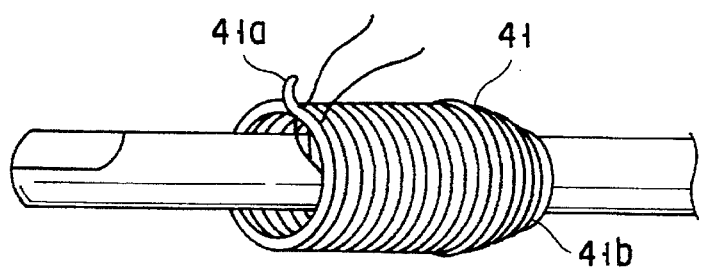
FIG. 15 is a perspective view of an outer cylinder according to the fourth modification of the first embodiment.

FIG. 15 shows the fourth modification of the first embodiment. In this modification, a member corresponding to the outer cylinder 3 of the first embodiment is formed by a coil spring 41.

As the material of the coil spring 41, a metal material, e.g., stainless steel, or a synthetic resin material is preferable. A distal end 41a of the wire of the coil spring 41 is slightly bent so that the coil spring 41 can easily hold the suture 7. The two end portions of the suture 7 are clamped in a gap of the coil spring 41 on the distal end 41a side, thereby locking the suture 7.

A forceps fixing portion 41b having an inner coil diameter smaller than the outer diameter of the forceps to be used is formed at the rear end portion of the coil spring 41 that forms the outer cylinder 3. At the forceps fixing portion 41b, the inner diameter of the coil spring 41 is smaller than the outer diameter of the forceps to be used. Excluding this, the arrangement of this modification is the same as that of the first embodiment. In this case, since the coil spring 41 is deformable, it can be applied to a curved forceps as in the first embodiment.

Figure 16:
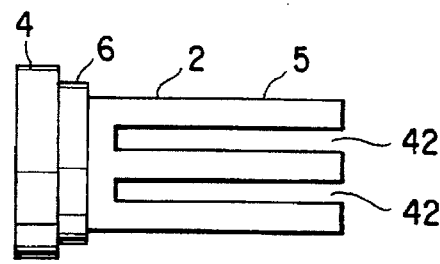
FIG. 16 is a side view of an inner cylinder according to the fifth modification of the first embodiment.

FIG. 16 shows the fifth modification of the first embodiment. In this modification, a plurality of slits 42 are circumferentially formed in the suture winding portion 5 of the inner cylinder 2 identical to that of the first embodiment, to extend along the axial direction of the inner cylinder 2.

Therefore, in this case, the suture winding portion 5 of the inner cylinder 2 can be deformed in a direction perpendicular to the axial direction of the suture winding portion 5 more easily than in the first embodiment. As the material of the inner cylinder 2, in addition to those used in the first embodiment, a metal material, e.g., stainless steel or aluminum, can be used.

Figure 17:
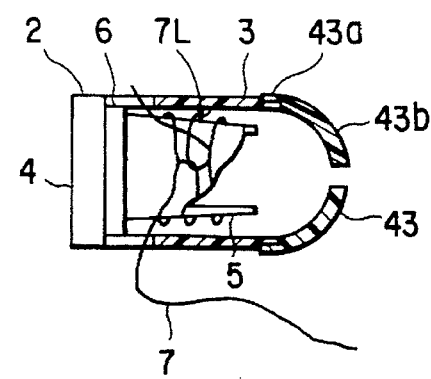
FIG. 17 is a side view of a suture holding member according to the sixth modification of the first embodiment.

FIG. 17 shows the sixth modification of the first embodiment. In this modification, the lengths of the inner and outer cylinders 2 and 3 corresponding to those of the first embodiment are decreased, and the forceps fixing portion 8 of the outer cylinder 3 is formed of a rubber cap 43. A fitting portion 43a is formed on one end portion of the rubber cap 43 to be fitted and fixed on the end portion of the outer cylinder 3, and a small-diameter portion 43b is formed on the other end portion of the rubber cap 43 to have such a size that it is lightly close-fitted with the which is used in combination with this forceps.

Also in this case, the suture holding member can be used in the same manner as that of the first embodiment. In this modification, since the lengths of the inner and outer cylinders 2 and 3 in the axial direction are small and the rubber cap 43 is used as the forceps fixing portion 8 of the outer cylinder 3, even a curved forceps can be used easily. For this reason, the inner and outer cylinders 2 and 3 can be made of made of non-deformable hard members.

Figure 18A:
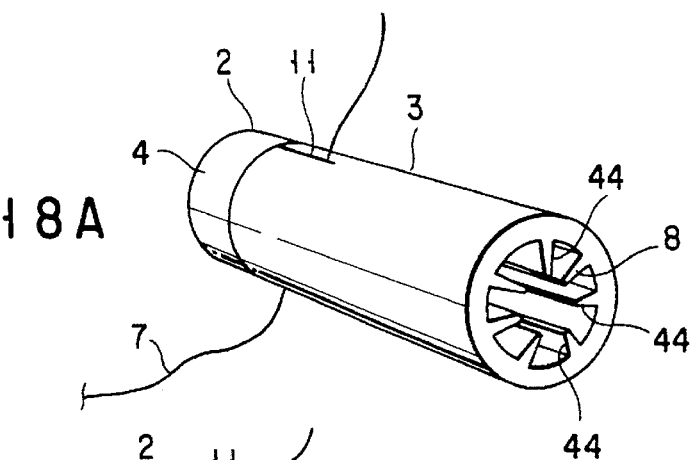
Figure 18B:
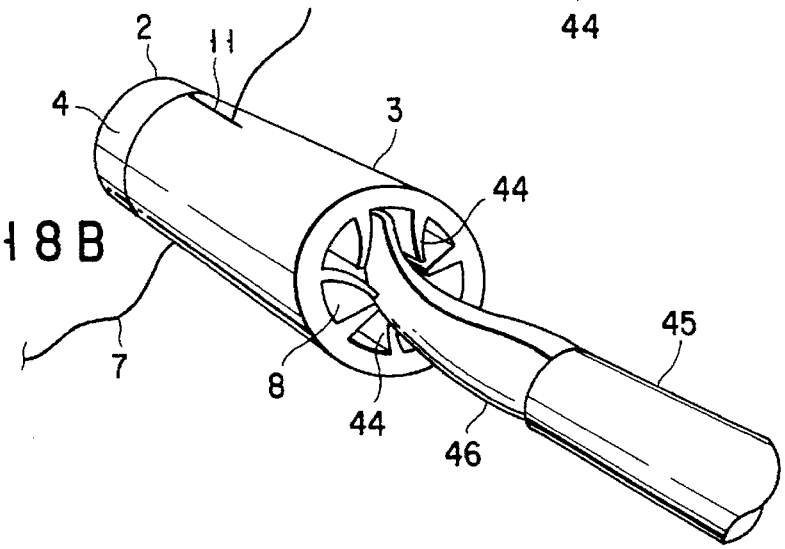

FIGS. 18A and 18B show the seventh modification of the first embodiment. In this modification, a plurality of projections 44 having tapered distal ends are formed in the forceps fixing portion 8 of the outer cylinder 3 corresponding to that of the first embodiment. In this case, as shown in FIG. 18B, when a curved portion 46 at the distal end of a forceps 45 is inserted into the forceps fixing portion 8 of the outer cylinder 3, the forceps 45 can pass through the forceps fixing portion 8 while elastically deforming the tapered projections 44 by urging them with the curved portion 46 at its distal end. Thus, even the curved forceps 45 can be used in the same manner as in the first embodiment.

Figure 19:
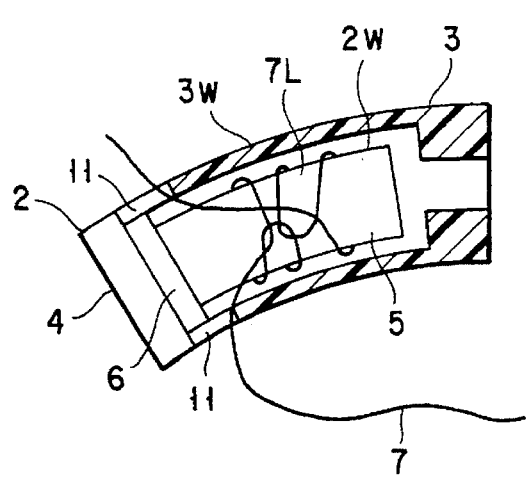
FIG. 19 is a longitudinal sectional view of a suture holding member according to the eighth modification of the first embodiment.

FIG. 19 shows the eighth modification of the first embodiment. In this modification, curved portions 2w and 3w are respectively formed on the suture winding portion 5 of the inner cylinder 2, and the outer cylinder 3, of the suture holding member 1 corresponding to that of the first embodiment. The curved portions 2w and 3w are curved in accordance with the curved state of the curved portion 27 of the forceps 28, as shown in FIG. 10B, which is used in combination with this suture holding member 1. Therefore, also in this case, the curved forceps 28 can be easily used in the same manner as in the first embodiment.

Figure 20:
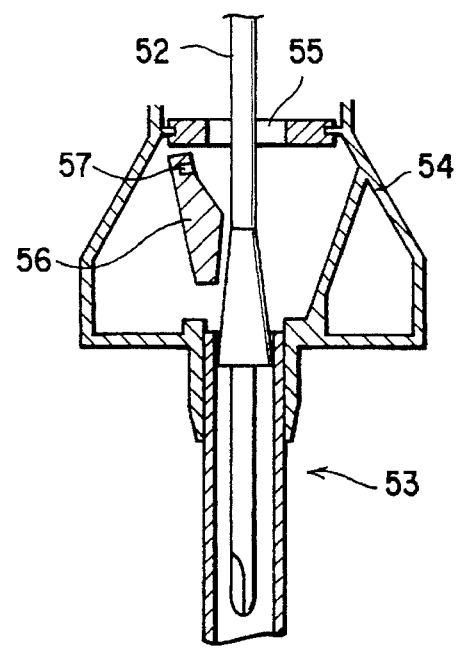
FIG. 20 is a longitudinal sectional view showing the state of use of a suture holding member according to the ninth modification of the first embodiment.

FIGS. 20 and 21 show the ninth modification of the first embodiment. In this modification, as shown in FIG. 21, a large tapered chamfered portion 51 is formed on the rear portion of a main body 3B of the outer cylinder 3 of the suture holding member 1.

FIG. 20 shows a state wherein a forceps 52 mounted in the outer cylinder 3 of the suture holding member 1 is inserted into a trocar 53. A movable valve 56 for keeping air-tightness of a forceps insertion port 55 is provided at a forceps insertion port body 54 of the trocar 53.

The movable valve 56 is axially supported to be pivotal about a pivot shaft 57. The movable valve 56 is normally biased by a biasing means, e.g., a spring (not shown), in a direction to close the forceps insertion port 55. When the forceps 52 is not inserted into the trocar 53, the forceps insertion port 55 is closed by the movable valve 56, thereby keeping air-tightness of the forceps insertion port 55.

When the forceps 52 is to be inserted into the trocar 53, the movable valve 56 is pushed downward by the distal end portion of the inserting portion of the forceps 52 against the biasing force, so that the movable valve 56 is opened.

Therefore, in the above arrangement, when the forceps 52 inserted into the body through the trocar 53 is to be extracted outside the trocar 53, the chamfered portion 51 at the rear portion of the main body 3B of the suture holding member 1 prevents the main body 3B of the outer cylinder 3 of the suture holding member 1 from being caught by the movable valve 56 of the trocar 53.

FIG. 22 shows the tenth modification of the first embodiment. In this modification, the entire portion of a main body 3B' of the outer cylinder 3 of the suture holding member 1 is made substantially conical. Also in this case, the same effect as that of the ninth modification can be obtained.

FIG. 23 shows the eleventh modification of the first embodiment. In this modification, a hook portion 59 for hooking, e.g., a recovering cord 58, is provided to the outer cylinder 3 of the suture holding member 1.

In this case, when the forceps 52 inserted into the body through the trocar 53 shown in FIG. 20 is to be extracted outside the trocar 53, even if the outer cylinder 3 of the suture holding member 1 is caught by the movable valve 56 of the trocar 53 and thus removed from the forceps 52, the outer cylinder 3 can be easily recovered by pulling the recovering cord 58.

Figure 24A:
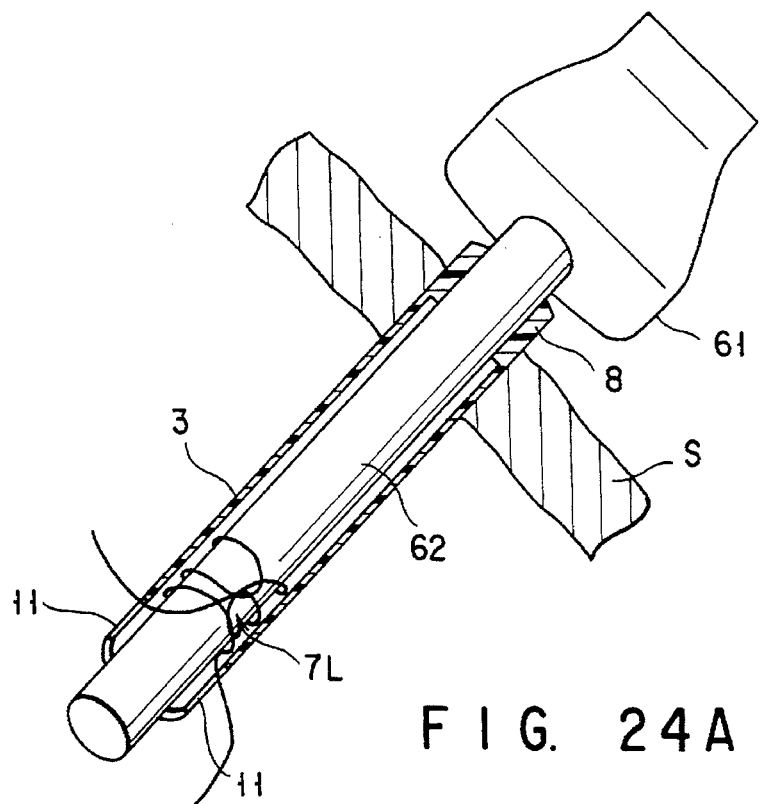

FIG. 24A shows the twelfth modification of the first embodiment. In this modification, the suture holding member 1 is used in combination with a trocar 61 which is an instrument for an endoscopic operation.

The length of the outer cylinder 3 of the suture holding member 1 in the axial direction is set to be slightly smaller than that of a cannula 62 of the inserting portion of the trocar 61. The forceps fixing portion 8 of the outer cylinder 3 does not have the radial incision grooves 10 unlike in the first embodiment. The inner diameter of the forceps fixing portion 8 of the outer cylinder 3 is set to be slightly smaller than that of the inserting portion of the surgical instrument inserted into the cavity of the forceps fixing portion 8, e.g., the cannula 62 of the trocar 61 in this modification.

Therefore, when the cannula 62 of the trocar 61 is inserted into the cavity in the forceps fixing portion 8 of the outer cylinder 3 until its base, the inner circumferential surface of the forceps fixing portion 8 of the outer cylinder 3 is deformed in accordance with the shape of the cannula 62 of the trocar 61 which is being inserted, so that the outer cylinder 3 is fitted on the trocar 61 in a close-fit state and brought into tight contact, thereby keeping air-tightness.

When the suture holding member 1 having the above arrangement is used, the outer cylinder 3 of the suture holding member 1 is mounted on the cannula 62 of the trocar 61 in accordance with the same procedure as in the first embodiment. As the outer cylinder 3 of the suture holding member 1 is mounted on the cannula 62 of the trocar 61, the loop portion 7L of the suture 7 wound on the suture winding portion 5 of an inner cylinder 2 is removed from the suture winding portion 5 of the inner cylinder 2 while maintaining its original shape, and is then wound on the cannula 62 of the trocar 61 which is inserted to replace the inner cylinder 2.

An inner needle (not shown) of the trocar 61 is inserted and mounted in the cannula 62 of the trocar 61 on which the outer cylinder 3 of the suture holding member 1 is mounted. While the inner needle is inserted in the cannula 62 of the trocar 61, the trocar 61 is pierced into a patient's body wall S and passes through it into the body cavity.

After the trocar 61 is inserted into the body cavity, the inner needle is extracted from the cannula 62, and the first forceps 21 is inserted into the cannula 62 instead. After this, the suture 7 is ligated by operating the first forceps 21 and the second forceps 31, which is inserted into the body cavity separately of the first forceps 21, in the same manner as in the first embodiment.

When the suture holding member 1 is used in this manner, since the outer cylinder 3 of the suture holding member 1 is mounted on the trocar 61, the first forceps 21 can be singly inserted into the trocar 61. Thus, the operating force of the first forceps 21 can be small. Since the trocar 61 and the outer cylinder 3 of the suture holding member 1 are brought into tight contact with each other, air-tightness can be maintained when, e.g., pneumoperitoneum is needed.

Figure 24B:
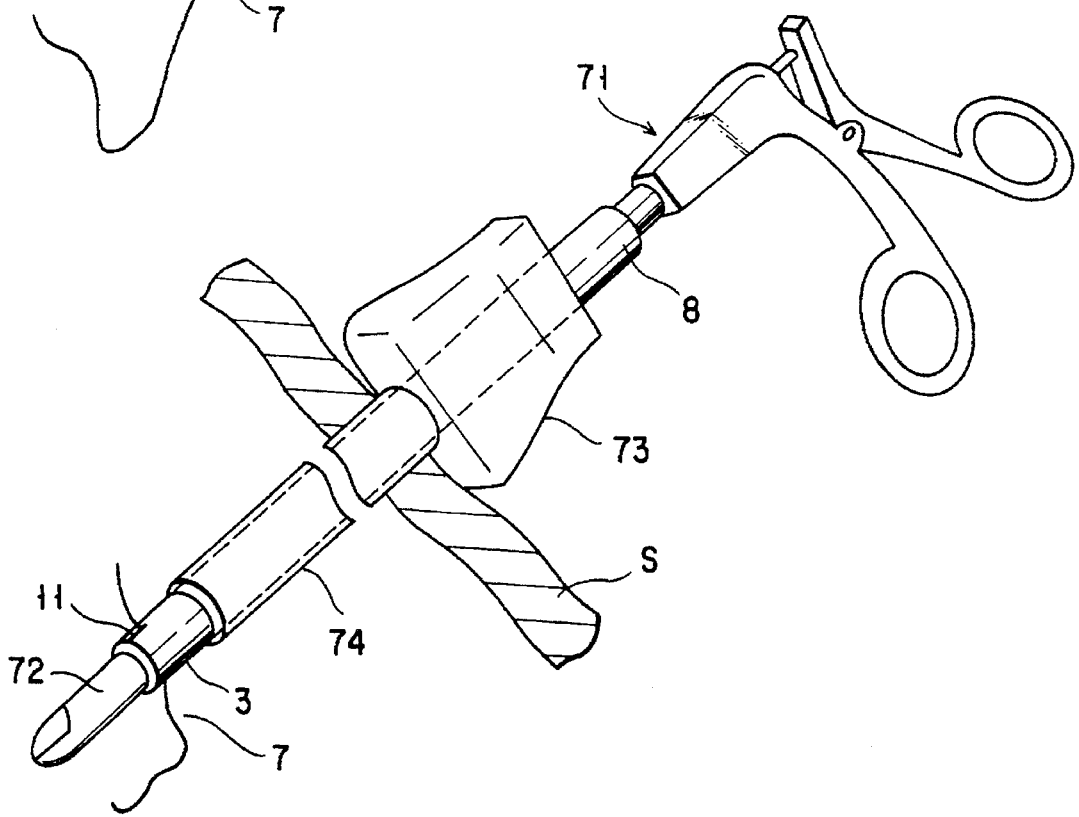

In FIG. 24B, the outer cylinder 3 of the suture holding member 1 according to the twelfth modification shown in FIG. 24A is used in combination with a forceps 71. Also in this case, the outer cylinder 3 of the suture holding member 1 is mounted on an inserting portion 72 of the forceps 71 up to the base of the inserting portion 72, in the same manner as the cannula 62 of the trocar 61 shown in FIG. 24A. At this time, the inserting portion 72 of the forceps 71 and the forceps fixing portion 8 of the outer cylinder 3 of the suture holding member 1 are brought into tight contact with each other, thereby maintaining air-tightness.

The inserting portion 72 of the forceps 71, on which the outer cylinder 3 of the suture holding member 1 is mounted, is inserted into the body cavity through a cannula 74 of a trocar 73. At this time, the seal member (not shown) of the trocar 73 and the outer circumferential surface of the outer cylinder 3 of the suture holding member 1 are brought into tight contact with each other, thereby maintaining air-tightness. After this, a suture 7 is ligated by operating the forceps 71 (A forceps) and the B forceps 31, which is inserted into the body cavity separately of the A forceps 71, in the same manner as in the first embodiment.

Therefore, in this case, since the outer cylinder 3 of the suture holding member 1 is in tight contact with the outer circumferential surface of the inserting portion 72 of the forceps 71 to maintain air-tightness, and since the trocar 73 and the outer cylinder 3 of the suture holding member 1 are also in tight contact with each other to maintain air-tightness, the air-tightness in the patient's body cavity can be maintained when, e.g., pneumoperitoneum is needed.

Figure 25:
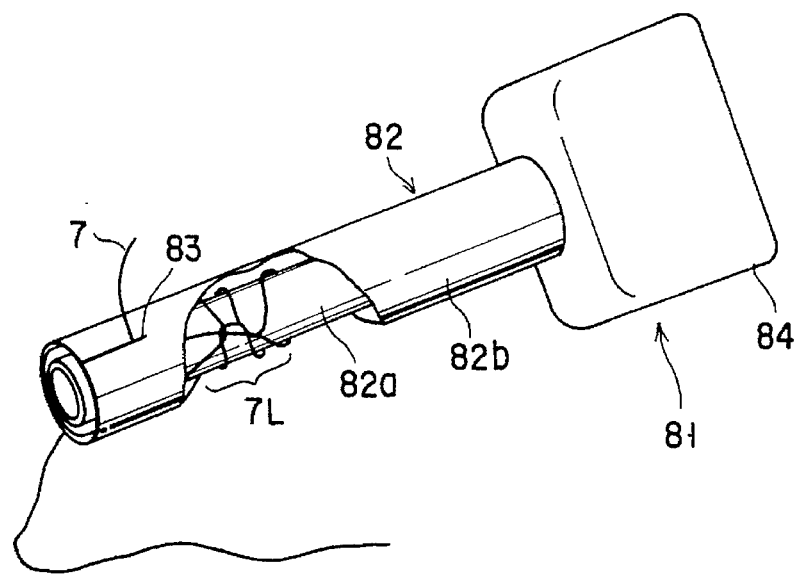
FIG. 25 is a perspective view showing a modification of the trocar.

In FIG. 25, a cannula portion 82 of a trocar 81 is made by two pipes (an inner cylinder 82a and an outer cylinder 82b), and the inner and outer cylinders 82a and 82b of the trocar 81 are utilized as the inner and outer cylinders 2 and 3, respectively, of the suture holding member 1 of the first embodiment.

In this case, the loop portion 7L of the suture 7 is wound on the outer circumferential surface of the outer cylinder 82b, and the extending portion of the suture 7, extending from the loop portion 7L, is fixed in an incision-like suture locking groove 83 formed in the outer cylinder 82b. A movable valve 56 (see FIG. 20) for maintaining air-tightness is provided at a forceps insertion port body 84 of the trocar 81.

When the trocar 81 having the above arrangement is used, it is used in combination with an inner needle (not shown), and is pierced into the patient's body wall S. After the trocar 81 extends through the patient's body wall S and the distal end portion of the trocar 81 is inserted into the body cavity, the inner needle is extracted. Subsequently, the A forceps 21 is inserted into the cavity in the inner cylinder 82a of the trocar 81. After this, the suture 7 is passed through a body tissue by operating the A forceps 21 and the B forceps 31, which is inserted into the body cavity independently of the A forceps 21, in the same manner as in the first embodiment, and is ligated.

Figure 26:
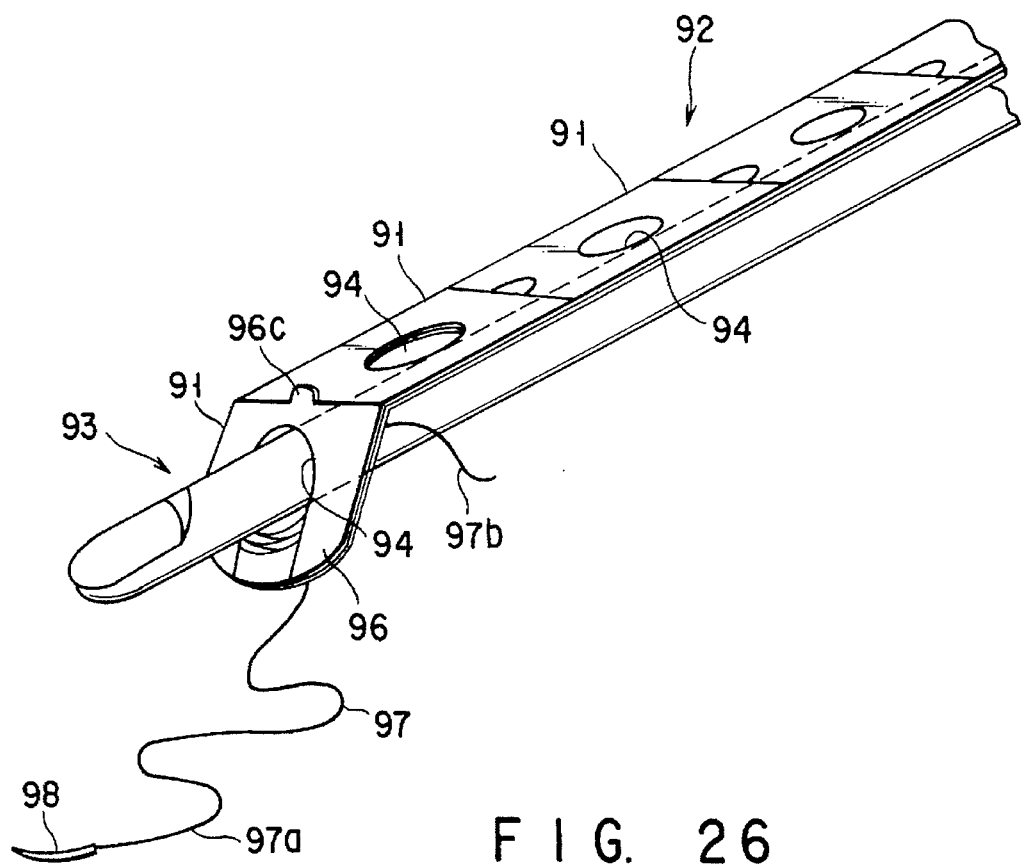
FIG. 26 is a perspective view showing a film unit coupling body of a suturing instrument according to the second embodiment of the present invention.

FIGS. 26 to 30 show the second embodiment of the present invention. FIG. 26 shows a substantially tape-like film unit coupling body 92 obtained by continuously coupling a large number of film units 91, which are the suture holding members of a suturing instrument, in a row. A forceps insertion port 94 for allowing insertion of a forceps 93 therethrough is formed at the central portion of each film unit 91.

Figure 27:
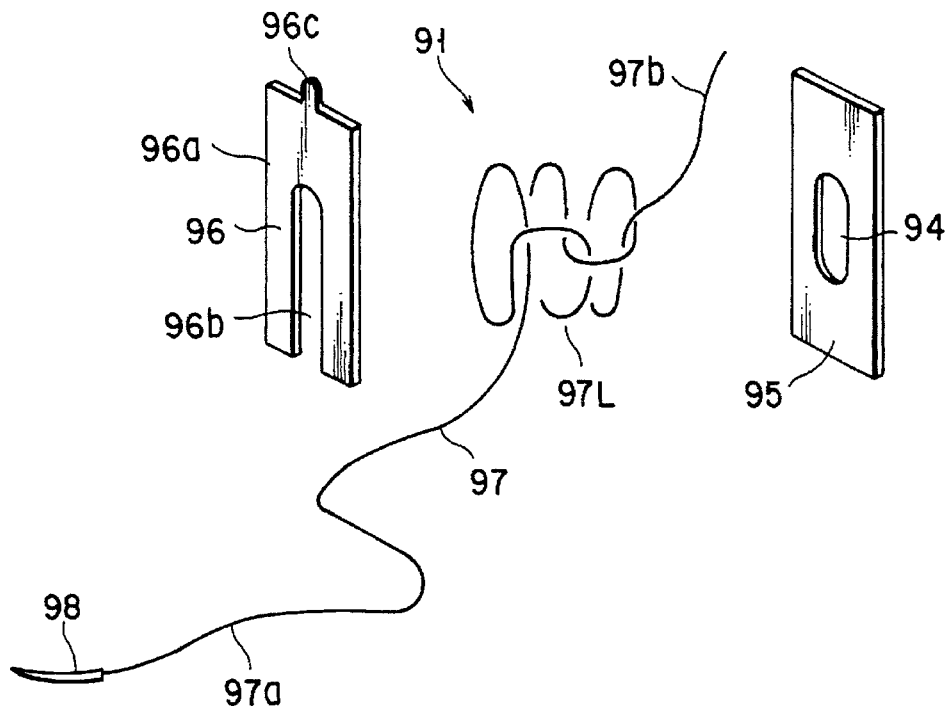
FIG. 27 is an exploded perspective view of a film unit.

As shown in FIG. 27, each film unit 91 is constituted by a base film 95, a retaining film 96 detachably bonded to the base film 95, and a suture 97. The base film 95 and the retaining film 96 are sufficiently thin, flexible, and deformable. Various types of synthetic resin materials and paper can be used as the material of the base film 95 and the retaining film 96. Each film unit 91 is connected to an adjacent film unit 91 through the flexible base film 95.

A slot 96b is formed in the retaining film 96 to extend from one end portion of a film body 96a, i.e., the lower end portion in FIG. 27, to a position corresponding to the forceps insertion port 94 at the central portion of the retaining film 96. The entire portion of the retaining film 96 has a substantially inverted U shape. A tag 96c is provided to project from at the upper end portion of the film body 96a of the retaining film 96. The tag 96c is separate from the base film 95.

A loop portion 97L similar to the loop portion 7L shown in FIG. 3 is formed on the suture 97. A needle 98 is coupled to the distal end of the extending portion of the loop portion 97L on a side of an A end portion 97a as one end portion. The loop portion 97L of the suture 97 is sandwiched and accommodated between the base film 95 and the retaining film 96 such that the center of the loop portion 97L and the forceps insertion port 94 coincide. Thus, the loop portion 97L maintains its inner space and is accommodated in the film unit 91, and simultaneously the suture 97 is locked by the film unit 91 serving as the suture holding member.

The operation of the above arrangement will be described. First, when a film unit 91 is to be used, the film unit coupling body 92 of the film units 91 is inserted into the body cavity through, e.g., a trocar.

Subsequently, a first forceps (to be referred to as an A forceps hereinafter) 93 that mainly operates the needle 98 is inserted into the body cavity through the same hole in the patient's body wall and from the same trocar as those used for inserting the film unit coupling body 92. The A forceps 93 may be inserted through another hole in the patient's body wall.

Figure 28:
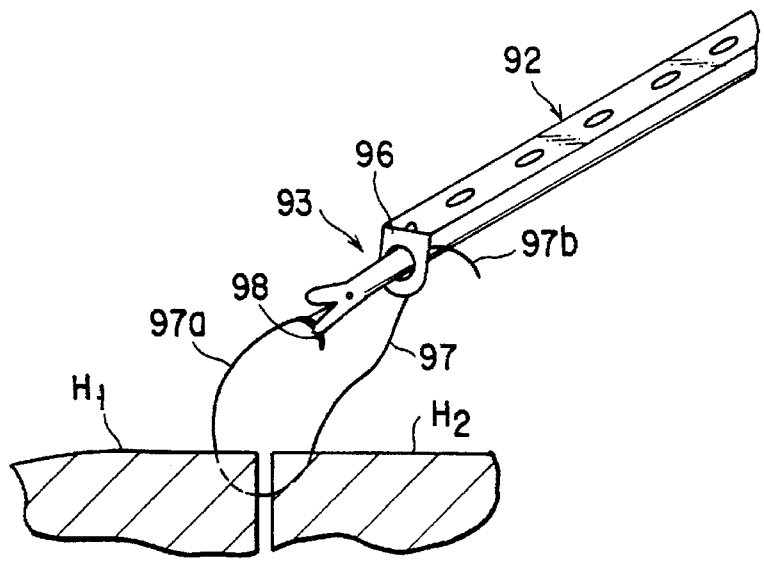
FIG. 28 is a perspective view showing a state wherein a needle is passed through a portion to be sutured in order to pass a suture through the tissues.

As shown in FIG. 28, the A forceps 93 is inserted in the forceps insertion port 94 of the film unit 91 at the frontmost end of the film unit coupling body 92, and the needle 98 is picked up with the A forceps 93. The needle 98 is passed through a portion to be sutured, and the suture 97 is passed between living body tissues $H_1$ and $H_2$. The extending portion of the suture 97 on the A end portion 97a side, which corresponds to the needle 98 side, is seized with the A forceps 93.

Figure 29:
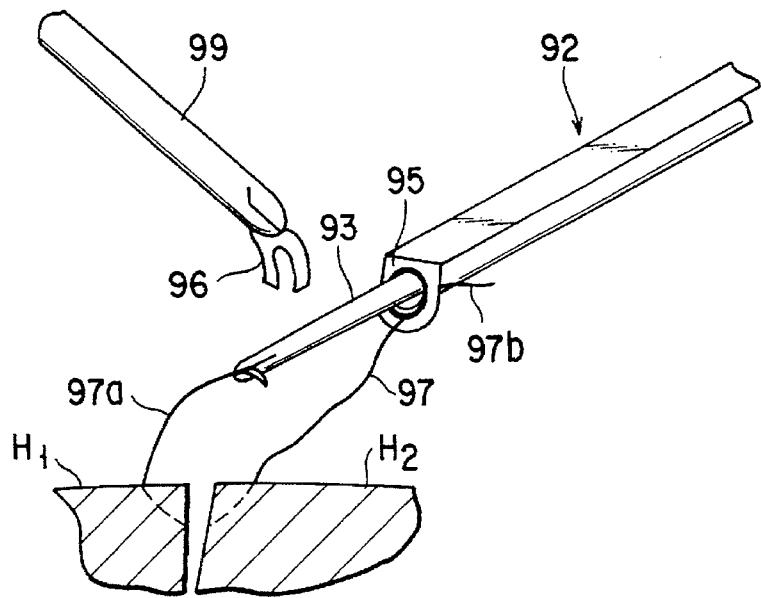
FIG. 29 is a perspective view showing a state wherein a retaining film is separated by clamping the tag with the second forceps.

A second forceps (to be referred to as a B forceps hereinafter) 99 is inserted as shown in FIG. 29. The tag 96c of the retaining film 96 is seized with the B forceps 99 to separate the retaining film 96 from the base film 95. The retaining film 96 is finally recovered outside the body.

Figure 30:
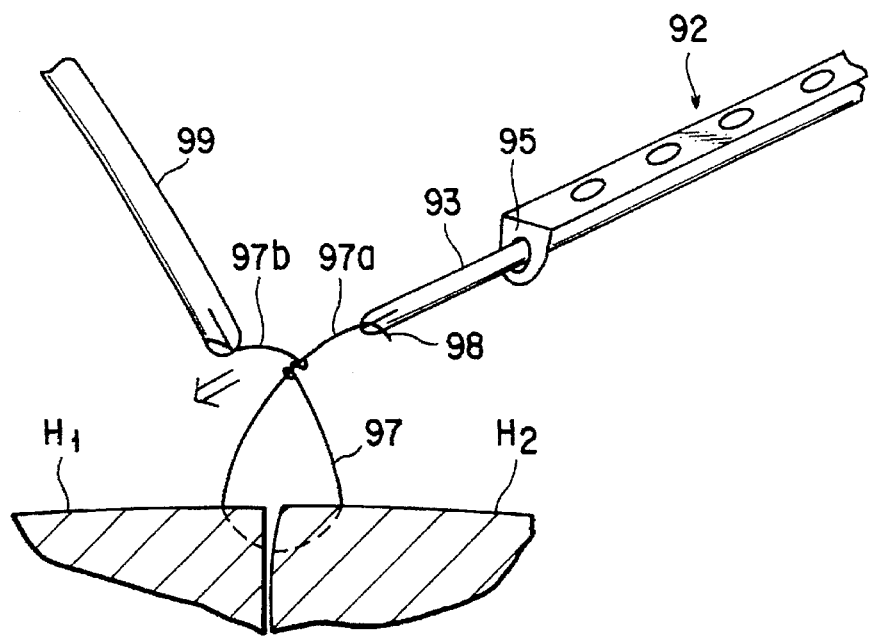
FIG. 30 is a perspective view showing a state wherein the loop portion is moved from the circumferential portion of the first forceps to the portion to be sutured by clamping the extending portion on its B end portion side with the second forceps.

As shown in FIG. 30, the extending portion of the loop portion 97L as the other end portion of the suture 97 on its B end portion 97b side is seized with the B forceps 99, and the loop portion 97L is moved from a location around the A forceps 93 to the suturing portion. In this state, the suture 97 is pulled by the A and B forceps 93 and 99, thereby fastening the suture 97 with a desired strength. A first-stitch suturing operation is thus completed.

When the suturing portion is to be consecutively sutured, the same operation as described above is performed by using a next film unit 91 of the film unit coupling body 92. Then, the film units 91 of the film unit coupling body 92 are sequentially used in the same manner as described above, thereby continuously performing suture.

The above arrangement has the following effect. Namely, since each film unit 1 of the film unit coupling body 92 is constituted by the base film 95 and the retaining film 96 both made of thin films, and the suture 97 sandwiched between the films 95 and 96, even a curved forceps 93 can be easily passed through the forceps insertion port 94.

Since each film unit 91 of the film unit coupling body 92 has a high flexibility, the film unit coupling body 92 can be inserted from the same trocar for the forceps 93 while the film unit coupling body 92 is housed in the gap between the A forceps 93 and the trocar. Thus, an insertion hole need not be formed in the patient's body wall to allow insertion of a suturing instrument through the body wall, so that the number of holes to be formed in the patient's body wall can be decreased, thereby decreasing load to the patient.

Since the large number of film units 91 are housed in the film unit coupling body 92, one-stitch suturing can be repeatedly performed without extracting or inserting the forceps 93 from and into the body cavity with a cumbersome operation. Thus, knots for suturing a comparatively large area can be easily formed, thus improving efficiency of the transfixion suture operation.

The retaining film 96 of the film unit 91 may be made of a safe biologically absorbable material. In this case, since the retaining film 96 can be left in the body, a cumbersome operation of recovering the retaining film 96 outside the body in the last stage of the transfixion suture operation can be omitted, further improving the operation efficiency of the transfixion suture operation.

One end portion of a recovering cord may be coupled to the retaining film 96, and the other end portion of the recovering cord may be held as it extends outside the body. In this case, after the retaining film 96 is removed, the recovering cord is pulled to recover the retaining film 96 outside the body. Thus, the retaining film 96 can be recovered easily.

FIGS. 31A to 31D show the third embodiment of the present invention. In this embodiment, a substantially tape-like film unit coupling body 102 obtained by continuously connecting a large number of film units 101 in a row, in the same manner as in the second embodiment, is provided. A forceps insertion port 104 for allowing insertion of a forceps 103 therethrough is formed at the central portion of each film unit 101.

As shown in FIG. 31C, each film unit 101 is constituted by a base film 105, a retaining film 106, and a suture 107. The retaining film 106 does not have a tag corresponding to the tag 96c of the second embodiment, and a hatched range in the upper end portion of the retaining film 106 in FIG. 31C is integrally bonded to the base film 105.

A slot 106b is formed in the retaining film 106 to extend from the lower end portion of a film main body 106a to a position corresponding to the forceps insertion port 104 at substantially the central portion of the retaining film 106. The entire retaining film 106 has a substantially inverted U shape.

A loop portion 107L similar to the loop portion 7L shown in FIG. 3 is provided to the suture 107. A needle 108 is coupled to the distal end of the extending portion, as one end portion, of the loop portion 107L on an A end portion 107a side. The suture 107 is accommodated as it is sandwiched between the base film 105 and the retaining film 106 such that the center of the loop portion 107L and the forceps insertion port 104 coincide.

As shown in FIG. 31A, the needle 108 is arranged on the retaining film 106 at a position that divides the forceps insertion port 104 of the film unit 101 into two portions, and two end portions 108a and 108b of the needle 108 are adhered on the film unit 101 such that they can be readily removed by lightly pulling the needle 108.

The operation of the above arrangement will be described. When the film unit 101 is to be used, the film unit coupling body 102 of the film units 101 and the forceps 103 are inserted into the body cavity through a trocar 109, as shown in FIG. 31D. The forceps 103 is half opened, and is inserted into the forceps insertion port 104 from the base film 105 side.

At this time, the needle 108 is inserted into the half open portion of the forceps 103 to be inserted. As the forceps 103 is pushed out, the needle 108 is separated from the film unit 101, as shown in FIG. 31B. The extending portion side of the suture 107 on its A end portion 107a side is pulled out together with the needle 108.

The needle 108 is securely held by the forceps 103 and is pierced into the tissue, and the forceps 103 is transferred to the A end portion 107a of the suture 107 on its needle 108 side. In this state, a B end portion 107b as the other end portion of the suture 107 is held by a B forceps different from the forceps 103, and is pulled to extract the loop portion 107L from a portion between the retaining film 106 and the base film 105, thereby moving the loop portion 107L from a location around the forceps 103 to the suturing portion. The suture 107 is pulled by the A forceps 103 and the B forceps to fasten the suture 107 with a desired strength, thereby forming a knot.

A first-stitch suturing operation is thus completed.

When the suturing portion is to be consecutively sutured, the same operation as that described above is performed by using a next film unit 101 of the film unit coupling body 102. Continuous suture can be performed by sequentially using the film units 101 of the film unit coupling body 102 in the same manner.

The above arrangement has the following effect. More specifically, in this embodiment, as the retaining film 106 need not be separated from the base film 105 unlike in the second embodiment, the suturing operation can be performed further easily as compared to that in the second embodiment.

Since the retaining film 106 is not separated from the film unit 101, it need not be recovered at the last stage. Since a portion of the suture 107 excluding its two end portions is entirely accommodated as it is sandwiched between the base film 105 and the retaining film 106, the suture 107 will not interfere with the operation of the forceps 103.

Since the needle 108 is fixed on the retaining film 106, the needle 108 will not be held as it projects to the outside, and the needle 108 can be prevented from being caught by a nearby living body tissue and the like while the film unit 101 is being inserted into a target portion in the body cavity.

FIG. 32 shows the first modification of the suturing instrument. This suturing instrument is provided with a suturing instrument main body 112 into which a forceps 111 is to be inserted, and a reducer 113 detachably mounted on the suturing instrument main body 112.

The suturing instrument main body 112 has substantially the same arrangement as the suture holding member 1 of the first embodiment. A reducer coupling portion 114 projects from the end portion of an outer cylinder 3, on its forceps fixing portion 8 side, of the suturing instrument main body 112. The reducer coupling portion 114 has a smaller diameter than that of the outer cylinder 3. An annular engaging groove 115 is formed in the outer circumferential surface of the reducer coupling portion 114.

A cylindrical body 116 having substantially the same diameter as that of the outer cylinder 3 of the suturing instrument main body 112 is provided to the reducer 113. An engaging portion 117 to be detachably engaged with the reducer coupling portion 114 of the suturing instrument main body 112 is formed on the front end portion of the cylindrical body 116. A coupling portion 118 to be detachably coupled to a trocar 121 shown in FIG. 33A is formed on the rear end portion of the cylindrical body 116. A seal member 118a is formed on the inner circumferential portion of the coupling portion 118 of the cylindrical body 116. When the forceps 111 is inserted into the reducer 113, the seal member 118a slidably contacts the forceps 111 to seal the gap between the reducer 113 and the forceps 111.

The trocar 121 is an instrument which is used in a technique for supplying a gas into the body cavity to keep a space, thereby enabling approach from the outside to the interior of the body and vice versa. The trocar 121 is provided with a cannula 122 and an inner needle (not shown) detachably inserted into the cannula 122.

A forceps insertion port body 123 is formed at the proximal end portion of the cannula 122. A movable valve 124 is provided in the forceps insertion port body 123 to prevent gas leakage from the body cavity, thereby maintaining air-tightness of a forceps insertion port 123a.

The movable valve 124 is axially supported to be pivotal about a pivot shaft 125. The movable valve 124 is normally biased by a biasing means, e.g., a spring (not shown), in a direction to close the forceps insertion port 123a. As shown in FIG. 33A, when the forceps 111 is not inserted in the trocar 121, the forceps insertion port 123a is closed by the movable valve 124, thereby maintaining air-tightness of the forceps insertion port 123a.

As shown in FIG. 33B, when the forceps 111 is inserted into the trocar 121, the movable valve 124 is pushed downward by the distal end portion of the inserting portion of the forceps 111 against the biasing force, thereby opening the forceps insertion port 123a. An instrument coupling portion 126 to be detachably coupled to the coupling portion 118 of the reducer 113 is formed on the upper end portion of the forceps insertion port body 123.

A method of using this suturing instrument will be described. First, as shown in FIG. 32, while the reducer 113 is coupled to the suturing instrument main body 112, the forceps 111 is inserted in the suturing instrument main body 112 through the interior of the reducer 113.

As the forceps 111 is inserted into the suturing instrument main body 112 and the outer cylinder 3 of the suturing instrument main body 112 is mounted on the forceps 111, a loop portion 7L of a suture 7 wound on a suture winding portion 5 of an inner cylinder 2 of the suturing instrument main body 112 is removed from the suture winding portion 5 of the inner cylinder 2 while maintaining its original shape, and is wound on the forceps 111 which is inserted to replace the inner cylinder 2.

As shown in FIG. 34A, the forceps 111 on which the outer cylinder 3 is mounted is inserted in the trocar 121. In this case, the movable valve 124 is pushed downward by the distal end portion of the inserting portion of the forceps 111 against the biasing force, thereby opening the forceps insertion port 123a.

As the forceps 111 is inserted further deeply, the coupling portion 118 of the reducer 113 is engaged with the instrument coupling portion 126 of the trocar 121, and the reducer 113 is fixed to the trocar 121, as shown in FIG. 34B. At this time, the movable valve 124 is held in an open state by the reducer 113.

After the reducer 113 is fixed to the trocar 121, when the forceps 111 is further inserted into the trocar 121, the outer cylinder 3 of the suturing instrument main body 112 is separated from the reducer 113.

Therefore, the outer cylinder 3 of the suturing instrument main body 112 is inserted in the body cavity through the cannula 122 of the trocar 121, and simultaneously the movable valve 124 of the trocar 121 is held in an open state by the reducer 113. At this time, the seal member 118a of the reducer 113 slidably contacts the forceps 111 to maintain the air-tightness of the body cavity.

When the forceps 111 is to be extracted from the trocar 121, as the forceps 111 is extracted, the outer cylinder 3 of the suturing instrument main body 112 and the reducer 113 are coupled, and then the suturing instrument main body 112 is extracted from the trocar 121. When the entire portion of the forceps 111 is extracted from the trocar 121, the movable valve 124 of the trocar 121 is closed, so that air-tightness of the body cavity is maintained.

Thus, in the above embodiment, even if the trocar 121 to be used and the inserting instrument, e.g., the forceps 111, have different diameters, this situation can be easily coped with by using the suturing instrument main body 112 having the above arrangement, thereby widening the application range of the suturing instrument.

FIG. 35 shows the first modification of the suturing instrument shown in FIG. 32. In this modification, a cylindrical reducer coupling portion 131 is formed at the end portion of an outer cylinder 3, on its forceps fixing portion 8 side, of a suturing instrument main body 112, and a cylindrical outer-fitting portion 132 is formed at the front end portion of a cylindrical body 116 of a reducer 113 to be disengageably fitted on the reducer coupling portion 131 of the suturing instrument main body 112 through frictional engagement.

Therefore, in this case, the structure of the coupling portion between the suturing instrument main body 112 and the reducer 113 can be simplified, thereby decreasing the manufacturing cost of the entire suturing instrument.

FIG. 36 shows the second modification of the suturing instrument shown in FIG. 32. In this modification, a male thread portion 133 is formed on the outer circumferential surface of the reducer coupling portion 131 of the suturing instrument main body 112 identical to that of the suturing instrument shown in FIG. 35, and a female thread portion 134 is formed on the inner circumferential surface of the outer-fitting portion 132 at the front end portion of a reducer coupling portion 131 to be threadably mounted with the male thread portion 133 of the reducer coupling portion 131 of the suturing instrument main body 112. In this case, the reliability of the coupling structure of the suturing instrument main body 112 and the reducer 113 can be improved.

FIGS. 37A and 37B show the second modification of the suturing instrument. In this modification, a suturing instrument main body 141 having the function of a forceps is provided. More specifically, as shown in FIG. 37A, an inserting portion 142 and an operating portion 143 coupled to the end portion of the inserting portion 142 on its operator's hand side are provided to the suturing instrument main body 141 of this modification.

An outer cylinder 144 and a forceps-function portion 145 disposed in the outer cylinder 144 are provided to the inserting portion 142 of the suturing instrument main body 141. A tubular stationary shaft body 146 and an operational shaft 147, disposed in the axial portion of the stationary shaft body 146 to be movable forward/backward, are provided to the forceps-function portion 145.

A stationary gripping member 149 of a gripping portion 148 of the forceps is provided at the distal end portion of the stationary shaft body 146, and a movable gripping member 150 which can be opened/closed with respect to the stationary gripping member 149, is pivotally coupled to the stationary gripping member 149 through a coupling pin (not shown).

An operational lever 151, which opens/closes the movable gripping member 150 of the gripping portion 148 through the operational shaft 147, is provided to the operating portion 143. As the operational lever 151 is operated, the movable gripping member 150 is opened/closed with respect to the stationary gripping member 149, so that a forceps-like function which is the same as that of a forceps can be obtained.

As shown in FIG. 37B, a small-diameter portion 152 is provided, on the rear side of the stationary gripping member 149, on the outer circumferential surface of the distal end portion of the stationary shaft body 146. A tapered surface is formed on the small-diameter portion 152, such that the diameter of the small-diameter portion 152 is gradually increased toward the distal end thereof. Thus, the small-diameter portion 152 is smoothly coupled to the stationary gripping member 149 on the distal end portion side of the stationary shaft body 146.

Furthermore, a loop portion 154L of a needle-attached suture 154 having one end portion coupled with a needle 153 is wound on the outer circumferential surface of the small-diameter portion 152 of the stationary shaft body 146. The loop portion 154L of the needle-attached suture 154 is wound on the small-diameter portion 152 of the stationary shaft body 146 in the same manner as the loop portion 7L shown in FIG. 3.

The outer cylinder 144 of the suturing instrument main body 141 is mounted on the stationary shaft body 146 to be movable backward/forward in the axial direction. A biasing spring 155 is mounted on the rear end portion of the outer cylinder 144. The biasing spring 155 biases the outer cylinder 144 forward toward the stationary shaft body 146. Normally, the small-diameter portion 152 of the stationary shaft body 146 is openably/closably covered with the distal end portion of the outer cylinder 144 by the spring force of the biasing spring 155.

A trigger 156 is provided at the rear end portion of the outer cylinder 144 to slide the outer cylinder 144 in the axial direction with respect to the stationary shaft body 146. A suture fixing groove 157 is formed by incision in the distal end portion of the outer cylinder 144. The two end portions of the needle-attached suture 154 wound on the small-diameter portion 152 of the stationary shaft body 146 are inserted in and locked by the suture fixing groove 157.

The operation of the above arrangement will be described. First, the inserting portion 142 of the suturing instrument main body 141 is inserted into the body cavity through, e.g., a trocar. The movable gripping member 150 of the gripping portion 148 is operated by the operational lever 151 of the operating portion 143 of the operating portion 143, so that it is opened/closed with respect to the stationary gripping member 149 to seize the needle 153. The needle 153 is passed through the wounded portion, and the suture 154 is passed through the tissue.

An A end portion 154a of the suture 154 on its needle 153 side, which has passed through the tissue, is seized by the gripping portion 148 of the suturing instrument main body 141. Thereafter, a B end portion 154b of the needle-attached suture 154 on its other end portion side is seized by another B forceps.

In this state, the trigger 156 of the outer cylinder 144 is pulled to expose the small-diameter portion 152 of the stationary shaft body 146. The suture 154 is pulled by another B forceps to slide its loop portion 154L toward the distal end side of the stationary shaft body 146.

The loop portion 154L of the suture 154 slides on the tapered surface of the small-diameter portion 152 and is removed from the distal end of the stationary shaft body 146. At this time, since the gripping portion 148 of the suturing instrument main body 141 seizes the A end portion 154a of the suture 154 on its needle 153 side, the A end portion 154a of the suture 154 on its needle 153 side passes through the loop portion 154L of the suture 154. In this state, the suturing instrument main body 141 and another B forceps are respectively pulled to fasten a knot, thereby ending the first-stitch suturing operation.

The above arrangement has the following effect. More specifically, since the suturing instrument main body 141 is provided with the function of the forceps, it can be sufficiently used as a forceps. For this reason, the suturing instrument main body 141 need not be mounted on another forceps or the like but can be used as it is, thereby improving the operability of the suturing instrument.

Since the loop portion 154L of the needle-attached suture 154 wound on the outer circumferential surface of the small-diameter portion 152 of the stationary shaft body 146 is normally covered with the outer cylinder 144, when the suturing instrument main body 141 is to be inserted into, e.g., a trocar, the knot of the loop portion 154L of the needle-attached suture 154 will not be shifted or untied.

Since another forceps or the like need not be inserted in the suturing instrument main body 141 and a mechanism for sliding the outer cylinder 144 of the suturing instrument main body 141 is provided, the inserting portion 142 of the suturing instrument main body 141 can be made thin. Therefore, the suturing instrument main body 141 can be used for a small-diameter trocar as well.

FIGS. 38A and 38B show the third modification of the suturing instrument. In this modification, as shown in FIG. 38B, the suturing instrument is provided with a suture fixing cylinder 162 which is used in combination with a forceps 161 or the like.

The suture fixing cylinder 162 is made of a cylindrical body having a sufficiently small thickness. The diameter of the inner cavity of the suture fixing cylinder 162 is set to be slightly smaller than the outer diameter of the forceps 161 which is to be used in combination with the suture fixing cylinder 162. The suture fixing cylinder 162 has an elasticity enough to be lightly close-fitted on the outer circumferential surface of the forceps 161.

A suture fixing portion 163 projects from one end portion of the suture fixing cylinder 162. The suture fixing portion 163 can be deformed with an appropriate force. A suture fixing groove 164 is formed in the suture fixing portion 163 by incision.

The operation of the above arrangement will be described. When the suture fixing cylinder 162 is used, it is used in combination with the forceps 161 and the like. The forceps 161 is inserted from the rear end of the suture fixing cylinder 162 and is arranged at an appropriate position on the forceps 161. At this time, the suture fixing cylinder 162 is fixed on the forceps 161 with a light close-fitted state.

In this state, a loop portion 166L of a needle-attached suture 166 having one end portion coupled to a needle 165 is wound on the forceps 161, and the two ends of the suture 166 are caused to be held by the suture fixing groove 164 of the suture fixing portion 163. The loop portion 166L of the suture 166 at this time is wound on the forceps 161 in the same manner as the loop portion 7L shown in FIG. 3. The manner to wind the loop portion 166L of the suture 166 is not particularly limited, but can be of any type as far as a knot can be formed.

As shown in FIG. 38B, the loop portion 166L of the needle-attached suture 166 is arranged below the suture fixing portion 163. Hence, the loop portion 166L of the suture 166 is fixed as it is sandwiched between the forceps 161 and the suture fixing portion 163.

The forceps 161 prepared in this manner is inserted into the body cavity through a trocar or the like. After this, the suture 166 is ligated in accordance with the same operation as that of the first embodiment.

In the above arrangement, since the suture fixing cylinder 162 is made of a cylindrical round tube having a sufficiently small thickness, the forceps 161 on which the suture fixing cylinder 162 is mounted can also be inserted in a small-diameter trocar.

FIG. 39 shows a suture winding unit 171 of the suture holding member 1 according to the first embodiment. This suture winding unit 171 has three film-like saucer portions 172a, 172b, and 172c.

The first saucer portion 172a is coupled to the second saucer portion 172b such that the former can be bent back to overlap the latter through a first coupling portion 173a. Similarly, the third saucer portion 172c is coupled to the second saucer portion 172b such that the former can be bent back to overlap the latter through a second coupling portion 173b. The centers of the three saucer portions 172a, 172b, and 172c are arranged at vertices of a triangle.

Figure 45:
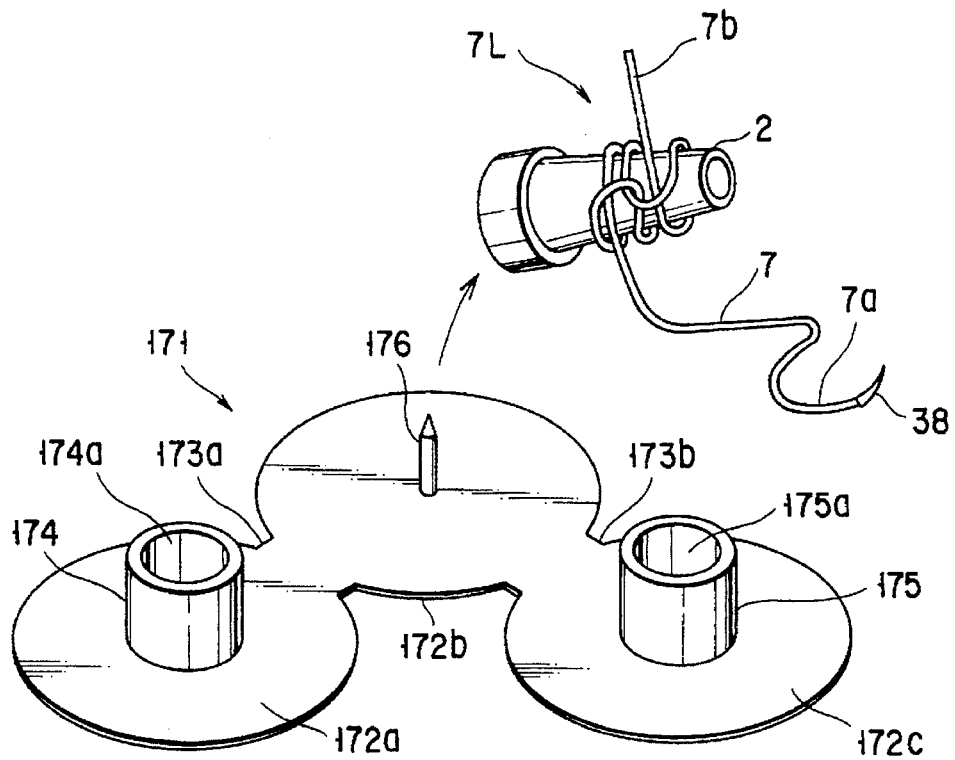
FIG. 45 is a perspective view showing a state wherein the inner cylinder is removed from the suture winding unit together with the suture.

As shown in FIG. 45, an inner cylinder mounting portion 176, on which the inner cylinder 2 of the suture holding member 1 of the suturing instrument according to the first embodiment can be detachably mounted, is provided upright on the second saucer portion 172b. First and second cylindrical bodies 174 and 175 are fixed respectively on the first and third saucer portions 172a and 172c. The inner cylinder 2 of the suture holding member 1 can be inserted in each of inner-cylinder spaces 174a and 175a of the first and second cylindrical bodies 174 and 175.

A method of using the suture winding unit 171 will be described. As shown in FIG. 40, a suture 7 is sequentially wound on the second cylindrical body 175 of the third saucer portion 172c, the first cylindrical body 174 on the first saucer portion 172a, and the inner cylinder 2 on the second saucer portion 172b to form three loops $7L_3$, $7L_2$, and $7L_1$, respectively.

Figure 41:
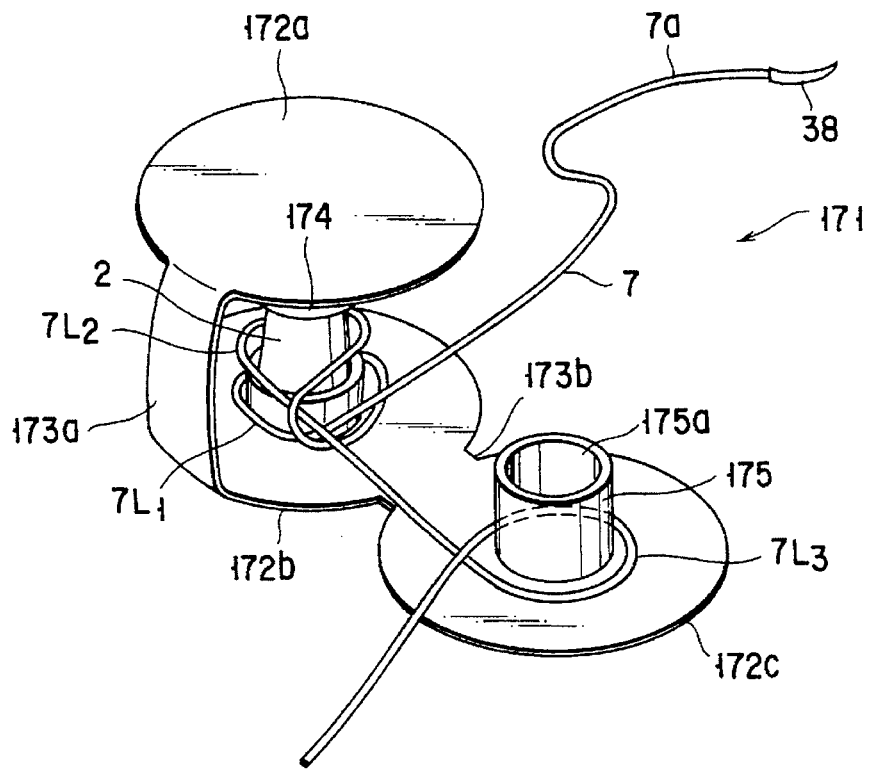
FIG. 41 is a perspective view showing a state wherein the first cylinder is fitted on the inner cylinder to move the second loop to the inner cylinder.

Subsequently, as shown in FIG. 41, the first saucer portion 172a is bent back to overlap the second saucer portion 172b through the first coupling portion 173a, so that the first cylindrical body 174 is fitted on the inner cylinder 2, and the second loop $7L_2$ is moved from the first cylindrical body 174 to the inner cylinder 2.

Figure 42:
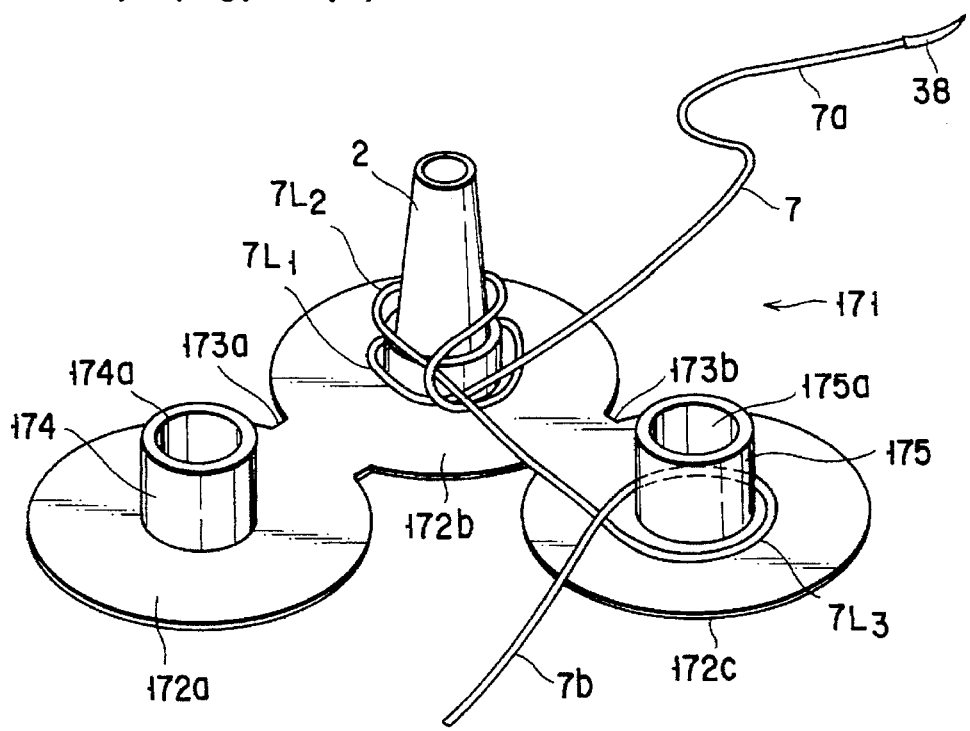
FIG. 42 is a perspective view showing a state wherein the first cylinder is restored to the original position.

After the second loop $7L_2$ is moved, the first saucer portion 172a is returned to the original position, as shown in FIG. 42. Then, as shown in FIG. 43, the third saucer portion 172c is bent back to overlap the second saucer portion 172b through the second coupling portion 173b, so that the second cylindrical body 175 is fitted on the inner cylinder 2, and the third loop $7L_3$ is moved from the second cylindrical body 175 to the inner cylinder 2.

After the third loop $7L_3$ is moved, the third saucer portion 172c is returned to the original position, as shown in FIG. 44. At this time, a loop portion 7L is formed on the inner cylinder 2 as it is obtained by winding the suture 7 in the same manner as in FIG. 3.

Figure 46:
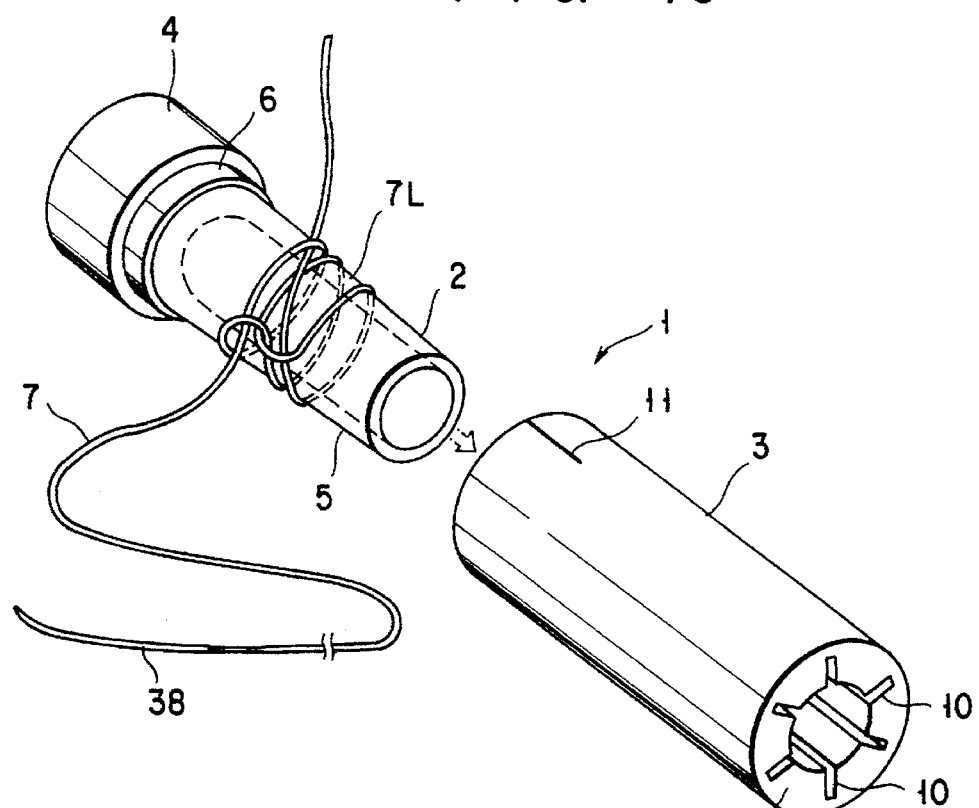
FIG. 46 is a perspective view showing a state before the inner cylinder, on which the suture is wound, and the outer cylinder are assembled together.

Finally, the inner cylinder 2 is removed from the inner cylinder mounting portion 176 of the second saucer portion 172b together with the suture 7, as shown in FIG. 45, and the outer cylinder 3 is mounted on the inner cylinder 2, as shown in FIG. 46. Thus, the suture holding member 1 shown in the first embodiment is assembled.

In the above embodiment, since an exclusive suture 7 is not wound on the inner cylinder 2 of the suture holding member 1 in advance, an arbitrary existing suture 7 can be used. For this reason, the suture 7 can be saved. Since the loop portion 7L of the suture 7 as shown in FIG. 3 can be easily and reliably formed, the loop portion 7L to form a knot can be easily arranged on, e.g., a forceps.

Figure 47:
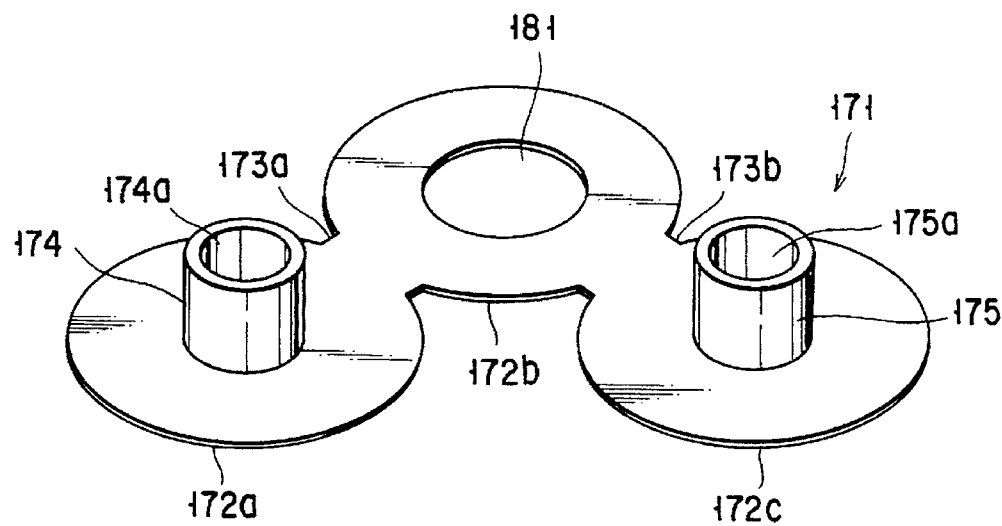
FIG. 47 is a perspective view showing a modification of the suture winding unit shown in FIG. 39.

FIG. 47 shows a modification of the suture winding unit 171. In this modification, an insertion hole 181, through which the stationary shaft body 146 of the suturing instrument main body 141 shown in FIGS. 37A and 37B is inserted, is formed in a saucer portion 172b of a suture winding unit 171 corresponding to that shown in FIG. 39.

The operation of the above arrangement will be described. First, the trigger 156 of the outer cylinder 144 of the suturing instrument main body 141 is pulled to expose the small-diameter portion 152 of the stationary shaft body 146. In this state, the stationary shaft body 146 is inserted in the insertion hole 181 of the second saucer portion 172b from below, and the small-diameter portion 152 is pulled up to the upper side of the second saucer portion 172b.

Subsequently, a suture 154 is sequentially wound on a second cylindrical body 175 on a third saucer portion 172c, a first cylindrical body 174 on a first saucer portion 172a, and the small-diameter portion 152 of the stationary shaft body 146 on the second saucer portion 172b in accordance with the same procedure as the suture winding operation of the suture winding unit 171 described above, thus forming three loops.

Figure 48:
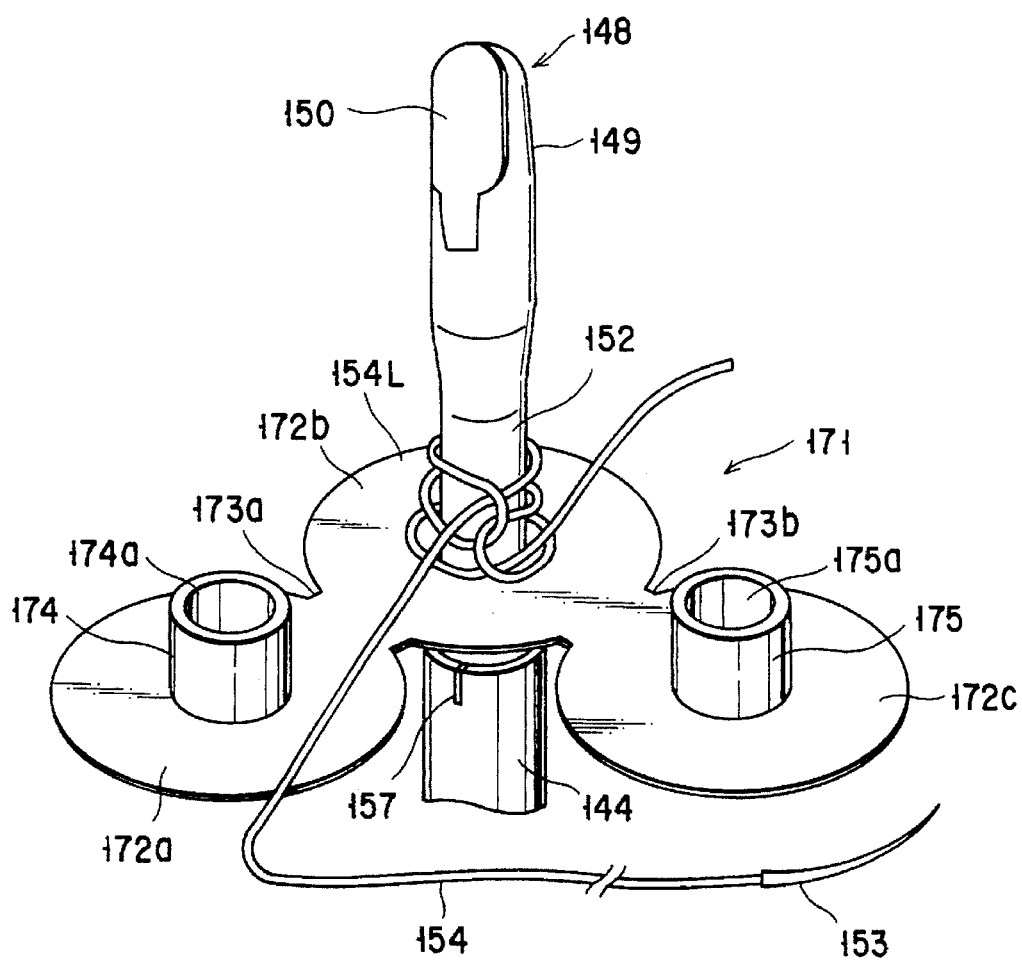
FIG. 48 is a perspective view showing a state wherein the three loops are moved to the forceps.

Thereafter, the first and third saucer portions 172a and 172c are moved in accordance with the same procedure as the suture winding operation described above, so that the three loops are moved to the small-diameter portion 152 of the stationary shaft body 146, as shown in FIG. 48.

Subsequently, the two end portions of a loop portion 154L of the suture 154 on the small-diameter portion 152 of the stationary shaft body 146 are fixed in a suture fixing groove 157 of the outer cylinder 144. In this state, the outer cylinder 144 is returned to the original position, and the loop portion 154L is housed in the outer cylinder 144.

Thereafter, the small-diameter portion 152 of the stationary shaft body 146 is extracted through the insertion hole 181 of the second saucer portion 172b together with the suture 154, thus ending the operation of winding the loop portion 154L of the suture 154 onto the suturing instrument main body 141.

In the above arrangement, the operation of winding the loop portion 154L of the suture 154 on the small-diameter portion 152 of the stationary shaft body 146 of the suturing instrument main body 141 shown in FIGS. 37A and 37B can be performed easily, so that its operability is improved.

Alternatively, the loop portion 166L of the suture 166 may be wound on the forceps 161, on which the suture fixing cylinder 162 shown in FIG. 38A is mounted, by utilizing the suture winding unit 171 shown in FIG. 47.

FIGS. 49 to 62 show the fourth embodiment of the present invention.

Figure 49:
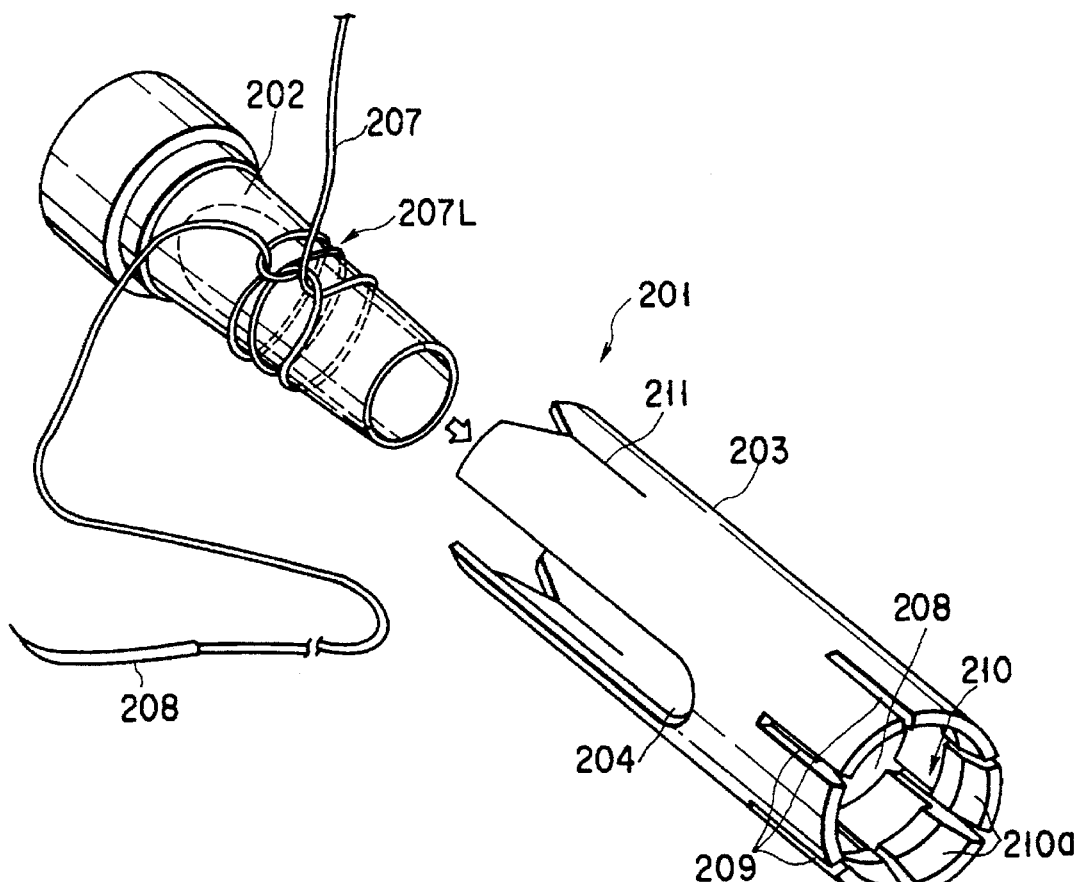
FIG. 49 is an exploded perspective view showing a suture holding member according to the fourth embodiment of the present invention.
Figure 50:
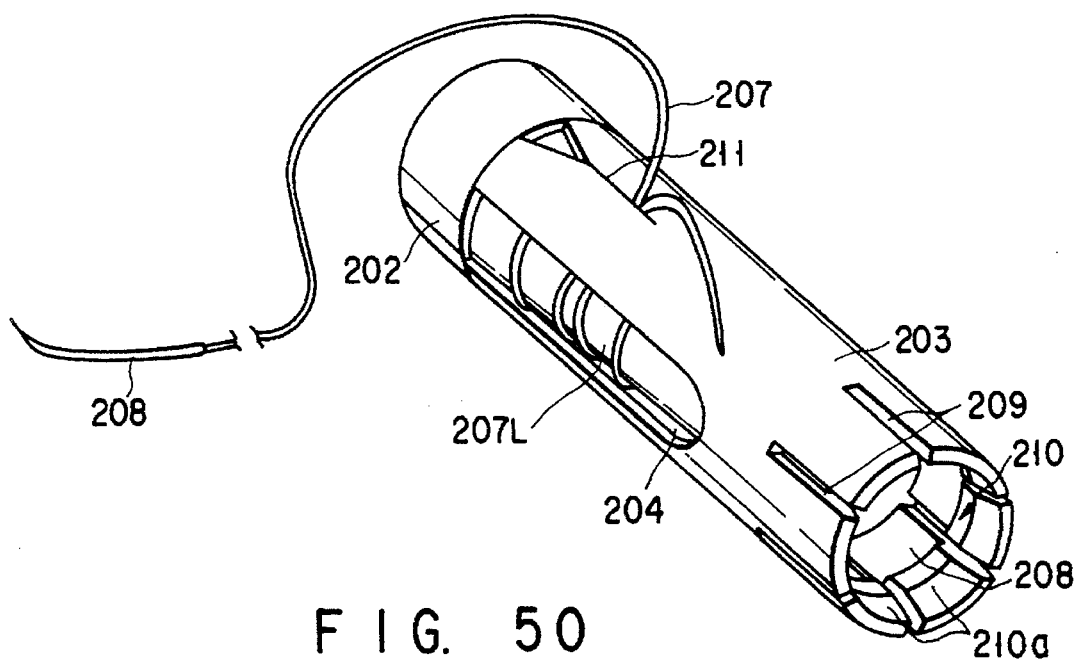
FIG. 50 is a perspective view showing a state wherein the inner cylinder of the suture holding member shown in FIG. 49 is fitted and fixed in the outer cylinder.

As shown in FIGS. 49 and 50, a suture holding member 201 of the suturing instrument of this embodiment has an inner cylinder 202, an outer cylinder 203, and a suture 207 in almost the same manner as in the first embodiment shown in FIG. 1. In the following, mainly, features differed from that of the first embodiment will be described.

In this embodiment, unlike in the first embodiment, a needle 208 is attached in advance to one end side of the suture 207. The suture 207 is wound, in accordance with the principle of winding described in the first embodiment, in a direction opposite to that of the first embodiment. The two end portions of the suture 207 extending from a loop portion 207L are fixed in one suture locking groove 211 in the same manner as in the modification shown in FIG. 12. Two windows or openings 204 are formed in the side portions of the outer cylinder 203. The inner diameter of a forceps insertion port 208 is set to be larger than the outer diameter of a forceps on which the outer cylinder 203 is to be mounted.

A latch portion 210 to be latch-engaged with an adaptor to be described later is provided near the forceps insertion port 208. The latch portion 210 has projections 210a having a trapezoidal section and projecting into the forceps insertion port 208. The projections 210a are separated from each other by grooves 209 formed at an almost equal angular interval in the circumferential direction, so that they can be easily elastically deformed. The surface portion of the outer cylinder 203 is colored in black or roughened. Excluding these respects, the fourth embodiment is almost the same as the first embodiment.

FIG. 51 shows an adaptor 220 used for fixing the outer cylinder 203 of this suturing instrument on a forceps.

The adaptor 220 has a sheath portion 221 and a forceps fixing portion 222, as shown in FIG. 51. The sheath portion 221 has an inner diameter larger than the outer diameter of the forceps and an outer diameter enough to be inserted into a trocar. The outer diameter of the sheath portion 221 is almost equal to or slightly larger than that of the outer cylinder 203 of the suturing instrument.

An outer cylinder fixing portion 223 is arranged at the distal end portion of the sheath portion 221. The outer cylinder fixing portion 223 meshes with the latch portion 210 of the outer cylinder 203, thus fixing the outer cylinder 203 through the latch portion 210. As shown in FIG. 51, the outer cylinder fixing portion 223 of this embodiment has a small-diameter stepped structure in which a projecting ridge 224 and a groove 225 are arranged from its distal end side. The projections 210a arranged in the latch portion 210 of the outer Cylinder 203 ride over the projecting ridge 224 and are fitted in the groove 225.

A large-diameter inner hole portion 226 and a thread portion 227 are arranged in the forceps fixing portion 222 arranged at the rear end portion of the sheath portion 221. The large-diameter inner hole portion 226 has a slightly enlarged diameter. The thread portion 227 is formed on the outer circumferential surface of the forceps fixing portion 222. A ring 228 made of an elastic material, e.g., silicone or rubber, is housed in the large-diameter inner hole portion 226. The ring 228 is formed longer than the large-diameter inner hole portion 226 along the axial direction and has an inner diameter slightly larger than the outer diameter of the forceps. A cap-like screw-in member 229 is threadably engaged on the thread portion 227. A female thread threadably engageable with the thread portion 227 is formed on the screw-in member 229. An inwardly projecting collar 230 and a forceps insertion port 231 are formed on the outer end portion of the screw-in member 229.

A transfixion suture operation using the suturing instrument of this embodiment is performed in the following manner.

First, as shown in FIG. 51, the ring 228 is mounted in the large-diameter inner hole portion 226 of the adaptor 220, and the screw-in member 229 is threadably engaged with the thread portion 227 of the forceps fixing portion 222. At this time, it is preferable that the screw-in member 229 is arranged at such a position that its collar 230 will not urge the end portion of the ring 228.

As shown in FIG. 52, a forceps 233 having a needle retainer 232 at its distal end portion is inserted through the forceps insertion port 231 of the adaptor 220, and the needle retainer 232 is caused to project from the adaptor 220. Since the inner diameter of the ring 228 is slightly larger than the outer diameter of the forceps 233, the forceps 233 can be easily inserted in the adaptor 220. Thereafter, the screw-in member 229 is screwed in to bias the ring 228 through the collar 230. Thus, the diameter of the ring 228 is reduced to clamp the outer circumferential surface of the forceps 233, so that the adaptor 220 is fixed on the forceps 233 and that the gap between the forceps 233 and the adaptor 220 is sealed.

Figure 54:
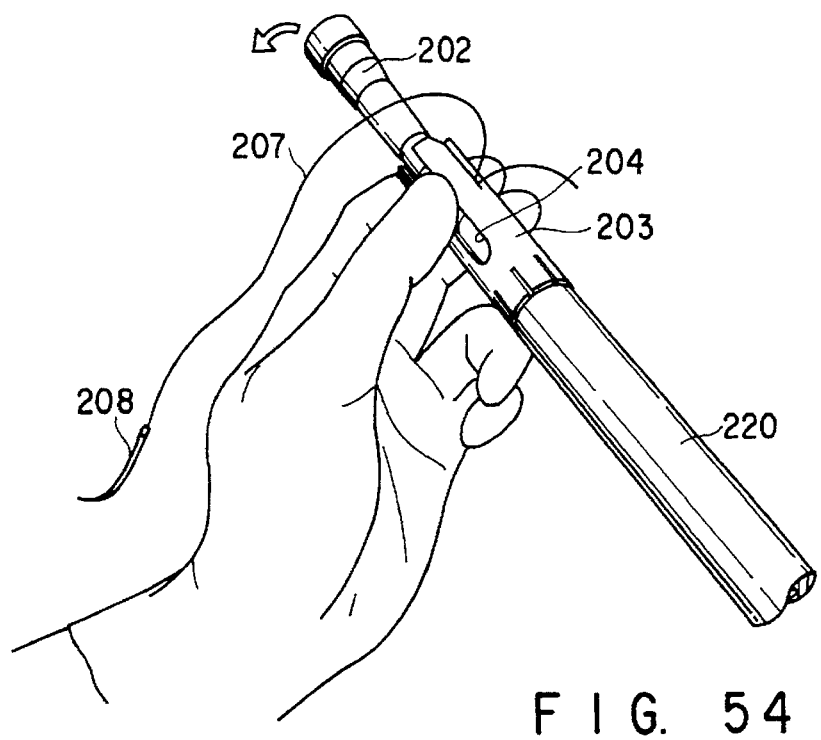
FIG. 54 is a perspective view of a state wherein the inner cylinder shown in FIG. 49 is pushed out from the outer cylinder.
Figure 55:
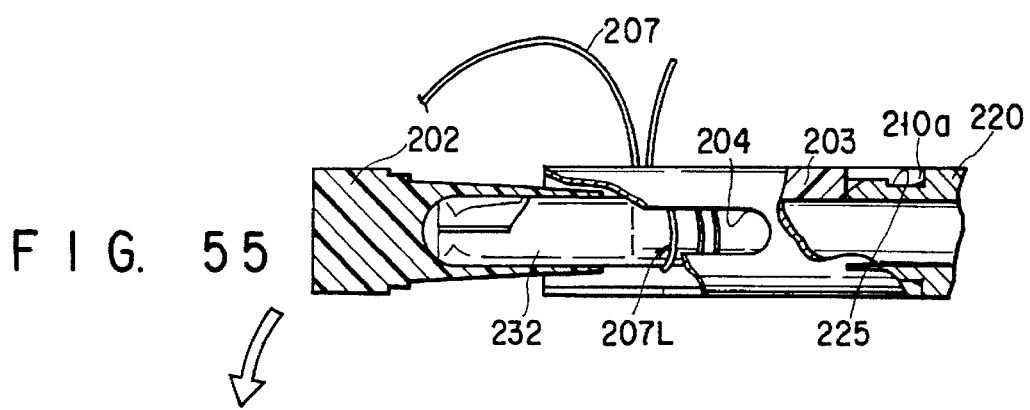
FIG. 55 is a sectional view of the state shown in FIG. 54.

In the suturing instrument, as shown in FIG. 50, the inner and outer cylinders are fitted with each other. As shown in FIG. 53, the needle retainer 232 arranged at the distal end portion of the forceps 233 is inserted through a forceps insertion port 208 of the suturing instrument. While the loop portion 207L (FIG. 49) arranged on the inner cylinder 202 is pressed through the openings 204 formed in the outer cylinder 203 as shown in FIG. 54, the inner cylinder 202 is pushed out from the outer cylinder 203, as shown in FIG. 55. Then, the loop portion 207L is transferred from the inner cylinder 202 onto the outer circumferential surface of the needle retainer 232. When the outer cylinder 203 is further pushed in toward the adaptor 220 together with the loop portion 207L, the projections 210a of the latch portion 210 ride over the projecting ridge 224 of the adaptor 220 and are fitted in the groove 225, so that the outer cylinder 203 is fixed on the adaptor 220, and on the forceps 233 accordingly.

After the loop portion 207L of the suture 207 is mounted on the forceps 233 in this manner, the needle retainer 232 at the distal end portion of the forceps 233 is inserted into the body cavity through a trocar (not shown), thus allowing a suturing operation. In this embodiment, another forceps 234 is used together with the forceps 233 on which the suture 207 is mounted.

FIGS. 56 to 62 show the procedure of the suturing operation performed by using the suturing instrument of this embodiment.

Figure 56:
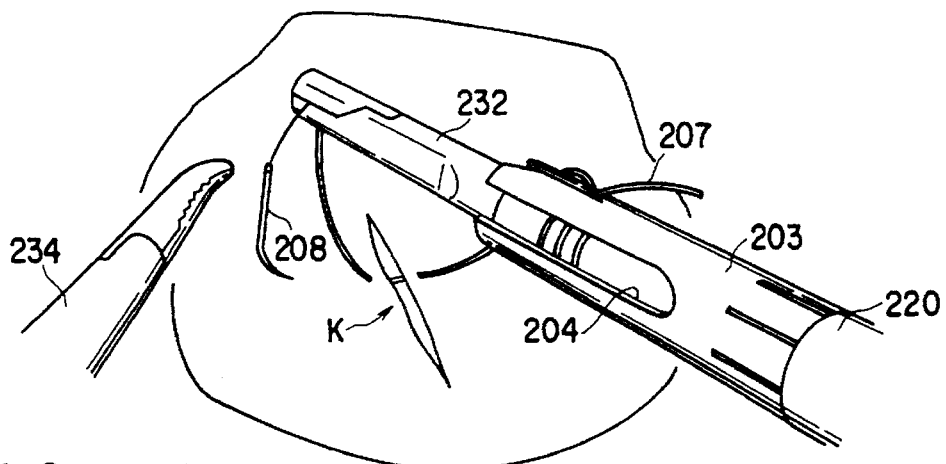
FIG. 56 is a perspective view showing a state wherein a morbid portion is sutured by using the suturing instrument shown in FIG. 49.
Figure 57:
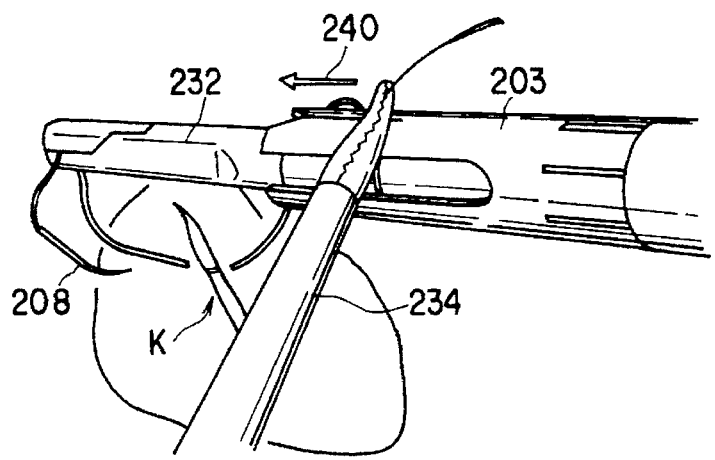
FIG. 57 is a perspective view showing a state wherein the end portion of the suture is removed from the outer cylinder of the suture holding member.
Figure 58:
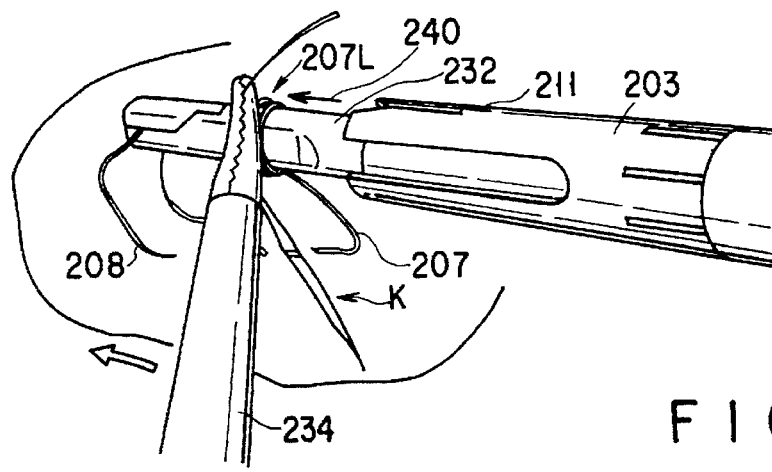
FIG. 58 is a perspective view of a state wherein the suture is removed from the outer cylinder of the suture holding member and is slid on the forceps to extract the loop.

First, as shown in FIG. 56, the needle 208 is passed through a portion K to be sutured, and the suture 207 is seized near the needle 208. Subsequently, as shown in FIG. 57, the end portion of the suture 207 on a side opposite to its end portion on which the needle 208 is mounted is seized by the forceps 234 inserted separately into the body cavity, and the forceps 234 is set toward the distal end of the needle retainer 232 and moved in a direction indicated by an arrow 240. Thus, the suture 207 is removed from the suture locking groove 211. When the forceps 234 is further moved toward the distal end of the needle retainer 232, the loop portion 207L of the suture 207 is pulled out from the outer cylinder 203, and slides on the needle retainer 232 as the forceps 234 is moved. FIG. 58 shows this state.

Figure 59:
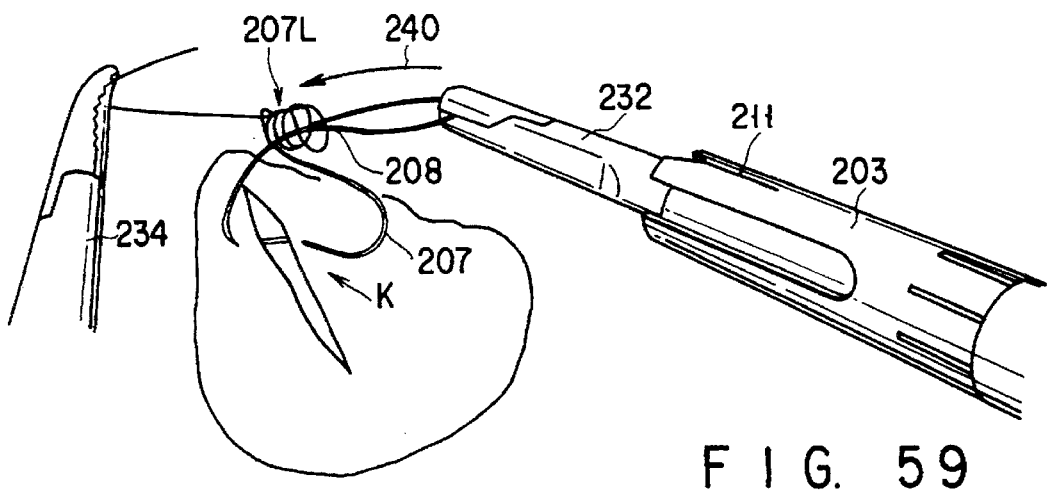
FIG. 59 is a perspective view of a state wherein a needle is passed through the loop of the suture extracted from the forceps.

As shown in FIG. 59, the forceps 234 is further moved in the direction indicated by the arrow 240 to extract the loop portion 207L of the suture 207 from the needle retainer 232. Consecutively, as shown in FIG. 59, the end portion of the suture 207 on its needle 208 side, which is gripped by the needle retainer 232, is passed through the loop portion 207L together with the needle 208.

The needle retainer 232 is moved in a direction to separate from the portion K to be sutured, as indicated by an arrow 241 in FIG. 60A, to pull the suture 207, thereby fastening the tissue of the portion K to be sutured with an appropriate force. Thus, as shown in FIGS. 60B and 60C, a loop closest to the portion K to be sutured is closed, thereby fastening the tissue of the portion K to be sutured, as in shown in FIG. 60D. When an excessive tension is applied to the tissue of the portion K to be sutured at the end of the suture 232, or the tissue of the portion K to be sutured is desired to be ligated very strongly, the suture is passed through the loop with the suture end being gripped by another forceps 234 and is hooked at the distal end of the forceps 234, and the distal end is urged against a portion near the portion K to be sutured, thereby pulling the needle retainer 121 and hence pulling this suture end, as shown in FIG. 60A. Thereafter, when another forceps 234 is moved toward an arrow 242, as indicated in FIG. 61A, a loop located on the uppermost side of FIG. 61A, which forms a loop having the suture 207 on its needle retainer 232 side as the center, as shown in FIG. 61B, is pulled in the direction indicated by the arrow 242, and is thus deformed to inversely form a loop having the suture 207 on its forceps 234 side as the center, while reducing the diameter of the loop. This state is shown in FIGS. 61C and 61D. As a result, the knot of the suture 207 becomes firmer.

Finally, as shown in FIG. 62, the needle retainer 232 and the forceps 234 are strongly pulled in opposite directions as indicated by the arrows 241 and 242, respectively, to tightly fasten the knot.

According to the suturing instrument of this embodiment, the outer cylinder 203 and the adaptor 220 are reliably and firmly fixed by latch engagement obtained by fitting the projections 210a in the groove 225, and the outer diameter of the outer cylinder 203 is formed to be substantially equal to or slightly smaller than the outer diameter of the adaptor 220. Therefore, when the suturing instrument is to be extracted from the trocar when suture is ended, the outer cylinder 203 will not drop from the trocar, so that a treatment, e.g., suture, can be performed efficiently.

The openings 204 are formed in the outer cylinder 203 that holds the suture 207. Thus, when the suture holding member 201 is to be mounted on the forceps 233, the loop portion 207L in the outer cylinder 203 is held by the operator's fingers to prevent the loop portion 207L from coming out from the outer cylinder 203 together with the inner cylinder 202, thereby mounting the suture holding member 201 efficiently. Furthermore, during suture in the body cavity, even if the loop portion 207L is closed to fasten the needle retainer 232 while the loop portion 207L is slid on the needle retainer 232 by another forceps 234, an external force can be applied to the loop portion 207L through the openings 204 to extract it from the needle retainer 232.

Since the surface portion of the outer cylinder 203 is colored in black or roughened, reflection by the outer cylinder 203 is prevented, so that the outer cylinder 203 can be clearly identified even during endoscopic treatment.

The suturing instrument can be used in combination with the adaptor 220. During a surgical operation that requires pneumoperitoneum or the like, the gap between the trocar and the needle retainer 232 is reliably sealed, so that any error in pneumoperitoneum will not occur.

FIGS. 63 to 65 schematically show a needle-attached suture suturing instrument 301 according to the fifth embodiment of the present invention. The suture suturing instrument 301 has an inner cylinder 302 and an outer cylinder 303 serving as a suture holding member. The outer cylinder 303 serving as the suture holding member holds a needle-attached suture 304 used for suturing a body tissue.

The inner cylinder 302 consists of a cylindrical suture winding portion 305 to be housed in the outer cylinder 303, a fixing portion 306 to be close-fitted on the inner wall of the outer cylinder 303, thereby fixing the inner cylinder 302, and an inner cylinder gripping portion 307 which is not housed in the outer cylinder 303. A slight tapered portion is formed on the outer side of the suture winding portion 305, so that the diameter is increased from the suture winding portion 305 toward the fixing portion 306. The suture winding portion 305 is formed cylindrically, as described above. The inner diameter of the suture winding portion 305 is larger than the diameter of a forceps serving as a surgical instrument (to be merely referred to as a forceps hereinafter) which is used in combination with the suture suturing instrument 301. The inner hole of the cylindrical portion of the suture winding portion 305 does not extend through the inner cylinder 302 but is terminated at an intermediate portion of the inner cylinder 302.

The outer cylinder 303 is formed cylindrically with a resin having an appropriate elasticity. The outer cylinder 303 has an outer diameter enough to be inserted into a trocar which is used in a laparoscopic operation and the like. The outer cylinder 303 has a suture housing portion 308 serving as a loop retaining portion for housing the loop of a suture to be described later, and a forceps fixing portion 309 for fixing the outer cylinder 303 on the forceps. The suture housing portion 308 has an inner diameter enough to be fitted on the fixing portion 306 of the inner cylinder 302 to be loosely close-fitted on it. The suture housing portion 308 has a length almost equal to the sum of the lengths of the fixing portion 306 and the suture winding portion 305 of the inner cylinder 302.

The forceps fixing portion 309 has an inner hole communicating with the suture housing portion 308. The forceps fixing portion 309 has an inner diameter smaller than the diameter of the suture housing portion 308, so that it can be close-fitted on the outer circumferential portion of a forceps to be used in combination with the suture suturing instrument 301. Six grooves 310 are formed in the forceps fixing portion 309 at an equal angular interval in the circumferential direction, and extend from the inner hole of the forceps fixing portion 309 toward the outer circumference of the outer cylinder 303. Thus, the forceps fixing portion 309 can be easily and reliably close-fitted on the outer circumferential portion of the forceps. Two incisions 311 serving as suture fixing portions are formed in the distal end portion of the suture housing portion 308 at positions opposite to each other in the radial direction to hold an end portion on its needle 304a side and the other end of the suture 304. The end portion on its needle 304a side and the other end of the needle-attached suture 304 are held in the incisions 311 of the outer cylinder 303, and a portion of the needle-attached suture 304 between the two end portions is wound on the suture winding portion 305 of the inner cylinder 302.

The basis of this winding is as shown in FIG. 66. The two ends of the suture 304 are aligned, and the aligned ends are passed through a ring R formed at that time. This winding method is similar to that shown in U.S. Pat. No. 3,580,256. When a longer end of the suture 304 shown in FIG. 66 is passed through a loop 304L and the two ends are pulled, a double ligation portion as shown in FIG. 67 can be obtained. In this embodiment, the two ends of the suture 304 are passed through the ring R twice.

In this embodiment, the suture winding portion 305 extends through the loop 304L formed by passing the two ends of the suture 304 through the ring R. At this time, the suture 304 is wound on the suture winding portion 305 such that that end of the suture 304 on the needle 304a side is wound on the suture winding portion 305 on the fixing portion 306 side and the other end side of the suture 304 is wound on the opening side of the suture winding portion 305. A method of winding the suture 304 is not limited to this but can be of any method as far as a knot is formed. In actual assembly of the inner cylinder 302, the outer cylinder 303, and the needle-attached suture 304, the suture 304 is wound on the inner cylinder 302, as shown in FIG. 64. A portion of the inner cylinder 302 on which the suture 304 is wound is inserted into the suture housing portion 308 of the outer cylinder 303. The one end of the suture 304 on the needle side and the other end of the suture 304 are sandwiched and fixed in the incisions 311 of the outer cylinder 303. Then, the fixing portion 306 of the inner cylinder 302 is fixed in the outer cylinder 303 by close-fitting, as shown in FIG. 65.

A case wherein a body tissue is to be sutured by using this suturing instrument 301 will be described with reference to FIGS. 68 to 75.

FIG. 68 shows a forceps 312 as an example of a surgical instrument on which the needle-attached suture suturing instrument 301 having the above arrangement is mounted to perform suture. To mount the suture suturing instrument 301 on the forceps 312, first, a portion of the outer cylinder 303 is held by the operator, and the distal end of the forceps 312 is inserted into the cavity in the forceps fixing portion 309 of the outer cylinder 303. The forceps 312 used in this case is preferably a needle retainer for an endoscopic operation (e.g., one shown in FIG. 68). The forceps fixing portion 309 has a diameter smaller than that of the forceps 312. Thus, although the outer cylinder 303 is fixed on the forceps 312 with close-fitting, as the outer cylinder 303 is made of a resin and has an elasticity and the grooves 310 are formed in the forceps fixing portion 309, the forceps fixing portion 309 can be moved forward/backward with an appropriate force in the axial direction of the forceps 312.

As shown in FIG. 69, when the forceps 312 inserted in the forceps fixing portion 309 is further moved forward, the distal end of the forceps 312 enters the inner hole of the suture winding portion 305 of the inner cylinder 302. When the forceps 312 is further pushed forward while holding the outer cylinder 303, the inner cylinder 302 is pushed by the forceps 312 which is inserted in the inner hole of the inner cylinder 302, as shown in FIG. 70, is removed from the outer cylinder 303 which is close-fitted on the inner cylinder 302 with the fixing portion 306, and is pushed out. At this time, the wound suture 304 is removed from the suture winding portion 305 while maintaining its original shape partly because of the tapered portion formed on the suture winding portion 305 of the inner cylinder 302, and is then wound on the forceps 312 which is inserted to replace the suture winding portion 305. The inner cylinder 302 is removed from the forceps 312. The outer cylinder 303 is moved on the forceps 312 to an appropriate position. In this state, a trocar or the like is inserted into the body cavity and the needle 304a is held by the forceps 312. Alternatively, another forceps 313 may be inserted to hold the needle 304a. Then, a portion of a living body tissue D that needs suture is sutured.

Figures 71, 72:
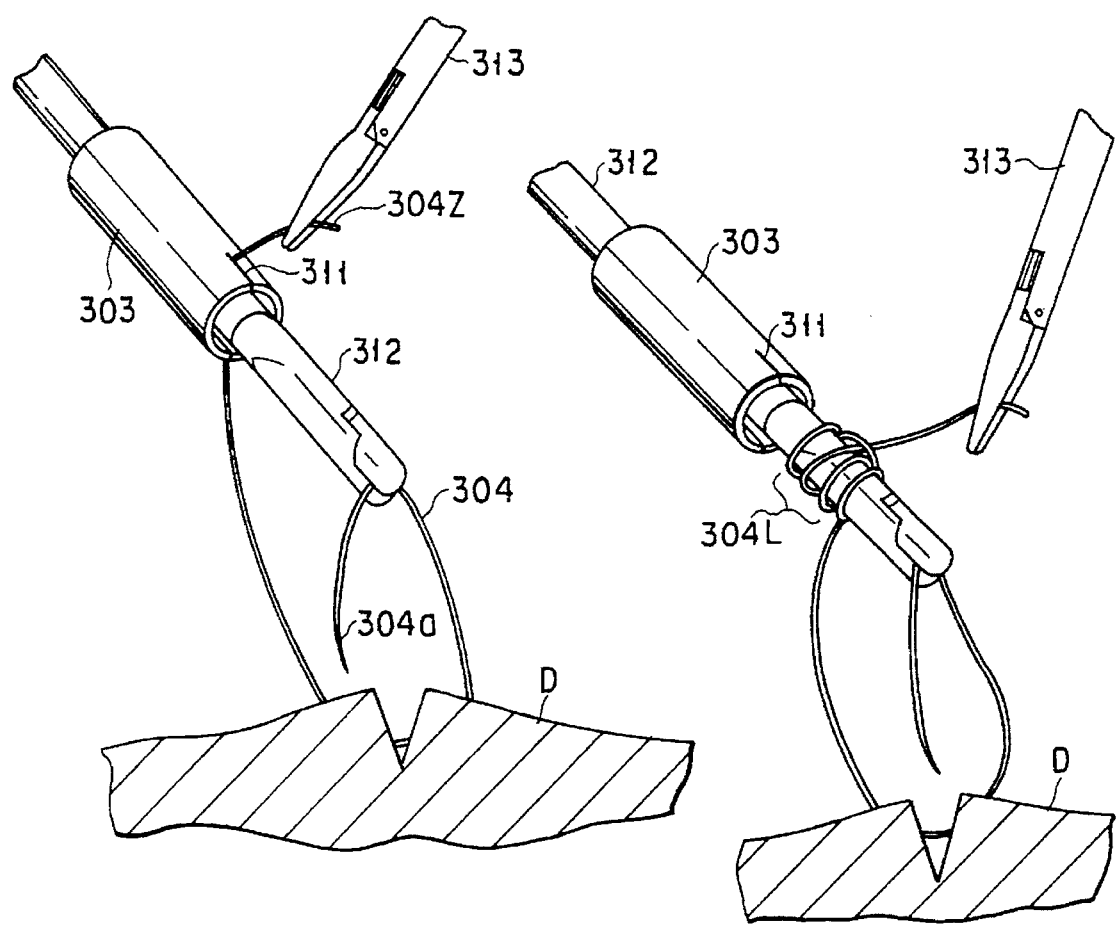
FIG. 71 is an explanatory view of a state wherein the suturing instrument is mounted on the forceps to perform suture.
FIG. 72 is an explanatory view of a state wherein a loop is extracted from the forceps to perform ligation.
Figure 73:
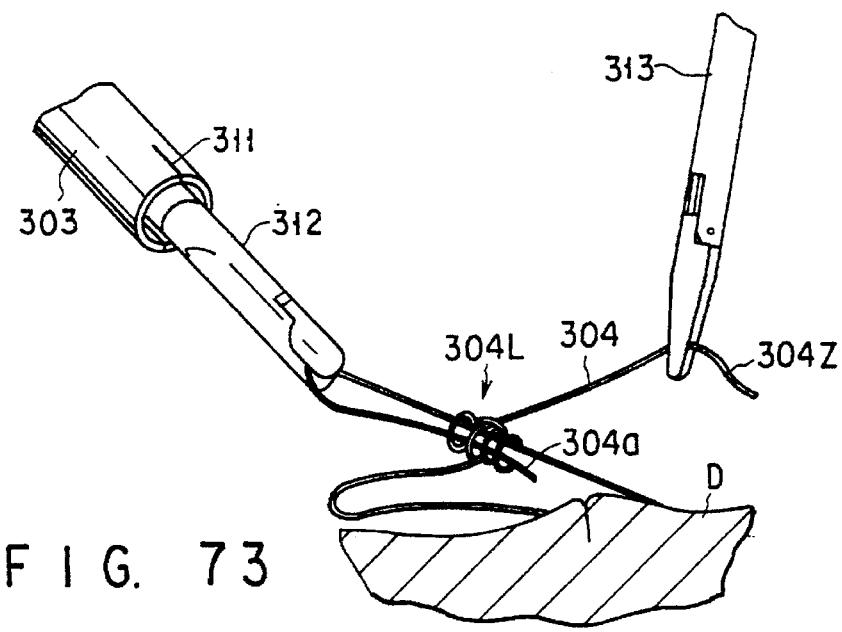
FIG. 73 is an explanatory view showing a state wherein a knot is formed by using the loop extracted from the forceps.

Thereafter, as shown in FIG. 71, the suture 304 on its needle 304a side, which appears from the tissue, is held by the forceps 312 on which the suture suturing instrument 301 is mounted. The other end 304z (a side which is not the needle side) of the needle 304a appearing from the outer cylinder 303 of the suture suturing instrument 301 is seized by the forceps 313 which is separately inserted into the body cavity. The loop 304L is removed from the outer cylinder 303 and pulled toward the distal end of the forceps 312. Thus, as shown in FIG. 72, the loop 304L which has been housed in the outer cylinder 303 is pulled, and is fed toward the distal end of the forceps 312. At this time, the forceps 312 grips the suture 304 on its needle 304a side at its distal end. Thus, when the knot is further fed, the suture 304 on its needle 304a side passes through the ring of the knot (the loop 304L), as shown in FIG. 73. Then, the forceps 312 (on which the suturing instrument is mounted) holding the end of the suture 304 on the needle 304a side and the forceps 313 gripping the other end 304z of the suture 304 are pulled to fasten the tissue D as tightly as required, thereby firmly fastening a knot N, as shown in FIG. 74. The knot N formed at this time forms a double looping of square-double knot formation, as shown in FIG. 75.

The transfixion suture operation is completed in this manner. The extra portion of the suture 304 is cut and recovered outside the body together with the needle 304a. The outer cylinder 303 mounted on the forceps 312 is also removed. When a second-stitch suturing operation is to be performed, another suturing instrument 301 is used to repeat the above procedure.

In the suturing instrument 301 having the above arrangement, since the suture is held toward the distal end of the forceps 312 by the incisions 311 formed at the distal end of the outer cylinder 303, the suture will not be shifted upon being inserted into a trocar or the like, and can be easily removed toward the distal end by another forceps 313.

Because of the presence of the inner cylinder 302, the loop 304L can be arranged on the outer circumferential portion of the forceps 312 as it is without deforming the shape. Because of the presence of the inner cylinder 302, when the suturing instrument 301 is to be assembled, it can be assembled very easily by winding the suture 304 on the inner cylinder 302 and inserting the inner cylinder 302 in the outer cylinder 303. Since the loop 304L is covered with the outer cylinder 303, the loop 304L will not move, be removed from the forceps 312, or be caught by something. As the loop 304L is stored in the outer cylinder 303, it can be kept easily. Since the knot N has double ligation of square-double knot formation as double looping, a firm knot can be obtained. Since the knot N is fastened by directly pulling the two ends of the suture 304 in opposite directions with the two forceps 312 and 313, the knot can be firmly fastened.

FIGS. 76 and 77 show a modification of the fifth embodiment. This modification is different from the fifth embodiment in the structure of the fixing means that fixes the outer cylinder 303 on the forceps 312. In this modification, a forceps fixing member 314 having a smaller diameter than that of the outer cylinder 303 is provided at the forceps fixing portion 309 on the rear end of the outer cylinder 303. The forceps fixing member 314 has an inner diameter equal to or slightly larger than the diameter of the forceps 312, and communicates with the inner hole of the suture housing portion 308 while maintaining its diameter. A portion covering from the forceps fixing member 314 to the rear portion of the outer cylinder 303 is divided into six portions about the axis. A fastening cylinder 315 is prepared, which has an inner diameter slightly smaller than the diameter of the forceps fixing member 314, so that it can be fitted on the forceps fixing member 314.

In this mechanism, when the suturing instrument 301 is to be mounted on the forceps 312, the forceps 312 is inserted in the fastening cylinder 315 first, and then the forceps 312 is inserted from the rear end of the outer cylinder 303, in the same manner as in the fifth embodiment. At this time, the outer cylinder 303 moves smoothly with respect to the forceps 312 to fit the fastening cylinder 315, which has been inserted in advance, on the forceps fixing member 314 at a desired position, thereby fixing the outer cylinder 303 on the forceps 312. FIG. 77 shows this state. With this arrangement, as the slidable movement of the forceps 312 becomes smooth, the suturing instrument 301 can be easily mounted on the forceps 312, and is reliably fixed by the fastening cylinder 315. Therefore, the outer cylinder 303 will not be undesirably shifted by some reason.

Figure 79:
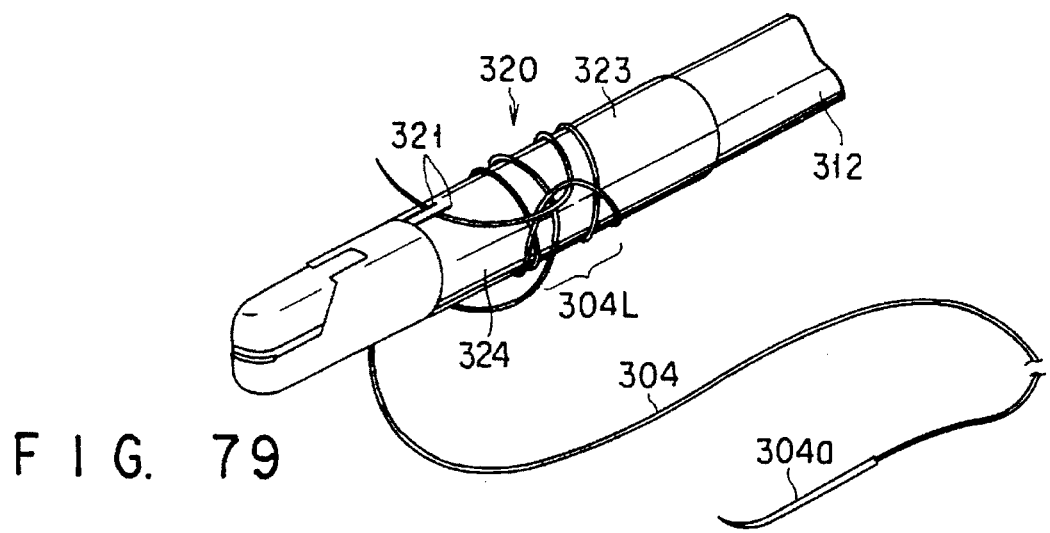
FIG. 79 is a perspective view of a state wherein the suturing instrument shown in FIG. 78 is mounted on a forceps.
Figure 80:
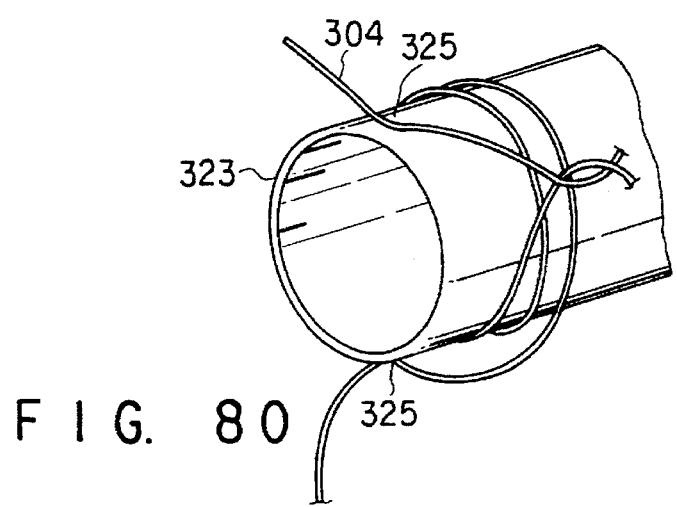
FIG. 80 is a perspective view showing part of a suturing instrument according to a modification of the sixth embodiment.

FIGS. 78 to 80 show a suturing instrument 320 according to the sixth embodiment.

As shown in FIG. 78, the suturing instrument 320 according to the sixth embodiment has a hollow cylindrical suture winding member 323 serving as a suture holding member. A suture 304 attached with a needle 304a at its distal end is held by a suture housing portion 324 provided on the outer circumferential portion of the suture winding member 323 to serve as a loop holding portion. The suture winding member 323 is a sufficiently thin cylinder, and its inner hole has a diameter almost equal to or slightly smaller than the outer diameter of a forceps used to correspond it. Two rows of suture holding grooves 321 are formed in the upper portion of the distal end of the cylindrical portion of the suture winding member 323 at an appropriate distance from each other, and two rows of other suture holding grooves 321 are similarly formed in the lower portion of the distal end of the cylindrical portion of the suture winding member 323. In this embodiment, these suture holding grooves 321 form a suture fixing portion.

A suture is wound on the suture winding member 323 in the same manner as in the fifth embodiment. The suture can be wound in accordance with any method as far as a knot N can be formed. The end portion of the wound suture 304 on its needle 304a side is passed through the two suture holding grooves 321 formed in the lower portion of the distal end of the suture winding member 323, and is held in them. The other end portion 304z of the suture 304 is passed through the suture holding grooves 321 in the upper portion of the distal end of the suture winding member 323, and is held in them. The suture winding member 323 is made of a resin having an appropriate elasticity.

When suture is to be performed by using the suturing instrument 320 having the above arrangement, first, a forceps 312 is passed through the inner hole of the suture winding member 323, as shown in FIG. 79. Since this inner hole has a diameter which is equal to or slightly smaller than the diameter of the forceps 312, and the suture winding member 323 has an appropriate elasticity, the suture winding member 323 is movably fixed on the outer circumferential surface of the forceps 312 with an appropriate force. The forceps 312 fixed in the suture winding member 323 is inserted into the boy cavity through, e.g., a trocar. At this time, since the two ends of the suture 304 wound on the suture winding member 323 are held by the suture holding grooves 321, the wound suture 304 maintains its shape even in the body cavity. Suture is performed by using another forceps 313 (FIG. 71) in the same manner as in the fifth embodiment.

In this arrangement, since the suture winding member 323 has a thin wall, it can be inserted from a trocar having a small-diameter. Since the loop L is mounted on the forceps 312 together with the cylinder (the suture winding member 323) inside the loop L, a loop 304L can be arranged on the outer circumferential surface of the forceps 312 without deforming the shape.

FIG. 80 shows a modification of the sixth embodiment. This modification is different from the sixth embodiment in how to hold the suture 304. In this modification, the suture 304 is adhered to the distal end of the suture winding member 323 with an adhesive 325 with an adhesion strength so that it can be separated if it is pulled strongly. This adhesive 325 forms a suture fixing portion.

With this arrangement, the suture can be removed only by pulling, which is simple.

In place of the adhesive, the suture 304 and the suture winding member 323, both made of a resin material, may be electrically charged, and the suture 304 may be held by the suture winding member 323 by static electricity.

Then, once the suture 304 is removed, it can be held by the suture winding member 323 again, and if ligation is stopped due to a failure or the like, the suture can be ligated again.

Figure 81:
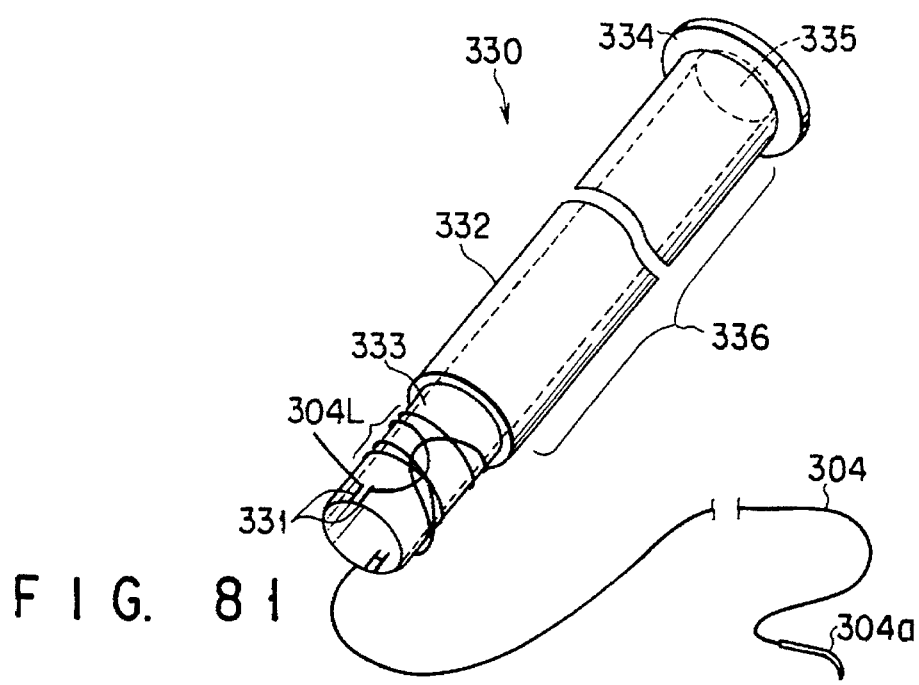
FIG. 81 is a perspective view of a suturing instrument according to the seventh embodiment.
Figure 82:
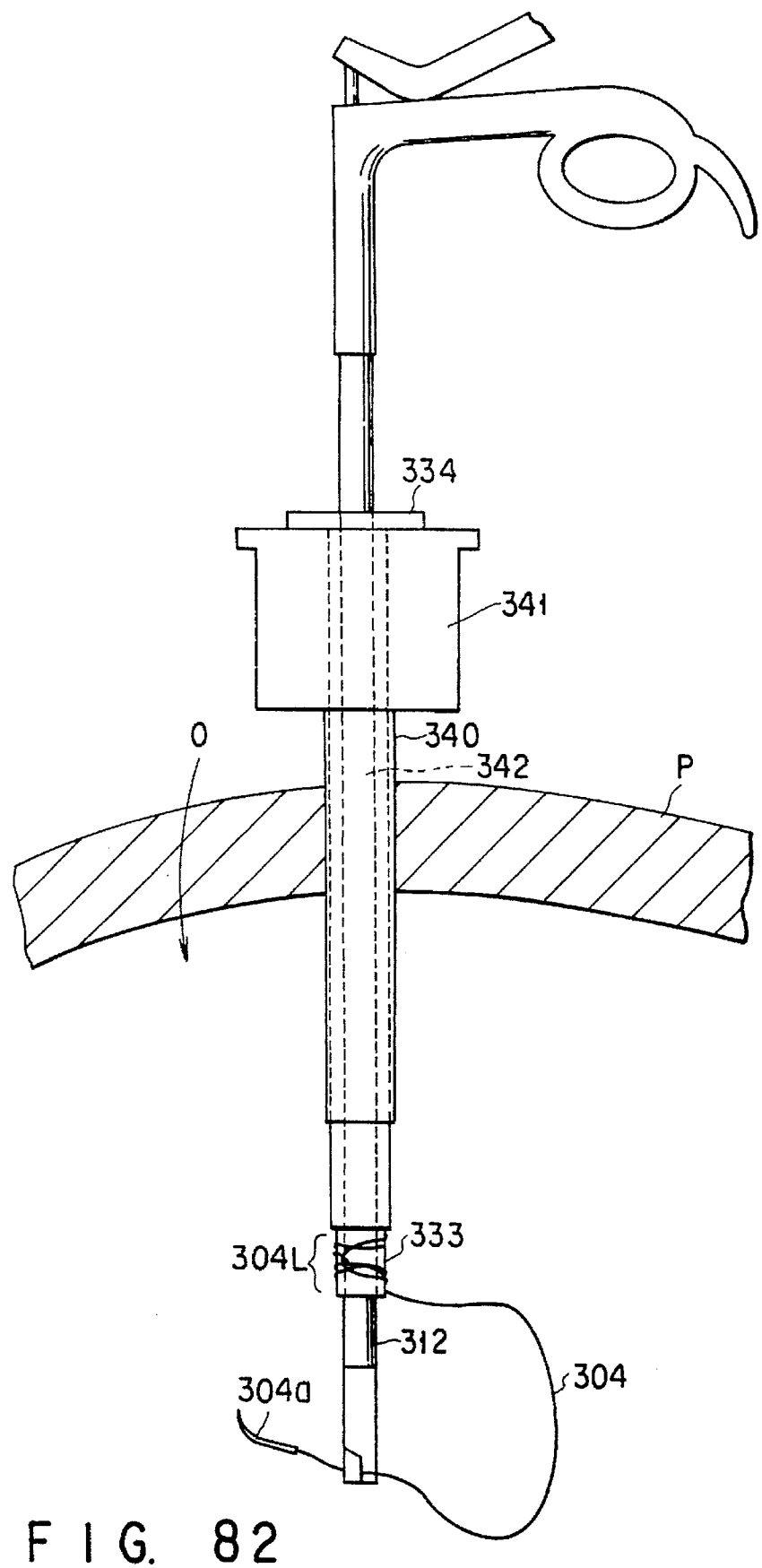
FIG. 82 is an explanatory view showing a state wherein suturing is performed by using the suturing instrument according to the seventh embodiment.

FIGS. 81 and 82 show a suture 330 according to the seventh embodiment. The suture 330 is used especially together with a trocar unit.

In this suture 330, a suture winding portion 333 is provided at the distal end of a trocar insertion pipe 332 which is to be inserted into a trocar cannula 340 (FIG. 82). Incisions 331 serving as suture fixing portions are formed in the distal end of the suture winding portion 333, and a suture 304 attached with a needle is fixed in the incisions 331. The trocar insertion pipe 332 serving as the suture holding member is made of a cylindrical elastic member, and an inner hole 335 having a predetermined diameter extends in the trocar insertion pipe 332. A forceps 312 is inserted in the inner hole 335. The inner hole 335 has a diameter almost equal to or slightly larger than the outer diameter of the forceps 312, so that the forceps 312 is slidable in the inner hole 335 and that air-tightness is maintained. Reference numeral 334 denotes a locking portion for locking the trocar insertion pipe 332 to a hand-side portion 341 of the trocar cannula 340.

A suture 304 is wound on the suture winding portion 333 at the distal end of the trocar insertion pipe 332. The suture winding portion 333 and a method of winding the suture 304 are the same as those in the sixth embodiment, and a detailed description thereof will be omitted.

A trocar insertion portion 336, arranged between the suture winding portion 333 and the locking portion 334 and in the trocar cannula 340 has a diameter larger than the that of the suture winding portion 333 to prevent a loop 304L from being shifted backward when the trocar insertion portion 336 is being inserted into the trocar cannula 340. The trocar insertion portion 336 has an outer diameter almost equal to or slightly smaller than the diameter of the inner hole of the trocar cannula 340 to be used. The trocar insertion portion 336 is longer than the trocar cannula 340 by a certain length. However, the entire length of the trocar insertion pipe 332 is smaller than that of the forceps 312 to be used. The trocar locking portion 334 has a diameter sufficiently larger than the inner diameter of the trocar cannula 340. Thus, this portion is locked by the hand-side portion 341 and does not enter the trocar cannula 340.

In the suture 330 having the above arrangement, first, the trocar insertion pipe 332 is inserted from its distal end into the trocar cannula 340 pierced into a body wall P. At this time, if a needle 304a and the linear portion of the suture 304 continuous to the needle 304a are set in the trocar insertion pipe 332, they can be easily inserted into the trocar cannula 340. The forceps 312 to be used is inserted into a body cavity 0 through the inner hole 335 of the trocar insertion pipe 332. At this time, the needle 304a and the suture 304 set in the inner hole 335 are pushed out by the forceps 312, and fed into the body cavity O. Another forceps is inserted and operated in the same manner as in the fifth and sixth embodiments, thereby performing'suture. FIG. 82 shows this state.

In the suture 330 having the above arrangement, since the suture 330 is not directly mounted on the distal end of the forceps 312, the distal end of the forceps 312 is light weight and thus can be easily operated. Since air-tightness is maintained between the trocar, the suturing instrument, and the forceps, an operation for obtaining pneumoperitoneum will not be interfered with.

Therefore, with the suturing instruments according to the fifth, sixth, and seventh embodiments, since the loop 304L forming a knot N can be formed outside the body in advance and can be guided into the body cavity, an operation of forming a loop by using a surgical instrument, which is difficult in ordinary internal ligation, is eliminated, thus facilitating an operation of forming a knot in the body cavity. Since ligation is performed in the body cavity by using two forceps, the fastening degree can be easily obtained and adjusted, and the knot can be firmly ligated. When the loop 304L is to be inserted into the body cavity, since the suture is fixed by the suture holding member, the loop 304L will not be removed from the forceps 312 even when it is to be inserted into the body cavity through a trocar or the like, thus realizing a quick operation.

Many forceps are not required for ligation. Once the forceps 312 is inserted in the body cavity, it need not be extracted or inserted again from or into the body cavity until the first-stitch suturing operation is completed. The distal end of the forceps 312 does not interfere with the suturing instrument, and the function of the forceps 312 is not impaired. Any type of forceps 312 can be used as far as its diameter satisfies requirements. Thus, the degree of operational freedom is high.

Furthermore, since a space through which the forceps 312 is inserted is held inside the loop 304L, the loop 304L can be easily arranged around the forceps 312. The loop 304L to form the knot N is wound on the forceps 312 in advance, and the knot N can be formed only with a simple operation of seizing, pulling, and pushing. Therefore, even if a sufficient space for suturing is not maintained in the body cavity, or even if the forceps 312 is difficult to operate, suture can be performed.

The eighth embodiment of the present invention will be described with reference to FIGS. 83 to 94.

FIG. 83 shows the schematic arrangement of a suture holding member 401 of a suturing instrument. The suture holding member 401 is provided with an inner cylinder 402 and an outer cylinder 403 in which the inner cylinder 402 is loosely inserted.

An inner cylinder gripping portion 404 is provided at the distal end portion of the inner cylinder 402. The inner cylinder gripping portion 404 has an outer diameter almost equal to that of the outer cylinder 403, and is not housed in the outer cylinder 403. Furthermore, a suture winding portion 405 is provided on the rear end portion side of the inner cylinder 402, as shown in FIG. 85B. The suture winding portion 405 is inserted in the outer cylinder 403 and has a tapered surface. A fixing portion 406 is provided between the inner cylinder gripping portion 404 and the suture winding portion 405. The fixing portion 406 is fitted on the inner circumferential wall surface of the outer cylinder 403, thereby fixing the inner cylinder 402. A plurality (four in this embodiment) of sutures 407A, 407B, 407C, and 407D are wound on the suture winding portion 405 of the inner cylinder 402 in a manner shown in FIG. 86 and described in relation to the first embodiment to respectively form loop portions 407L each serving as triple ligation for forming a knot. The sutures 407A to 407D can be of any type as far as they are used for a surgical operation.

As shown in FIG. 90, a closed portion 402b is provided in an internal cavity 402a (FIG. 85B) of the inner cylinder 402 on its inner cylinder gripping portion 404 side. The internal cavity 402a terminates at the closed portion 402b of the inner cylinder 402 on its distal end portion side. The internal cavity 402a of the inner cylinder 402 is formed such that the inner diameter of the suture winding portion 405 is larger than the diameter of an inserting portion 421a of a forceps to be used in combination with this forceps 421, e.g., a forceps 421 shown in FIG. 89.

In this forceps 421, an operating portion 421b is coupled to the end portion of the inserting portion 421a on its operator's hand side, and a gripping portion 421c which is opened/closed by the operating portion 421b is provided at the distal end portion of the inserting portion 421a.

As shown in FIG. 84, a small-diameter forceps fixing portion 408 is formed in one end portion side of the outer cylinder 403, and a suture housing portion 409 having a larger diameter than that of the forceps fixing portion 408 is formed at a portion of the outer cylinder 403 excluding the forceps fixing portion 408.

The suture housing portion 409 is set to have a length almost equal to the sum of the lengths of the fixing portion 406 and the suture winding portion 405 of the inner cylinder 402. The suture housing portion 409 has an inner diameter enough to be lightly fitted on the fixing portion 406 of the inner cylinder 402.

The forceps fixing portion 408 has an inner diameter enough to be lightly close-fitted on the inserting portion 421a of the forceps 421 which is used in combination with this suture holding member 401. Six radial incision grooves 410 are formed to extend from the inner hole of the forceps fixing portion 408 toward the outer circumference of the outer cylinder 403 at an equal angular interval in the circumferential direction of the forceps fixing portion 408. When a forceps is inserted, portions among the incision grooves 410 are deformed comparatively easily, to reliably fix the inserting portion 421a of the forceps 421.

A total of eight suture locking grooves 411A to 411D, and 411A40 to 411D' are formed in the distal end portion of the outer cylinder 403 to respectively lock with the two end portions of the four sutures 407A, 407B, 407C, and 407D wound on the suture winding portion 405 of the inner cylinder 402. The eight suture locking grooves 411A to 411D, and 411A' to 411D' are arranged in the distal end portion of the outer cylinder 403 at an equal angular interval in the circumferential direction.

Figure 85A:
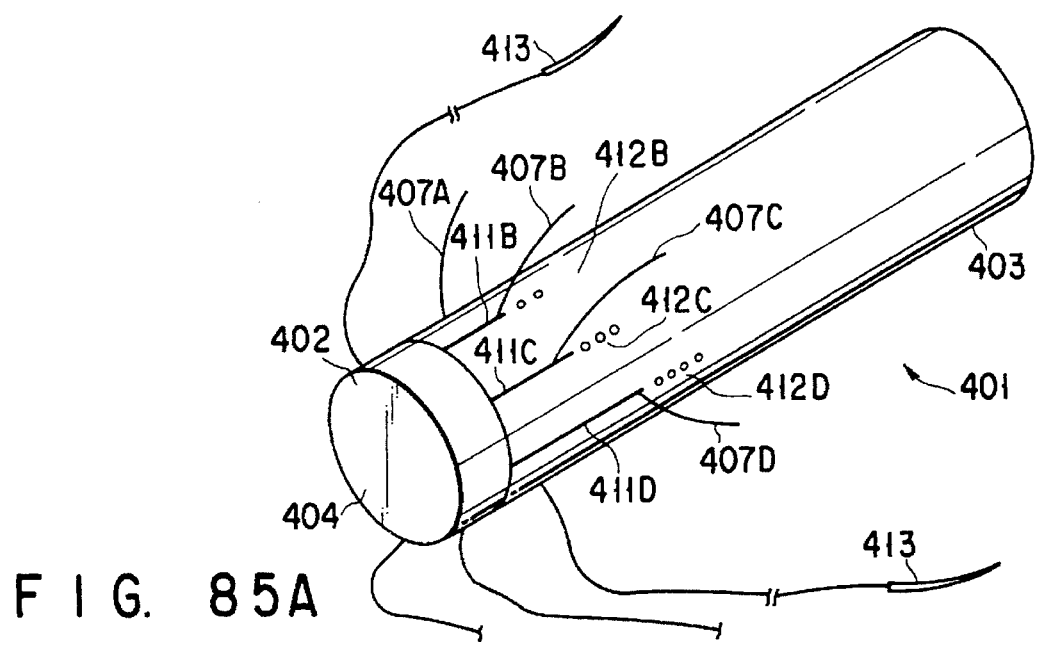
FIG. 85A is a perspective view showing an assembled state of the suture holding member.
Figure 85B:
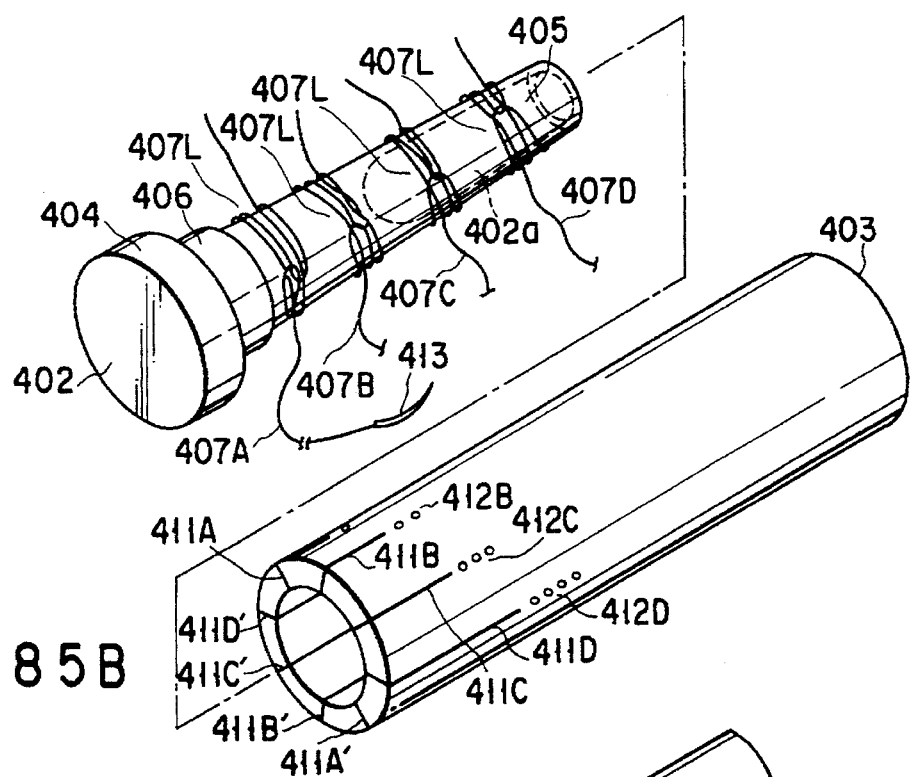
FIG. 85B is a perspective view showing a state wherein the inner cylinder of the suture holding member is removed from the outer cylinder.
Figure 85C:
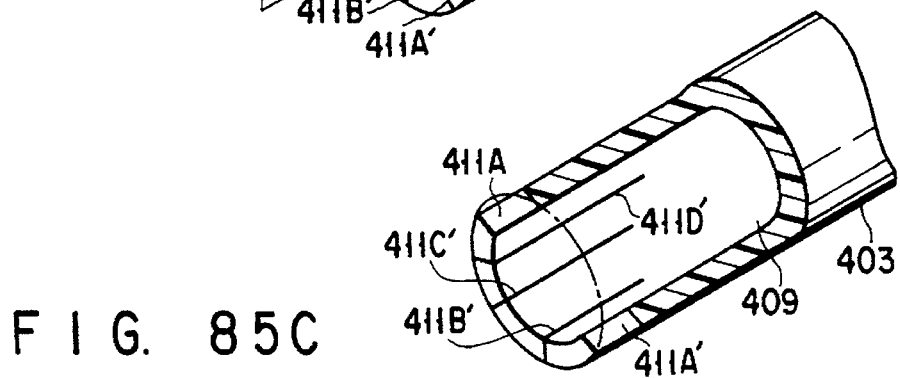
FIG. 85C is a partially cutaway perspective view of the suture locking grooves of the outer cylinder.

In this case, as shown in FIG. 85, the suture locking grooves 411A and 411A', 411B and 411B', 411C and 411C', and 411D and 411D' arranged at positions opposite to each other in the radial direction at the distal end portion of the outer cylinder 403 have the same length. The suture locking grooves 411A and 411A' are the shortest in the axial direction of the outer cylinder 403. The lengths are increased in the order of 411B or 411B', 411C or 411C', and 411D or 411D'.

Displays, e.g., dot displays 412A to 412D, are formed on the rear portions of the suture locking grooves 411A to 411D, and 411A' to 411D', to indicate the positions of the corresponding grooves. The dot displays 412A to 412D are respectively provided with one, two, three, and four dots in accordance with the lengths of the corresponding suture locking grooves 411A to 411D, and 411A' to 411D', such that a shorter suture locking groove has fewer dots. For example, the dot display 412A provided with one dot is formed on the rear portion of each of the suture locking grooves 411A and 411A'.

A suturing needle 413 is coupled to one end portion of each of the four sutures 407A to 407D wound on the suture winding portion 405 of the inner cylinder 402. An A end portion 407a as the suturing needle 413 side end portion and a B end portion 407b as the other end portion, respectively, of the suture 407D wound on the endmost position of the suture winding portion 405 of the inner cylinder 402 are respectively locked by the longest suture locking grooves 411D and 411D' (each provided with the dot display 412D having four dots) of the outer cylinder 403. Similarly, the two ends of the suture 407C which is wound on the second position, when counted from the rear end position, of the suture winding portion 405 of the inner cylinder 402 are respectively locked by the suture locking grooves 411C and 411C' of the outer cylinder 403. The two ends of the suture 407B which is wound on the third position, when counted from the rear end position, of the suture winding portion 405 of the inner cylinder 402 are respectively locked by the suture locking grooves 411B and 411B' of the outer cylinder 403. The two ends of the suture 407A which is wound on the fourth position, when counted from the rear end position, of the suture winding portion 405 of the inner cylinder 402 are respectively locked by the suture locking grooves 411A and 411A' of the outer cylinder 403.

In this embodiment, the sutures 407A, 407B, 407C, and 407D are attached with needles. However, they may not be attached with needles 413. The sutures 407A, 407B, 407C, and 407D are not limited to absorbing/non-absorbing sutures or natural/synthetic sutures, but may be of any type.

Figure 87A:
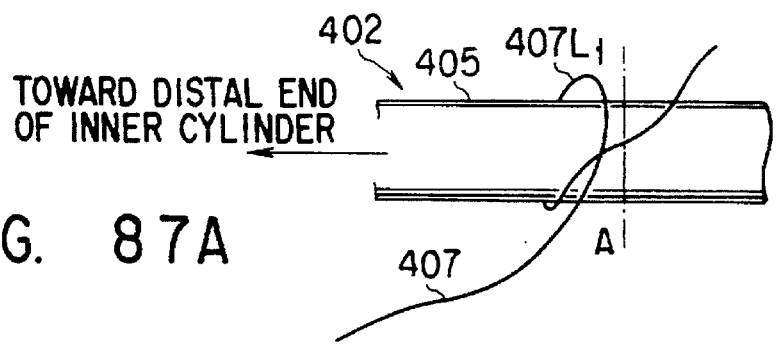
FIG. 87A is a side view showing a first loop formed by winding the switching suture by one turn toward the distal end of the inner cylinder.

A method of winding the suture 407A (407B, 407C, or 407D) on the suture winding portion 405 of the inner cylinder 402 will be described. First, as shown in FIG. 87A, the suture 407A (407B, 407C, or 407D) is wound on the suture winding portion 405 toward the distal end of the inner cylinder 402 by one turn, thereby forming a first loop $407L_1$ (loop 1).

Figure 87B:
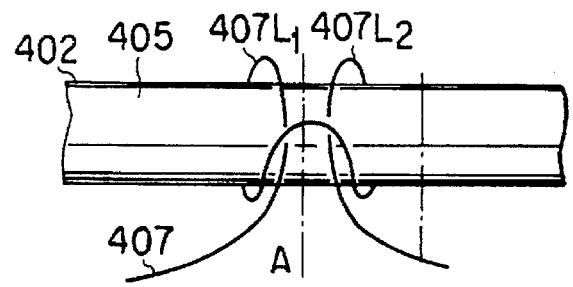
FIG. 87B is a side view showing a state wherein the suture is wound on the inner cylinder to form a second loop such that the first and second loops are symmetrical about a broken line A.

Subsequently, as shown in FIG. 87B, the suture 407A (407B, 407C, or 407D) is wound on the suture winding portion 405 to form a second loop $407L_2$ (loop 2) such that the first and second loops are symmetrical about a broken line A.

Figure 87C:
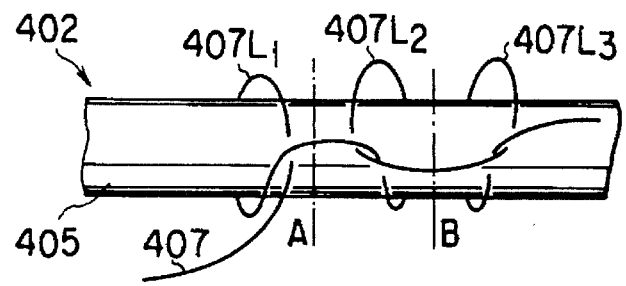
FIG. 87C is a side view showing a state wherein the suture is wound on the inner cylinder to form a third loop such that the second and third loops are symmetrical about a broken line B.

As shown in FIG. 87C, the suture 407A (407B, 407C, or 407D) is wound on the suture winding portion 405 to form a third loop $407L_3$ (loop 3) such that the second and third loops are symmetrical about a broken line B.

Figure 86:
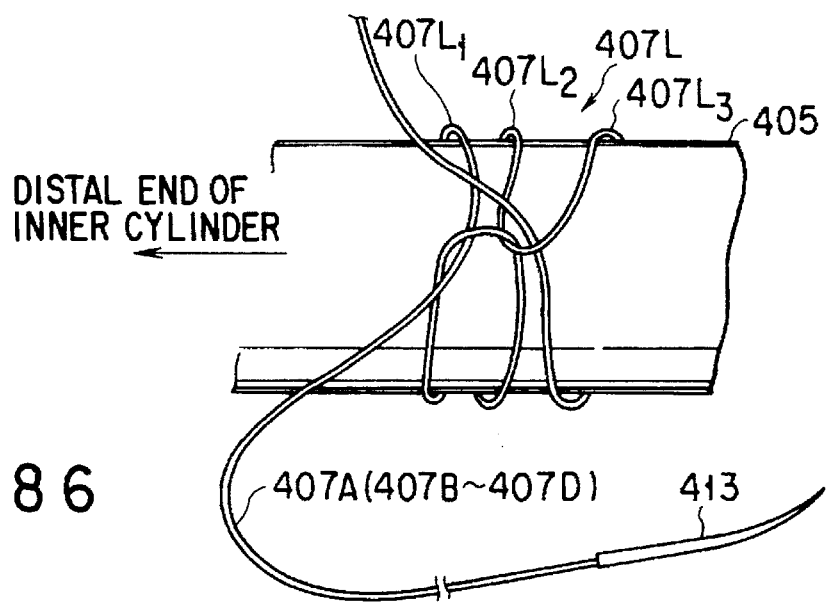
FIG. 86 is an explanatory view for explaining how to wind the suture on the suture winding portion of the inner cylinder.

Thus, the loop portion 407L serving as triple ligation to form a knot shown in FIG. 86 is formed. Thereafter, when one end (A end) 407A of the suture 407A (407B, 407C, or 407D) is passed through the three loops $407L_1$ to $407L_3$, as indicated by an arrow in FIG. 88A, and pulled, the relationship between the suture 407A (407B, 407C, or 407D) on its A end 407a side and the respective loops $407L_1$ to $407L_3$ of the loop portion 407L becomes identical to that of the triple knot formation shown in FIG. 88B. More specifically, the loops $407L_1$, $407L_2$, and $407L_3$ respectively correspond to a single ligation portion o, a double ligation portion p, and a triple ligation portion g, respectively, of the triple ligation shown in FIG. 5B, and the different winding direction of the loop 2 corresponds to the difference in the direction in the square or double knot formation. The manner to wind the sutures 407A to 407D is not particularly limited to that of this embodiment, but can be of any time as far as it can form ligation.

Regarding the inner cylinder 402 and the outer cylinder 403 of the suture holding member 401, and the sutures 407A, 407B, 407C, and 407D, the four sutures 407A, 407B, 407C, and 407D are wound on the suture winding portion 405 of the inner cylinder 402 in advance, as shown in FIG. 85B, to respectively form the triple ligation loop portions 407L, and a portion of the suture winding portion 405, on which the loop portions 407L of the sutures 407A, 407B, 407C, and 407D are wound, is inserted in the suture housing portion 409 of the outer cylinder 403. At this time, the sutures 407D, 407C, 407B, and 407A, mentioned from the one at the endmost position of the inner cylinder 402, are sequentially sandwiched and locked by the corresponding suture locking grooves 411D and 411D' to 411A and 411A' of the outer cylinder 403 in the order named. Finally, the fixing portion 406 of the inner cylinder 402 is fitted and fixed in the outer cylinder 403.

Figure 91:
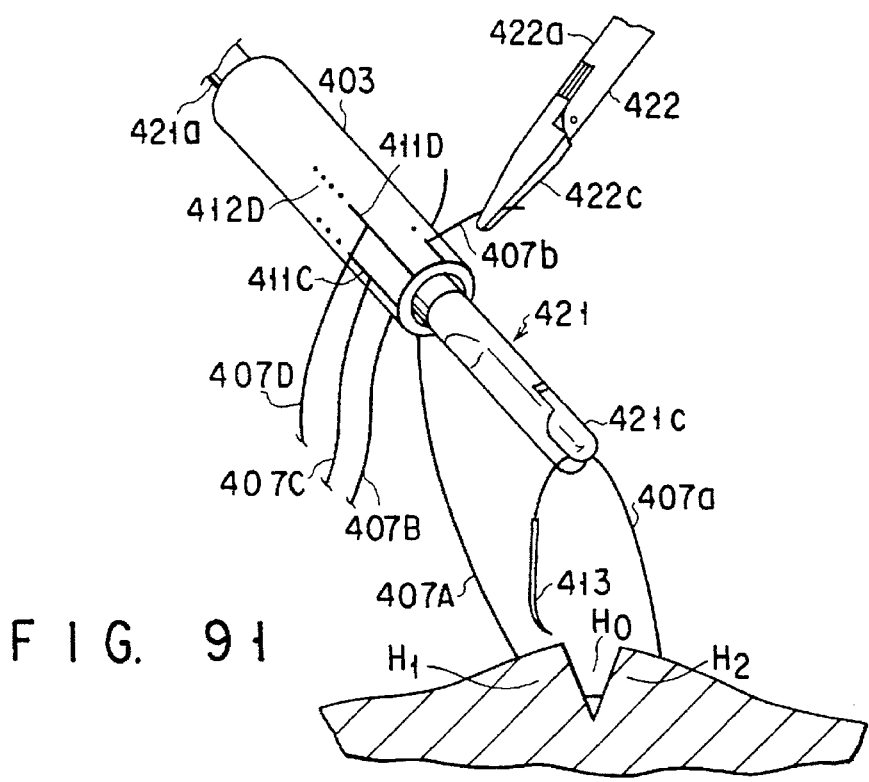
FIG. 91 is a perspective view showing a state wherein the suture is passed between tissues on the two sides of the wounded portion of living body tissues by the first forceps and the B end portion of the suture is gripped by the second forceps.

The operation of the above arrangement will be described. A case will be described wherein the suture holding member 401 of this embodiment is used in combination with, e.g., the forceps 421 shown in FIG. 89 (to be referred to as the first forceps hereinafter), and tissues $H_1$ and $H_2$ on the two sides of a wounded portion $H_0$ of the living body tissues in the patient as shown in FIG. 91 are to be ligated.

First, as shown in FIG. 90, the inserting portion 421a of the first forceps 421 is inserted in the internal cavity of the forceps fixing portion 408 at the rear end portion of the outer cylinder 403 of the suture holding member 401 in which the inner cylinder 402, the outer cylinder 403, and the sutures 407A, 407B, 407C, and 407D are mounted. When the first forceps 421 is deeply inserted, the distal end portion of the inserting portion 421a of the first forceps 421 is inserted in the internal cavity 402a of the suture winding portion 405 of the inner cylinder 402.

In this state, when the first forceps 421 is pushed in further deeply, the distal end portion of the first forceps 421 is abutted against the closed portion 402b of the internal cavity 402a of the inner cylinder 402, and the closed portion 402b is pushed by the first forceps 421 in the inserting direction of the first forceps 421, so that the inner cylinder 402 is pushed out from the outer cylinder 403. At this time, as the inner cylinder 402 is pushed out from the outer cylinder 403, the loop portions 407L of the sutures 407A, 407B, 407C, and 407D wound on the suture winding portion 405 of the inner cylinder 402 are removed from the suture winding portion 405 of the outer cylinder 403 while maintaining their original shapes, and are wound on the first forceps 421 which is inserted to replace the inner cylinder 402. The inner cylinder 402 removed from the suture winding portion 405 is removed from the first forceps 421.

The outer cylinder 403 is fixed on the first forceps 421 with its forceps fixing portion 408 in a light close-fitted state. At this time, because of the elasticity of the material of the outer cylinder 403 and the incision grooves 410, the outer cylinder 403 can be moved on the first forceps 421 in its axial direction with an appropriate force, and is held as it is arranged at an appropriate position on the first forceps 421, as shown in FIG. 91.

When the first forceps 421 and the outer cylinder 403 of the suture holding member 401 are assembled in this manner, the first forceps 421, on which the outer cylinder 403 of the suture holding member 401 is mounted, is inserted into the body cavity through, e.g., a trocar, to ligate the living body tissues.

When, e.g., the tissues $H_1$ and $H_2$ on the two sides of the wounded portion $H_0$ are to be sutured, the A end portion 407a of the needle-attached suture 407A, which is locked by one suture locking groove 411A (which is the shortest) beside the dot display 412A provided with one dot, is held by the first forceps 421.

Subsequently, as shown in FIG. 91, the needle 413 is pierced to extend through the tissues $H_1$ and $H_2$ on the two sides of the wounded portion $H_0$. The suture 407A is passed through the tissues $H_1$ and $H_2$, and the A end portion 407a of the suture 407A is seized again by the first forceps 421.

Figure 92:
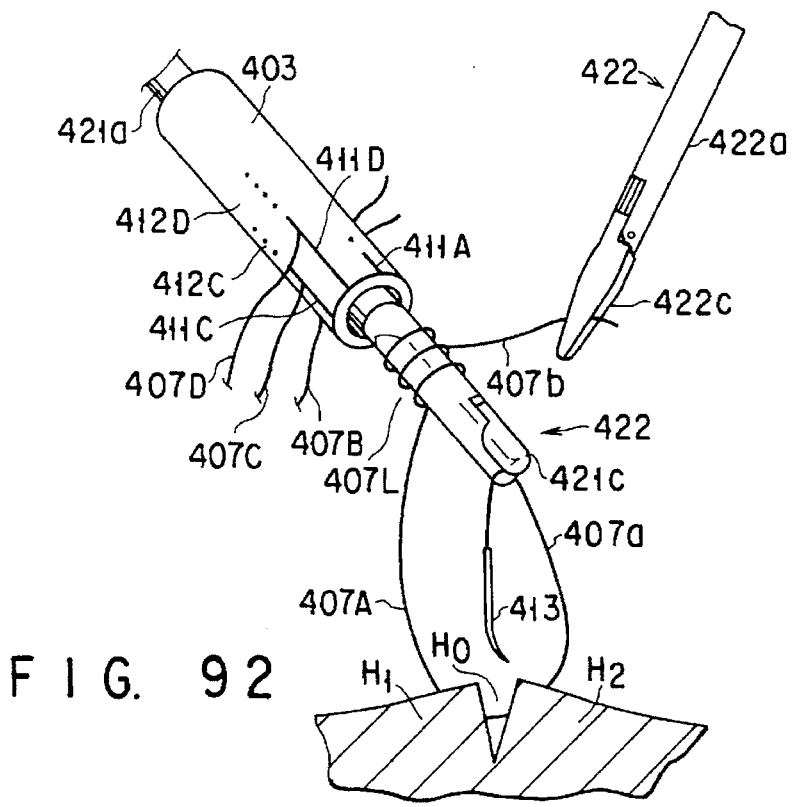
FIG. 92 is a perspective view showing a state wherein the loop portion of the suture is pulled out by the second forceps.

In this state, the B end portion 407b of the suture 407A, which is fixed in the other suture locking groove 411A' of the dot display 412A provided with one dot, is seized by another forceps (to be referred to as the second forceps hereinafter) 422. The second forceps 422 is moved upward to pull the B end portion 407b of the suture 407A, thereby removing the loop portion 407L of the suture 407A from the outer cylinder 403, as shown in FIG. 92. Then, the suture 407A is pulled toward the distal end of the first forceps 421.

Figure 93:
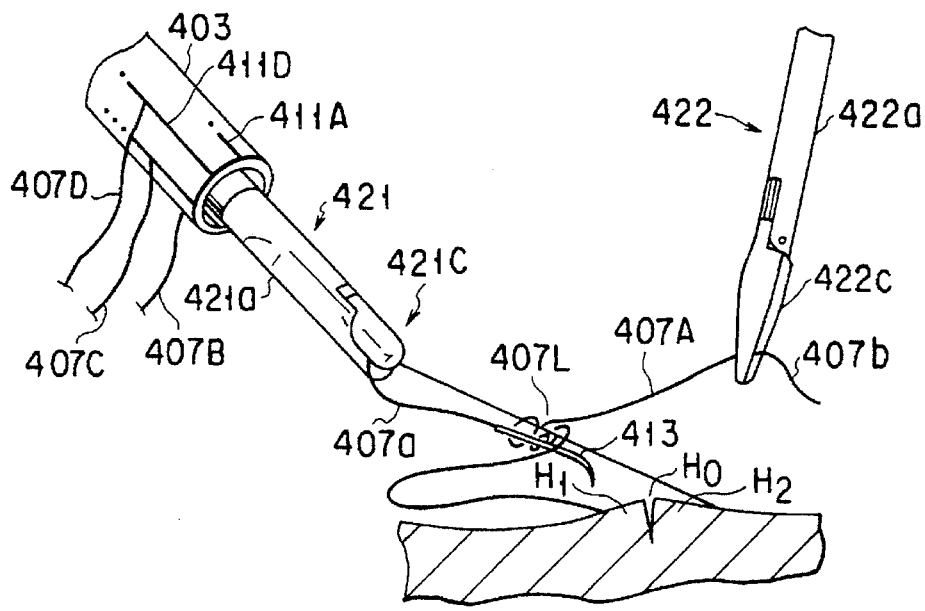
FIG. 93 is a perspective view showing a state wherein the A end portion of the suture is pulled by the first forceps and passed through the loop portion.
Figure 94:
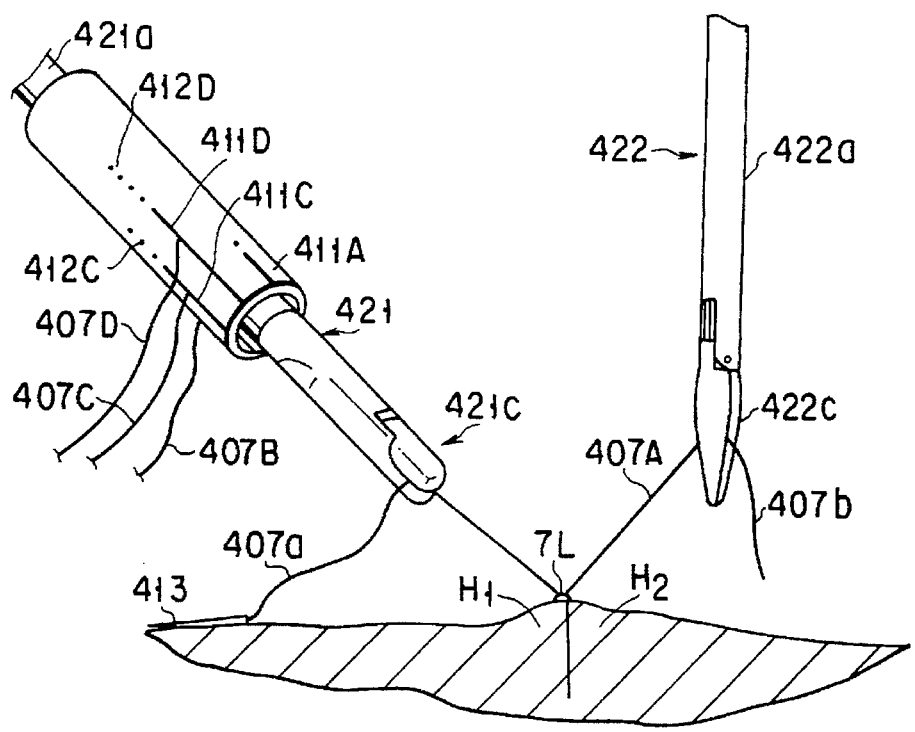
FIG. 94 is a perspective view showing a state wherein the suture is pulled by the first and second forceps to fasten the knot formed by the loop portion.
Figure 99A:
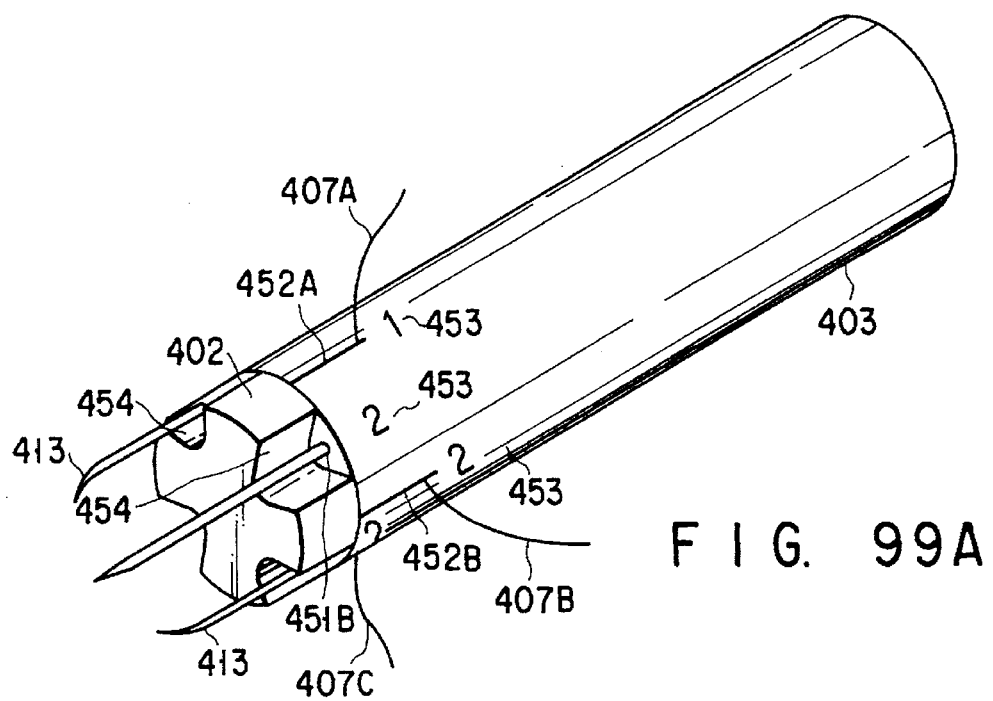
Figure 99B:
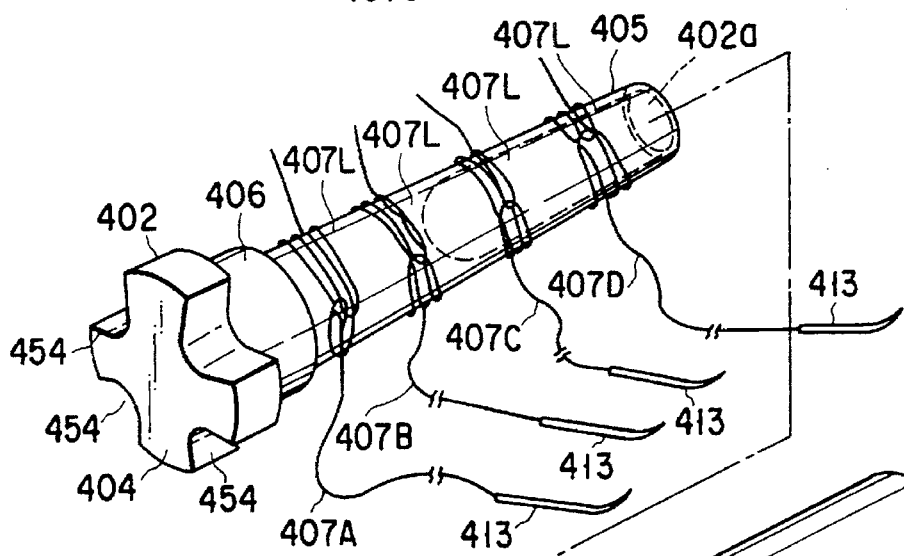
Figure 99B:
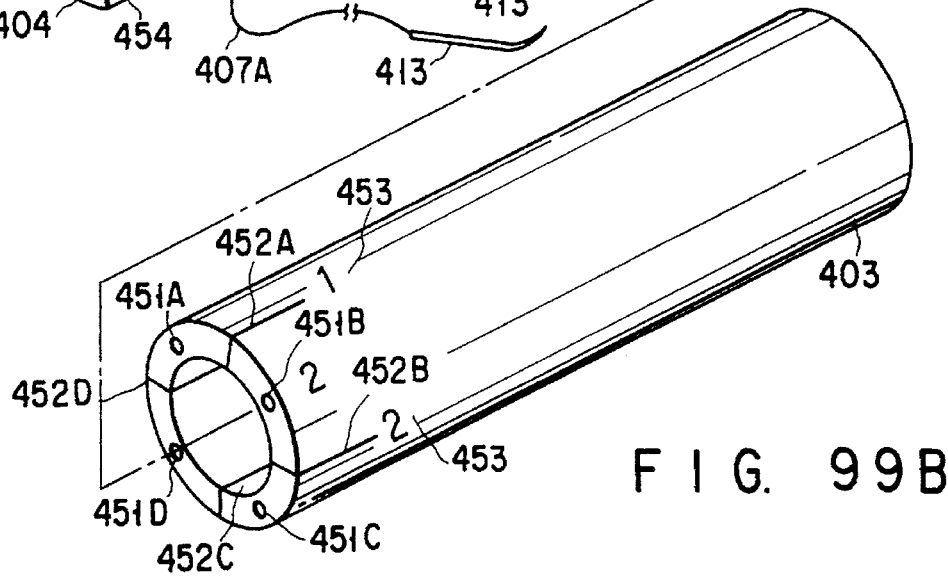

When the suture 407A is further pulled, its loop portion 407L is removed from the first forceps 421, and the A end portion 407a of the suture 407A passes through the loop portion 407L, as shown in FIG. 93. In this state, the first and second forceps 421 and 422 are pulled strongly to firmly fasten the knot of the loop portion 407L, as shown in FIG. 94, thereby suturing the tissues $H_1$ and $H_2$ on the two sides of the wounded portion $H_0$.

When suture is to be performed for another one suture, a suturing operation similar to that described above is performed by using the needle-attached suture 407 locked in the suture locking grooves 411B and 411B' (which are the second shortest) beside the dot displays B each provided with two dots. After this, a similar suturing operation is performed by using the needle-attached sutures 407C and 407D, which are respectively held by longer grooves beside dot displays provided with larger numbers of dots. In this embodiment, the suturing operation can be performed up to four-stitch suturing.

The above arrangement has the following effect. More specifically, when the four sutures 407A, 407B, 407C, and 407D are to be wound on the suture winding portion 405 of the inner cylinder 402 of the suture holding member 401 to respectively form triple ligation loop portions 407L for forming knots, and the suture holding member 401 is to be used in combination with the first forceps 421, as the inner cylinder 402 is pushed out from the outer cylinder 403, the loop portions 407L of the sutures 407A to 407D wound on the suture winding portion 405 of the inner cylinder 402 are wound on the first forceps 421, which is inserted to replace the inner cylinder 402, while maintaining their original shapes. Thus, a transfixion suture operation using a plurality of needles can be easily and reliably performed without extracting the first forceps 421 which has been inserted into the body cavity.

For this reason, an operation of suturing living body tissues ranging a comparatively large area in the body cavity, e.g., as in ligating the tissues $H_1$ and $H_2$ on the two sides of the wounded portion $H_0$ of the living body tissues in the patient's body, can be performed efficiently.

Of the eight suture locking grooves 411A to 411D, and 411A' to 411D' in the distal end portion of the outer cylinder 403, the suture locking grooves 411A and 411A' are formed to be the shortest in the axial direction of the outer cylinder 403, and the lengths are increased in the order of 411B or 411B', 411C or 411C', and 411D or 411D'. Simultaneously, the dot displays 412A to 412D are formed at the rear portions of the suture locking grooves 411A to 411D, and 411A' to 411D' to indicate the positions of the corresponding grooves. Therefore, the order with which the four sutures 407A to 407D wound on the suture winding portion 405 of the inner cylinder 402 is clearly indicated, thereby improving the operation efficiency.

Since the two end portions of the four sutures 407A to 407D are respectively locked by the eight suture locking grooves 411A to 411D, and 411A' to 411D' in the distal end portion of the outer cylinder 403, when the first forceps 421, on which the outer cylinder 403 of the suture holding member 401 is mounted, is to be inserted into the body cavity through, e.g., a trocar, the mounting positions of the four sutures 407A to 407D will not be shifted, or the loop portions 407L will not be removed from the first forceps 421.

The four sutures 407A to 407D locked by the eight suture locking grooves 411A to 411D and 411A' to 411D' in the distal end portion of the outer cylinder 403 can be easily removed from the outer cylinder 403 only by pulling them toward the distal end along the corresponding suture locking grooves 411A to 411D, and 411A' to 411D'.

When the outer cylinder 403 of the suture holding member 401 is mounted on the first forceps 421, the loop portions 407L of the respective sutures 407A to 407D are covered with the outer cylinder 403. Therefore, the loop portions 407L of the respective sutures 407A to 407D will not move on the first forceps 421, not be removed, or be caught by a surrounding obstacle and the like during insertion of the first forceps into the body cavity.

Since the suture holding member 401 is provided with the inner cylinder 402 having the suture winding portion 405, when the first forceps 421 is to be mounted in the outer cylinder 403 of the suture holding member 401/the loop portions 407L can be arranged on the outer circumferential surface of the first forceps 421 as they are without deforming the shape. To assemble the suture holding member 401 of this suturing instrument, only the loop portions 407L of the four sutures 407A, 407B, 407C, and 407D need be wound on the inner cylinder 402 and the inner cylinder 402 need be inserted into the outer cylinder 403. Therefore, the operation of assembling the suture holding member 401 can be facilitated.

When the tissues $H_1$ and $H_2$ on the two sides of the wounded portion $H_0$ are to be sutured, each suture 407A (407B, 407C, or 407D) can be strongly pulled with the first and second forceps 421 and 422, thereby firmly fastening the knot of the loop portion 7L of the suture 407A (407B, 407C, or 407D). As a result, a tight, firm knot can be formed, thereby performing a reliable ligation operation.

The colors of the four sutures 407A, 407B, 407C, and 407D to be wound on the suturing winding portion 405 of the inner cylinder 402 of the suture holding member 401 of the above embodiment may be changed. When the four sutures 407A, 407B, 407C, and 407D having different colors are wound on the suture winding portion 405 of the inner cylinder 402, the sutures 407A, 407B, 407C, and 407D to be used can be quickly discriminated. Therefore, in the suturing operation of the living body tissues, even if a plurality of sutures overlap after suturing has been performed for several sutures, the target suture 407A, 407B, 407C, or 407D can be easily discriminated.

FIG. 95 shows the first modification of the eighth embodiment. In this modification, display plates 431A, 431B, 431C, and 431D, each having a figure corresponding to the number of the suture counted from the distal end side of the outer cylinder 403, are provided to the B end portions 407b of the sutures 407A, 407B, 407C, and 407D on their sides opposite to the suturing needle 413.

In this case, the position of the target suture 407A (407B, 407C, or 407D) to be used is readily obtained by visually observing the display plates 431A, 431B, 431C, and 431D at the B end portions 407b of the respective sutures 407A, 407B, 407C, and 407D on their sides opposite to the suturing needle 413.

When the B end portion 407b of the target suture 407A (407B, 407C, or 407D) is to be seized, it can be seized at its display plate 431A, 431B, 431C, or 431D having a larger surface area than that of the suture 407A, 407B, 407C, or 407D. Therefore, the target suture 407A (407B, 407C, or 407D) can be seized more easily than in a case wherein the suture 407A (407B, 407C, or 407D) is seized directly.

FIG. 96 shows the second modification of the eighth embodiment. In this modification, each of the suture locking grooves 411A to 411D, and 411A' to 411D' of the outer cylinder 403 has a shape of a figure corresponding to the number of the suture counted from the distal end side of the outer cylinder 403. Also in this case, the position of the target suture 407A (407B, 407C, or 407D) to be used is readily obtained by visually observing the shapes of the respective suture locking grooves 411A to 411D, and 411A' to 411D' of the outer cylinder 403.

FIG. 97 shows the third modification of the eighth embodiment. In this modification, a loop portion 407M is formed by altering the manner to wind the suture 407A (407B, 407C, or 407D). More specifically, the A end portion 407a of the suture 407A (407B, 407C, or 407D) is wound on the suture winding portion 405 of the inner cylinder 402 from the left a plurality of times, e.g., five times, as indicated by an arrow in FIG. 97, to form five loops $407M_1$ to $407M_5$. Then, the A end portion 407a is passed through the loops $407M_3$, $407M_2$, and $407M_1$ from the right in FIG. 97 and fastened to form a knot which is a so-called loader knot.

FIG. 98A shows the fourth modification of the eighth embodiment. In this modification, a loop portion 407N is formed by further altering the manner to wind the suture 407A (407B, 407C, or 407D). More specifically, the suture 407A (407B, 407C, or 407D) is wound on the suture winding portion 405 of the inner cylinder 402 from the right in FIG. 98A twice to form the loop 1 consisting of two loops $407N_1$ and $407N_2$. Then, the terminal end portion of the left loop $407N_2$ is set to intersect the starting end portion of the right loop $407N_1$ and bent in the opposite direction, and the suture is wound on the suture winding portion 405 by one turn, thereby forming a loop $407N_3$ (loop 2).

When the A end portion 407a of the suture 407A (407B, 407C, or 407D) is passed through the loops 1 and 2 from the left as indicated by an arrow in FIG. 98A and fastened, the positional relationship between the suture 407A (407B, 407C, or 407D) on its A end 407a side and the suture 407A (407B, 407C, or 407D) on its loop portion 7N side becomes identical to that of a so-called surgeon knot shown in FIG. 98B.

FIGS. 99 to 102 show the ninth embodiment of the present invention. In this embodiment, the arrangement of the suture holding member 401 according to the eighth embodiment is partly altered as follows. More specifically, needle holding holes 451A to 451D for holding needles 413 of respective sutures 407A to 407D are formed in the distal end face of an outer cylinder 403. The respective needle holding holes 451A to 451D are arranged at positions to equally divide the distal end face of the outer cylinder 403 into four portions in the circumferential direction.

Suture locking grooves 452A, 452B, 452C, and 452D are formed in the distal end face of the outer cylinder 403 at the intermediate positions of pairs of the adjacent needle holding holes 451A and 451B, 451B and 451C, 451C and 451D, and 451D and 451A, respectively.

The needle holding holes 451A to 451D have hole diameters slightly larger than the diameter of the needles 413. When the needles 413 are inserted into the needle holding holes 451A to 451D from rear ends, A end portions 407a of the respective sutures 407A to 407D coupled to the mostends of the suturing needles 413 are inserted into the corresponding needle holding holes 451A to 451D together with the rear end portions of the needles 413. Thus, when the needles 413 and the A end portions 407a of the sutures 407A to 407D are inserted into the corresponding needle holding holes 451A to 451D from the rear ends, they are fitted in the corresponding needle holding holes 451A to 451D with an appropriate strength.

Displays 453 are provided, on the outer circumferential surface of the outer cylinder 403, at positions near the four needle holding holes 451A to 451D, which positions are near the rear end positions of the suture locking grooves 452A to 452D. Each display 453 displays any one figure of 1 to 4 to indicate the place of the corresponding one of the sutures 407A, 407B, 407C, and 407D when counted from the distal end side of the outer cylinder 403 in the order.

The suturing needle 413 of the suture 407D at the endmost position of an inner cylinder 402 is inserted into the 4th needle holding hole 451D, and a B end portion 407b of the suture 407D is locked by the 4th suture locking groove 452D. Subsequently, the needles 413 of the sutures 407C, 407B, and 407A on the rear end side of the inner cylinder 402 are inserted in the order of 407A, 407B, and 407A in the corresponding needle holding holes 451A to 451C attached with figures indicating their positions in the order of 3, 2, and 1. Also, the B end portions 407b of the sutures 407C, 407B, and 407A are locked in the suture locking grooves 452A, 452B, and 452C attached with figures indicating their positions in the order.

Four undercuts 454 are formed in an inner cylinder gripping portion 404 at the distal end portion of the inner cylinder 402 to avoid interference of the suturing needles 413 inserted in the needle holding holes 451A to 451D with the distal-end projecting portion of the inner cylinder 402.

The operation of the above arrangement will be described. First, a method of using the suture holding member 401 according to the ninth embodiment will be described. The suture holding member 401 is used in combination with a forceps 421 having a shape corresponding to that shown in FIG. 89. The first forceps 42i may be of any type as far as it has a gripping function.

Figure 100:
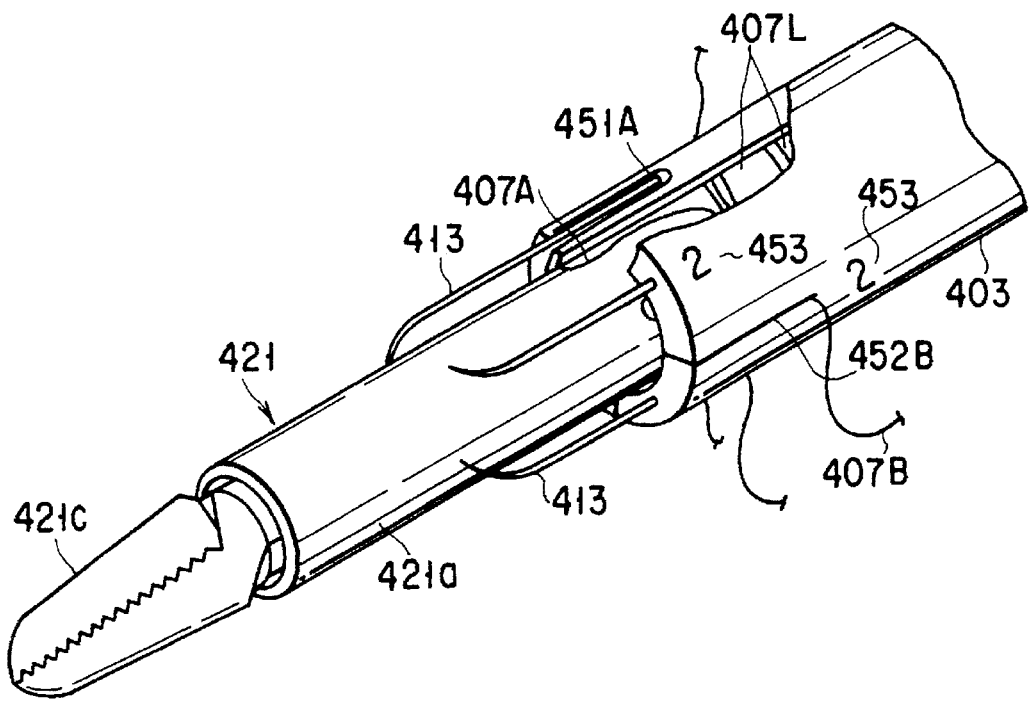
FIG. 100 is a perspective view showing a state wherein the first forceps is inserted into the outer cylinder.

First, as shown in FIG. 100, an inserting portion 421a of the first forceps 421 is inserted into the internal cavity of a forceps fixing portion 408 in the rear end portion of the outer cylinder 403 of the suture holding member 401, and the first forceps 421 is mounted in the outer cylinder 403 of the suture holding member 401 in the same manner as in the eighth embodiment.

After the mounting operation of the first forceps 421 and the outer cylinder 403 of the suture holding member 401 is ended in this manner, the first forceps 421, on which the outer cylinder 403 of the suture holding member 401 is mounted, is inserted into the body cavity through, e.g., a trocar, and a ligation operation of the living body tissues is performed.

Figure 101:
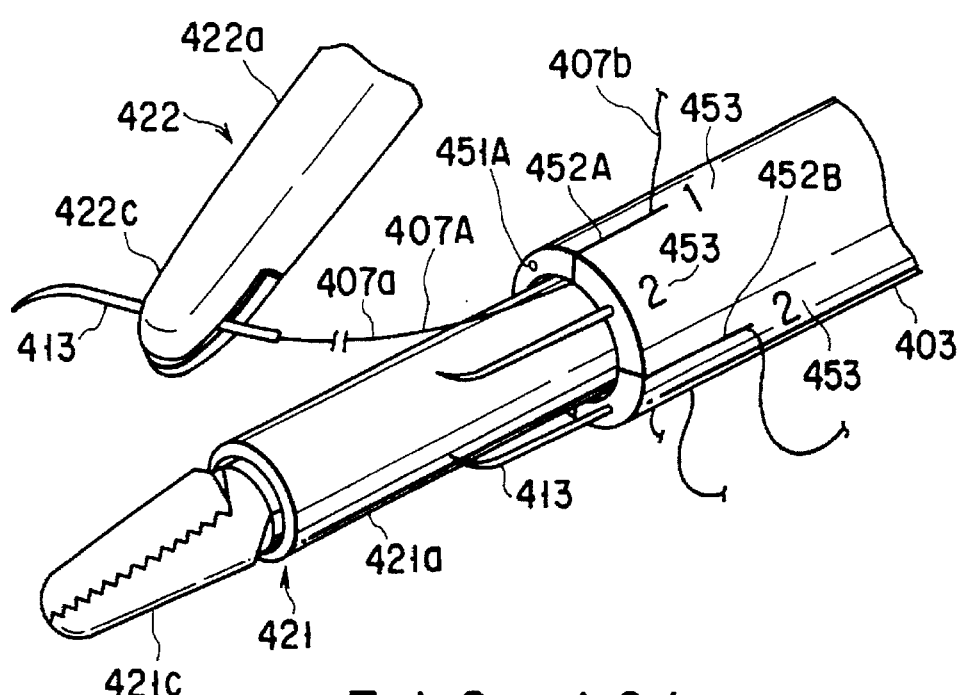
FIG. 101 is a perspective view showing a state wherein the suturing needle is pulled out from the needle holding hole by the second forceps.

As shown in FIG. 101, a forceps (to be referred to as the second forceps hereinafter) 422 which is different from the first forceps 421 is inserted into the body. The second forceps 422 is preferably a needle retainer. Furthermore, the first forceps 421 is inclined at an appropriate angle, as shown in FIG. 101, so that the second forceps 422 can easily seize each suturing needle 413, and the suturing needle 413 held in the first needle holding hole 451A is picked up by the second forceps 422.

Figure 102:
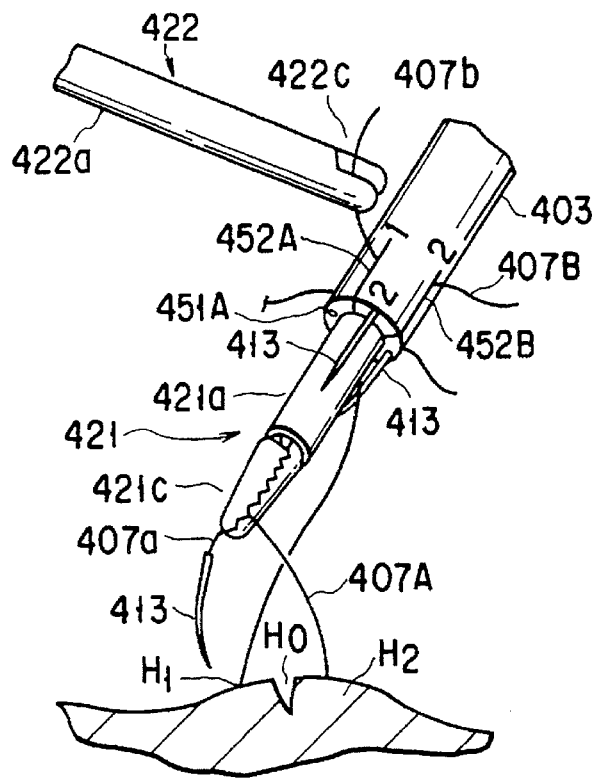
FIG. 102 is a perspective view showing a state wherein the suture is passed between tissues on the two sides of the wounded portion of living body tissues by the first forceps and the B end portion of the suture is gripped by the second forceps.

Subsequently, this suturing needle 413 is pierced between tissues $H_1$ and $H_2$ on the two sides of a wounded portion $H_0$ to pass the suture 407A through the tissues $H_1$ and $H_2$. Thereafter, as shown in FIG. 102, the A end portion 407a of the suture 407A on its needle 413 side is gripped by the first forceps 421. Furthermore, the B end portion 407b of the suture 407A in the first suture locking groove 452A of the suture holding member 401 is gripped by the second forceps 422. After this, ligation is performed in the same manner as in the eighth embodiment.

The above arrangement has the following effect. More specifically, since the needles 413 of the sutures 407A to 407D are held by the needle holding holes 451A to 451D in the distal end face of the outer cylinder 403, a needle 413 which is not in use will not be likely to contact an internal organ other than the target portion.

Furthermore, since the needles 413 of the sutures 407A to 407D are held in the corresponding needle holding holes 451A to 451D formed in the distal end face of the suturing needles 413 in the concentrated manner, the needles 413 of the sutures 407A to 407D will not be separately left in a dispersed state. For this reason, the needles 413 of the sutures 407A to 407D will not interfere with a suturing operation. Since the needles 413 of the sutures 407A to 407D are fixed in the needle holding holes 451A to 451D, the needles 413 can be easily picked up.

Figure 103:
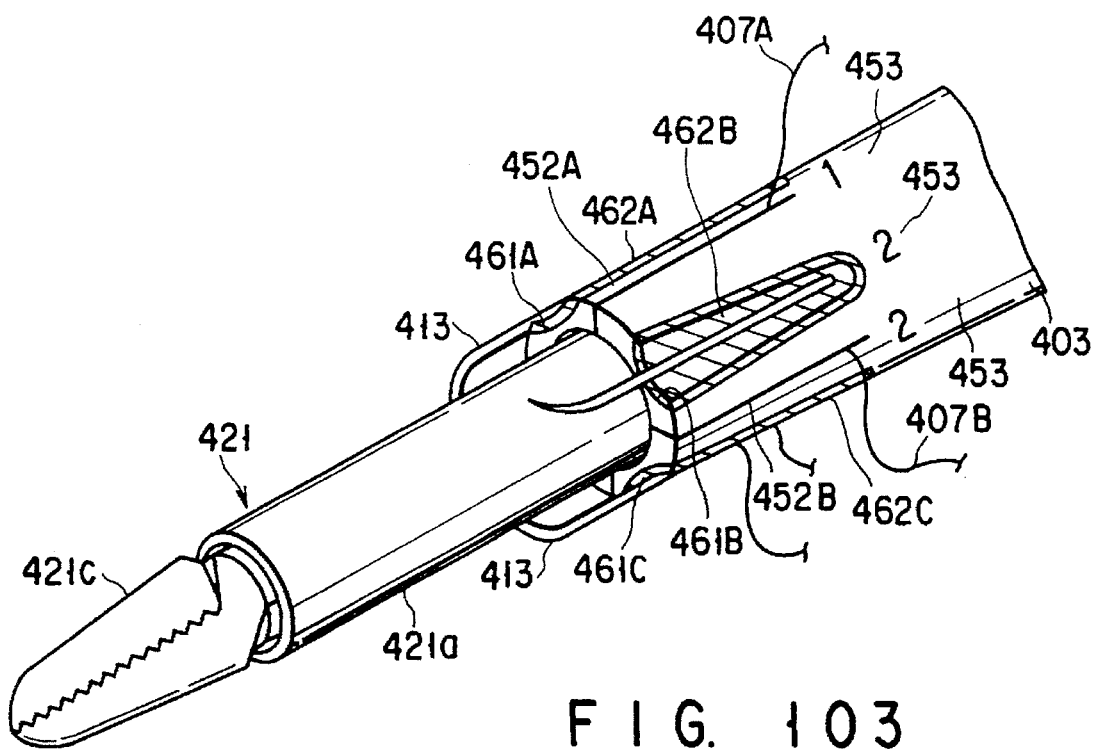
FIG. 103 is a perspective view showing a suture holding member according to the first modification of the ninth embodiment.

FIG. 103 shows the first modification of the ninth embodiment. In this modification, in place of the needle holding holes 451A to 451D, magnet mounting grooves 461A to 461D, which are recessed inwardly, are formed in the outer circumferential surface of an outer cylinder 403 at portions corresponding to the needle holding holes 451A to 451D, and magnets 462A to 462D for holding needles are fitted in the magnet mounting grooves 461A to 461D, respectively. The needles 413 of the sutures 407A to 407D are attracted by the magnetic force of the magnets 462A to 462D, respectively.

In the above arrangement, after final suture is performed, when needles 413 are to be removed from the body cavity, the used needles 413 can be easily held by the magnets 462A to 462D and recovered.

Figure 104A:
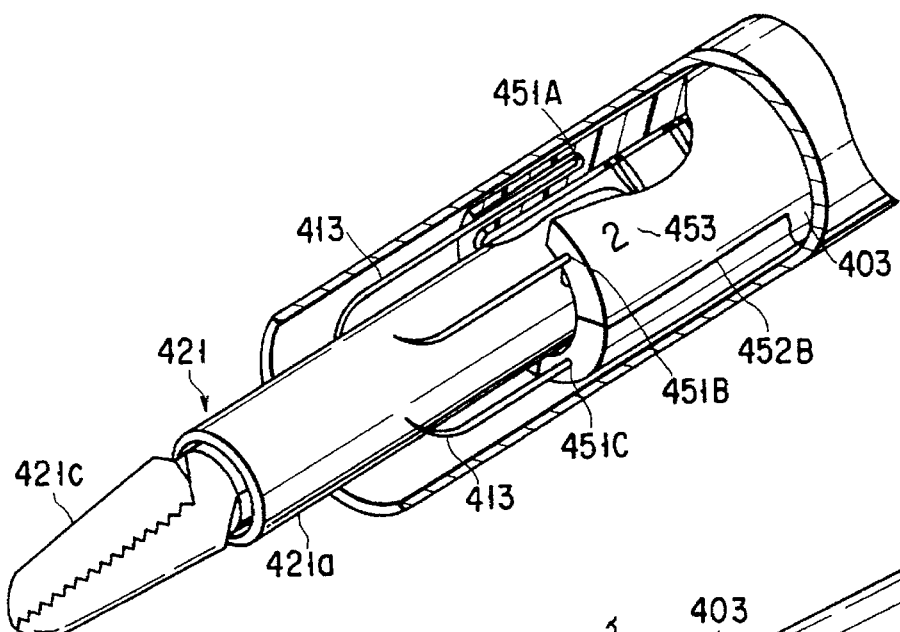
Figure 104B:
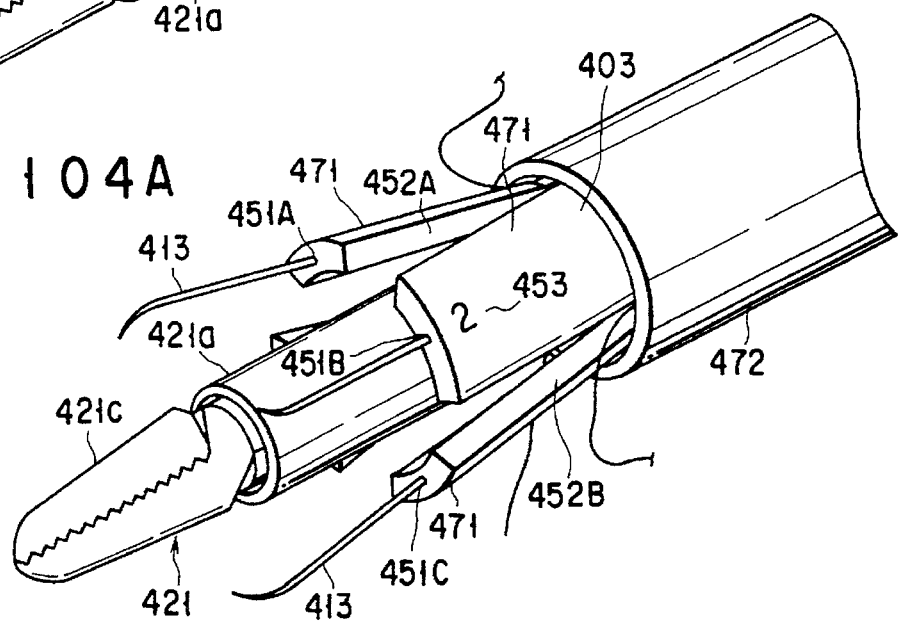

FIGS. 104A and 104B show the second modification of the ninth embodiment. In this modification, needle holding portions 471, each having an appropriate elasticity so that it tends to open outwardly, are provided between pairs of adjacent suture locking grooves 452A and 452B, 452B and 452C, 452C and 452D, and 452D and 452A at the distal end face of an outer cylinder 403, and a sheath 472 slidable in the axial direction is provided to cover the outer circumferential surface of the outer cylinder 403.

When the first forceps 421, on which the outer cylinder 403 of the suture holding member 401 is mounted, is to be inserted into the body cavity through, e.g., a trocar, the sheath 472 covers the outer circumferential surface of the outer cylinder 403 up to a position where it covers the entire portions of needles 413 held by needle holding holes 451A to 451D of the needle holding portions 471, as shown in FIG. 104A. After the first forceps 421 is inserted into the body cavity, the sheath 472 is slid toward the rear end side of the outer cylinder 403, as shown in FIG. 104B, so that the needle holding portions 471 are opened outwardly. In this case, therefore, the needles 413 of the sutures 407A to 407D can be easily picked up from the needle holding portions 471.

Figure 105:
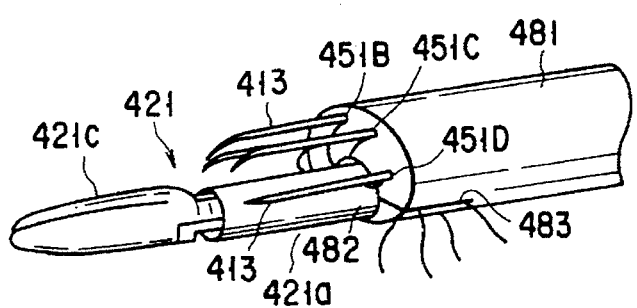
FIG. 105 is a perspective view showing a suture holding member according to the third modification of the ninth embodiment.

FIG. 105 shows the third modification of the ninth embodiment. In this modification, an forceps insertion port 482 is arranged in a main body 481 of the outer cylinder 403 of the suture holding member 401 to be eccentric from the axial position of the main body 481 of the outer cylinder 403, and the needle holding holes 451A to 451D are arranged to be gathered in a direction opposite to the direction of eccentricity of the forceps insertion port 482. Therefore, in this case, the needles 413 of the sutures 407A to 407D can be easily picked up from the needle holding holes 451A to 451D.

FIG. 106 shows the fourth modification of the ninth embodiment. In this modification, the needle holding holes 451A to 451D of the ninth embodiment are formed in the rear end face of the outer cylinder 403, and the needles 413 of the sutures 407A to 407D are inserted in the needle holding holes 451A to 451D backward and held in them. With this arrangement, since the needles 413 of the respective sutures 407A to 407D are not exposed in the front surface of the suture holding member 401, an ordinary forceps operation will not be interfered with.

FIG. 107 shows the fifth modification of the ninth embodiment. In this modification, four needle holding grooves 491 are formed in the outer circumferential surface of the outer cylinder 403 in accordance with the shapes of the needles 413 of the sutures 407A to 407D, and a plurality of small projections 492 for preventing dropping of the needles 413 are provided to the respective grooves 491. The needles 413 are held as they are fitted in the grooves 491. With this arrangement, since the distal ends of the needles 413 are not exposed to the outside, internal organs in the body cavity will not be likely to be damaged by contact with the needles 413.

FIGS. 108 to 112 show the tenth embodiment of the present invention. FIG. 108 schematically shows the arrangement of a suture holding member 501 of a suturing instrument. The suture holding member 501 is provided with an inner cylinder 502 and an outer cylinder 503 detachably coupled to the inner cylinder 502.

Figure 109:
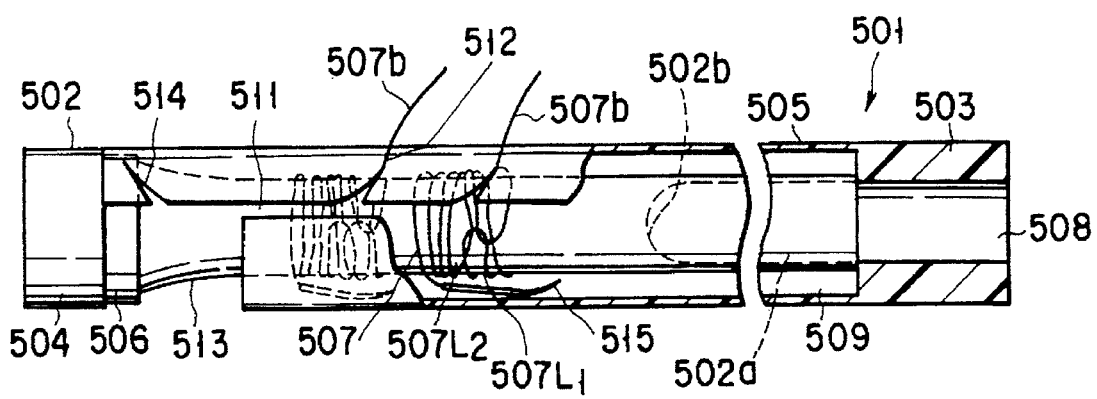
FIG. 109 is a partially cutaway sectional side view showing the suture holding member according to the tenth embodiment.

An inner cylinder gripping portion 504 is provided at the distal end portion of the inner cylinder 502. The inner cylinder gripping portion 504 has substantially the same outer diameter as that of the outer cylinder 503, and is thus not housed in the outer cylinder 503. As shown in FIG. 109, a suture winding portion 505 is provided on the rear end portion side of the inner cylinder 502, and a fixing portion 506 is provided between the inner cylinder gripping portion 504 and the suture winding portion 505. The suture winding portion 505 has a tapered surface formed on it, and is inserted into the outer cylinder 503. The fixing portion 506 is fitted on the inner circumferential wall surface of the outer cylinder 503 to fix the inner cylinder 502.

Figure 110:
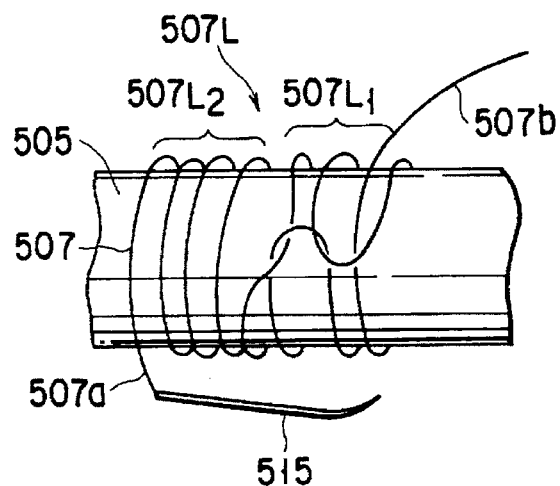
FIG. 110 is an explanatory view for explaining how to wind the suture on the suture winding portion of the inner cylinder.

A plurality (six in this embodiment) of sutures 507 are wound on the suture winding portion 505 of the inner cylinder 502 in accordance with the winding manner as shown in FIG. 110, to respectively form loop portions 507L. As shown in FIG. 110, each loop portion 507L includes a knot loop portion $507L_1$ (wound in the same manner as in FIG. 86) wound to form a knot later, and a suture portion $507L_2$ obtained by winding the extra portion of the corresponding suture 507. A needle 515 is provided at a distal end (A end portion) 507a of the extra portion $507L_2$.

As shown in FIG. 109, a closed portion 502b is provided in an inner hole 502a of the inner cylinder 502 on its inner cylinder gripping portion 504 side. The inner hole 502a terminates at the closed portion 502b of the inner cylinder 502 on its distal end portion side. A portion of the inner hole 502a of the inner cylinder 502 corresponding to the suture winding portion 505 has a larger inner diameter than that of the inserting portion of a forceps to be used in combination with the suture holding member 501, e.g., larger than that of an inserting portion 421a of a forceps 421 shown in FIG. 89.

A small-diameter forceps fixing portion 508 is formed in the outer cylinder 503 on its one end portion side, as shown in FIG. 109, and a suture housing portion 509 having a larger diameter than that of the forceps fixing portion 508 is formed in the outer cylinder 503 excluding the forceps fixing portion 508.

The suture housing portion 509 is set to have a length almost equal to the sum of the lengths of the fixing portion 506 and the suture winding portion 505 of the inner cylinder 502. The suture housing portion 509 has an inner diameter enough to be lightly fitted with the fixing portion 506 of the inner cylinder 502. The forceps fixing portion 508 has a forceps insertion port. This forceps insertion port has an inner diameter to allow the forceps fixing portion 508 to be lightly close-fitted on the outer circumferential surface of a forceps 421 to be used in combination with this suture holding member 501, thus maintaining air-tightness.

A suture passage groove 511 is formed in the outer circumferential surface of the outer cylinder 503 to be parallel to the axial direction of the outer cylinder 503. A plurality (six) of suture gripping grooves 512 are formed to extend from the suture passage groove 511 obliquely backward in the outer cylinder 503.

A needle escape portion 513 coupled to the suture passage groove 511 is provided near the distal end of the outer cylinder 503. The needle escape portion 513 is formed by cutting the lower half of the outer cylinder 503. The outer cylinder 503 has a semicircular section at this portion.

B end portions 507b of the respective sutures 507 wound on the inner cylinder 502, on their sides opposite to corresponding needles 515, are held in the suture gripping grooves 512. A suture locking groove 514 is obliquely provided in the distal end portion of the outer cylinder 503 so as to be continuous to the needle escape portion 513. Although the inner cylinder 502 is housed in the outer cylinder 503, the sutures 507 wound on the inner cylinder 502 are entirely housed in the outer cylinder 503 together with the corresponding needles 515.

Figure 111:
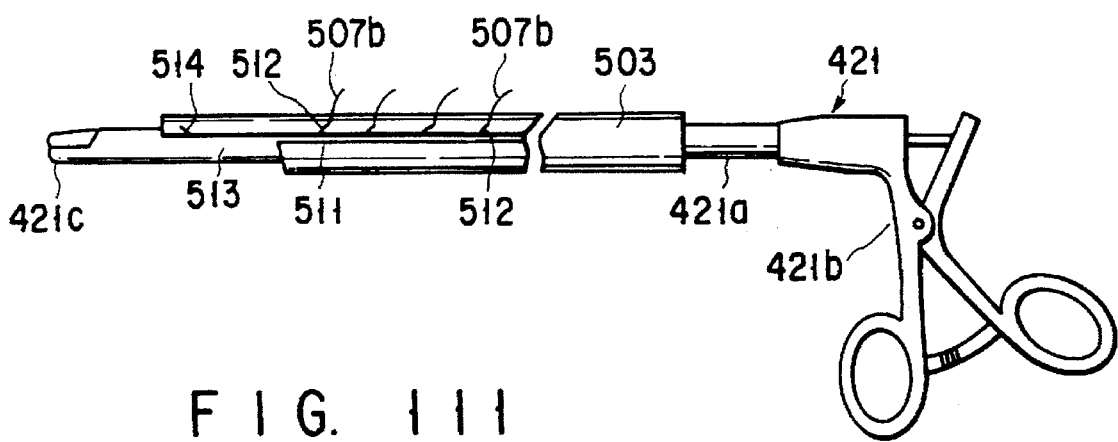
FIG. 111 is a side view showing a state wherein the first forceps is inserted into the outer cylinder.

The operation of the above arrangement will be described. The suturing instrument having the above arrangement is used in combination with the first forceps 421 shown in FIG. 89. The forceps (to be referred to as the first forceps hereinafter) 421 is inserted into the outer cylinder 503 from its rear end, as shown in FIG. 111, to push out the inner cylinder 502. At this time, the outer cylinder 503 is lightly close-fitted on the outer circumferential surface of the first forceps 421 with the forceps fixing portion 506, and is fixed on it.

Subsequently, the first forceps 421 is inserted into the body cavity through, e.g., a trocar. At this time, the contact portion of the trocar and the suture holding member 501 maintains air-tightness, and also the first forceps 421 and the suture holding member 501 are close-fitted with each other by the fixing portion 506, thus maintaining air-tightness.

As shown in FIG. 112A, another forceps (second forceps) 422 is inserted into the body cavity. The B end portion 507b of the first suture 507, when counted from the distal end of the outer cylinder 503, is gripped by the second forceps 422, and this suture 507 is removed from the suture gripping groove 512.

In this state, as shown in FIG. 112B, the suture 507 is pulled by the second forceps 422 to slide its loop portion 507L toward the distal end, and the B end portion 507b is caused to be caught by the suture locking groove 514 and held by it. When the distal end of the first forceps 421 is slightly swung, the suture portion $507L_2$ of the loop portion 507L is untied easily. Since the knot loop portion $507L_1$ is wound in a complicate manner, it is not untied easily.

After this, one-stitch suturing is performed in accordance with the same manner as in the eighth embodiment. When another one-stitch suturing is to be performed, the B end portions 507b of the sutures 507 are seized with the second forceps 422 sequentially from the one closer to the distal end of the outer cylinder 503. Then, one-stitch suturing is repeated in accordance with the same procedure as that described above.

In the above arrangement, since the needles 515 of the sutures 507 are completely housed in the outer cylinder 503, safety can be maintained. Also, air-tightness is maintained when pneumoperitoneum is needed.

FIG. 113 shows a modification of the tenth embodiment. In this modification, the suture housing portion 509 of the outer cylinder 503 has a diameter slightly larger than the outer diameter of the first forceps 421 to be used, and an O-ring 521 is mounted in the internal cavity of the suture housing portion 509. The first forceps 421 is inserted from a forceps insertion port. The outer cylinder 503 is fixed on the outer circumferential surface of the first forceps 421 by the clamping operation of the O-ring 521. With this arrangement, air-tightness between the first forceps 421 and the outer space is completely maintained by the O-ring 521.

FIG. 114 shows a suturing instrument 531 according to the eleventh embodiment of the present invention. This embodiment is obtained by incorporating, in place of the inner cylinder 502 of the tenth embodiment, a forceps member 532 in an outer cylinder 503 corresponding to that of the tenth embodiment. In this case, the forceps member 532 is fixed at a suture housing portion 509 of the outer cylinder 503.

In this forceps member 532, an operating portion 535 is coupled to an inserting portion 534 on its operator's hand side, and a gripping portion 536 at the distal end of the inserting portion 534 is opened/closed by the opening/closing lever of the operating portion 535.

The suturing instrument 531 having the above arrangement can be inserted as it is into a trocar or the like and can be used in the same manner as that of the tenth embodiment. Thus, a cumbersome operation of mounting and detaching a forceps 421 can be omitted. The suturing instrument 531 can also be used as an ordinary forceps.

Therefore, according to the eighth to eleventh embodiments described above, the suturing instrument is provided with a columnar member on which a plurality of sutures for forming loops to form a knot are mounted, an outer cylinder allowing loose insertion of the columnar member therein and having a hole for housing the loops, and having an locking portion for locking at least one portion of each suture, and a means for separately discriminating the plurality of sutures. Thus, an operation of suturing living body tissues ranging a comparatively large area in the body cavity can be performed efficiently.

The present invention is not limited to the embodiments described above, and various changes and modifications may be made without departing from the spirit and scope of the invention, as a matter of course.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. For use with a surgical instrument and a suture having a first end portion, a second end portion, and at least one loop formed in advance at an intermediate portion between the first and second end portions so as to have a predetermined size and be suitable for application to a body tissue, a suture ligature instrument for forming a suitable knot in a piece of the suture within a body cavity with the surgical instrument, the suture ligature instrument comprising:

holding means for holding the at least one loop of the suture so as to substantially maintain a size of the at least one loop, said holding means having fastening means for fastening at least one portion of the suture; and fixing means for fixing said holding means at a distal end portion of the surgical instrument so that when the surgical instrument is inserted into a body cavity, the holding means is inserted into the body cavity together with the at least one formed loop held by said holding means;

wherein said holding means includes a substantially cylindrical body arranged to surround a circumferential portion of the surgical instrument, said substantially cylindrical body having a first end portion arranged at a distal end of the surgical instrument, a second end portion arranged at an operating portion of the surgical instrument, an inner circumferential portion, and an outer circumferential portion, and at least one of said inner and outer circumferential portions being capable of holding at least one loop;

wherein said fixing means includes an extending portion extending from said second end portion of said substantially cylindrical body to fix said substantially cylindrical body on the surgical instrument; and wherein said extending portion has a thick-walled annular structure in which an axial hole having an inner diameter substantially corresponding to an outer diameter of the surgical instrument is formed, and said fixing means has one of a plurality of incision grooves and projections that are arranged to be separate from each other along a circumferential portion of the axial hole and extending in a radial direction, thereby enabling said body to be movable on the surgical instrument in the axial direction.

2. An instrument according to claim 1, wherein said holding means includes at least two film-like members, and the at least one loop is held between said film-like members such that a loop shape of the at least one loop is maintained.

3. An instrument according to claim 2, wherein each of said film-like members has an opening substantially corresponding to the at least one loop, and the surgical instrument is passed through the opening.

4. An instrument according to claim 2, further comprising a plurality of units each including two film-like members, said units being coupled to each other.

5. An instrument according to claim 1, wherein the suture has one end attached with a needle, and said holding means has needle fixing means for temporarily fixing the needle.

6. An instrument according to claim 1, wherein
the surgical instrument includes an adaptor having at least one groove for latch-engaging with and fixing the suture/ligation instrument; and
said fixing means includes latch means engageable with the at least one groove of said extending portion.

7. An instrument according to claim 1, wherein said firing means has a clamping ring for clamping said extending portion on an outer circumferential surface of the surgical instrument.

8. An instrument according to claim 1, further including the at least on loop wherein said at least one loop includes a group of loops, the group including an open small loop arranged in a circumferential direction of said holding means and having two legs extending in the circumferential direction so as to pass through the open small loop, the two legs forming a closed large loop.

9. For use with a surgical instrument and a suture having a first end portion, a second end portion, and at least one loop formed in advance at an intermediate portion between the first and second end portions so as to have a predetermined size and be suitable for application to a body tissue, a suture ligature instrument for forming a suitable knot in a piece of the suture within a body cavity with the surgical instrument, the suture ligature instrument comprising:

holding means for holding the at least one loop of the suture so as to substantially maintain a size of the at least one loop, said holding means having fastening means for fastening at least one portion of the sutures;

fixing means for fixing said holding means at a distal end portion of the surgical instrument so that when the surgical instrument is inserted into a body cavity, the holding means is inserted into the body cavity together with the at least one formed loop held by said holding means; and guide means for guiding the at least one loop onto a circumferential portion of the surgical instrument so that said distal end portion of the surgical instrument extends through the at least one loop;

wherein said holding means includes a substantially cylindrical body arranged to surround the circumferential portion of the surgical instrument, said body having a first end portion arranged at a distal end of the surgical instrument, a second end portion arranged at an operating portion of the surgical instrument, an inner circumferential portion, and an outer circumferential portion, and at least one of said inner and outer circumferential portions being capable of holding at least one loop;

wherein said guide means includes a second body to be inserted into said substantially cylindrical body of said holding means from a side of said first end portion thereof, said second body defining a space together with said cylindrical body for housing the at least one loop, and when the surgical instrument is inserted into said substantially cylindrical body from a side of said second end portion thereof, said second body is pushed out from said cylindrical body, thereby guiding the at least one loop to the circumferential portion of the surgical instrument; and wherein said second body has a cylindrical outer circumferential surface for temporarily holding the at least one loop, and an axial hole having an end portion which is close to said second end portion of said cylindrical body and which is open outward, and said second body is pushed out from an interior of said cylindrical body by the surgical instrument inserted in the axial hole.

10. A method of preparing a suture/ligature instrument, for forming a suitable knot in a piece of suture in a body cavity, the method comprising the steps of:

providing a suture and a surgical instrument having a distal end portion with gripping means and an operating portion for operating the distal end portion;

providing a suture holding member including a substantially cylindrical body having a first end portion and a second end portion;

forming at least one loop, which is to form the knot, in said suture;

causing the at least one loop to be held by said suture holding member;

said steps of forming at least one loop and causing the at least one loop to be held by the suture holding member includes the steps of forming the at least one loop on a core that can be inserted into the cylindrical body through the first end portion thereof, and inserting the core into the body cavity; and assembling said suture holding member with the surgical instrument such that the distal end portion of the surgical instrument passes through the loop, the step of assembling said suture holding member with the surgical instrument including a step of inserting said core into said body, and pushing out said core with the distal end portion of the surgical instrument which is inserted through said second end portion thereof, while moving the loop from said core to the distal end portion of the surgical instrument.

11. A method according to claim 10, wherein the step of forming at least one loop includes the step of forming a plurality of loops.

12. A method according to claim 10, wherein said suture holding member includes two film-like members, and the step of causing the loop to be held by said suture holding member includes the step of sandwiching the loop between said film-like members.

13. A method according to claim 12, wherein said two film-like members have openings substantially corresponding to the at least one loop, and the step of assembling said suture holding member with the surgical instrument includes the step of passing the distal end portion of the surgical instrument through the openings.

14. A method of preparing a suture/ligature instrument for forming a suitable knot in a piece of suture in a body cavity, the method comprising the steps of:

providing a suture and a surgical instrument having a distal end portion with gripping means and an operating portion for operating the distal end portion;

preparing a suture holding member that includes a suture on which at least one loop to be formed into the knot is formed and holds the loop, said suture holding member including a substantially cylindrical body having a first end portion and a second end portion, with the loop being formed on a core that can be inserted into said cylindrical body through said first end portion thereof; and assembling said suture holding member with said surgical instrument such that said distal end portion of said surgical instrument passes through the loop, the step of assembling including the step of pushing out said core with the distal end portion of the surgical instrument which is inserted through said second end portion thereof, while moving the loop from said core to the distal end portion of the surgical instrument.

\* \* \* \* \*